US011331391B2

(12) United States Patent
McKenna et al.

(10) Patent No.: US 11,331,391 B2
(45) Date of Patent: May 17, 2022

(54) PHOSPHONATE-DRUG CONJUGATES

(71) Applicants: Massachusetts Eye and Ear Infirmary, Boston, MA (US); University of Southern California, Los Angeles, CA (US)

(72) Inventors: Charles E. McKenna, Pacific Palisades, CA (US); Boris A. Kashemirov, Los Angeles, CA (US); Shuting Sun, Los Angeles, CA (US); Kim Nguyen, Los Angeles, CA (US); David Jung, Winchester, MA (US); Michael J. McKenna, Southborough, MA (US); William Sewell, Sherborn, MA (US); Judith Kempfle, Brookline, MA (US); Woo Seok Kang, Chestnut Hill, MA (US); Albert Edge, Brookline, MA (US)

(73) Assignees: Massachusetts Eye and Ear Infirmary, Boston, MA (US); University of Southern California, Los Angeles, CA (US)

( * ) Notice: Subject to any disclaimer, the term of this patent is extended or adjusted under 35 U.S.C. 154(b) by 0 days.

(21) Appl. No.: 16/072,456

(22) PCT Filed: Jan. 25, 2017

(86) PCT No.: PCT/US2017/014944
§ 371 (c)(1),
(2) Date: Jul. 24, 2018

(87) PCT Pub. No.: WO2017/132263
PCT Pub. Date: Aug. 3, 2017

(65) Prior Publication Data
US 2019/0030172 A1    Jan. 31, 2019

Related U.S. Application Data

(60) Provisional application No. 62/286,912, filed on Jan. 25, 2016.

(51) Int. Cl.
A61K 47/54 (2017.01)
A61P 27/16 (2006.01)
A61K 9/00 (2006.01)
A61K 31/353 (2006.01)
A61K 31/496 (2006.01)
A61K 31/675 (2006.01)
A61K 31/7088 (2006.01)
C12N 9/22 (2006.01)
C12N 15/11 (2006.01)

(52) U.S. Cl.
CPC ......... *A61K 47/548* (2017.08); *A61K 9/0019* (2013.01); *A61K 9/0046* (2013.01); *A61K 31/353* (2013.01); *A61K 31/496* (2013.01); *A61K 31/675* (2013.01); *A61K 31/7088* (2013.01); *A61P 27/16* (2018.01); *C12N 9/22* (2013.01); *C12N 15/11* (2013.01); *C12N 2310/20* (2017.05); *C12N 2310/351* (2013.01); *C12N 2800/80* (2013.01)

(58) Field of Classification Search
CPC .. A61K 31/353; A61K 31/496; A61K 31/675; A61K 31/7088; A61K 47/548; A61K 9/0019; A61K 9/0046; C12N 15/11; C12N 2310/20; C12N 2310/351; C12N 2800/80; C12N 9/22
See application file for complete search history.

(56) References Cited

U.S. PATENT DOCUMENTS

| 7,781,419 B2 | 8/2010 | Brookler |
| 8,772,268 B2 | 7/2014 | Freel Meyers et al. |
| 2013/0203998 A1* | 8/2013 | McKenna ............ C07F 9/3873 546/22 |
| 2015/0166585 A1 | 6/2015 | Margel et al. |

OTHER PUBLICATIONS

Kempfle et al, Bioconjugate Chem., 2018 25, 1240-1250 (Year: 2018).*
Kashemirov et al., Bio-conjugate Chem.2008, 19, 2308-2310 (Year: 2008).*
Kang et al., Otol Neurotol Jul. 2015, 36(6): 953-960 (Year: 2015).*
Hokugo et al., Bone. Mar. 2013; 53(1): 59-68. (Year: 2013).*
Allen and Burr, "Bisphosphonate effects on bone turnover, microdamage, and mechanical properties: what we think we know and what we know that we don't know," Bone, 2011, 49:56-65.
Bae et al., "Development of oral osteomucosal tissue constructs in vitro and localization of fluorescently-labeled bisphosphonates to hard and soft tissue," Int J Mol Med, 2014, 34:559-63.
Balle and Linthicum, "Histologically proven cochlear otosclerosis with pure sensorineural hearing loss," Ann Otol Rhinol Laryngol, 1984, 93:105-11.
Barakat, "Do We Need Small Molecule Inhibitors for the Immune Checkpoints?," 2014, J Pharma Care Health Sys, 1:e119.
Bellido and Plotkin "Novel actions of bisphosphonates in bone: preservation of osteoblast and osteocyte viability," Bone, 2011, 49:50-5.
Bertrand et al., "The Crystal Structures of TrkA and TrkB Suggest Key Regions for Achieving Selective Inhibition," J Mol Biol, 2012, 423:439-453.

(Continued)

*Primary Examiner* — Jean P Cornet
(74) *Attorney, Agent, or Firm* — Fish & Richardson P.C.

(57) ABSTRACT

This invention relates to drug conjugates useful for localized treatment of diseases or disorders of the middle ear and/or inner ear. Methods of treating diseases or disorders of the middle ear and/or inner ear, pharmaceutical compositions comprising the conjugates, and methods of inhibiting a Tropomyosin receptor kinase are also provided.

10 Claims, 24 Drawing Sheets

(56) References Cited

OTHER PUBLICATIONS

Bianchi et al., "Degeneration of vestibular neurons in late embryogenesis of both heterozygous and homozygous BDNF null mutant mice," Development, 1996, 122:1965-1973.
Chen et al., "Pharmacokinetics and pharmacodynamics of zoledronic acid in cancer patients with bone metastases," J Clin Pharmacol, 2002, 42:1228-36.
Chole and McKenna, "Pathophysiology of otosclerosis," Otol Neurotol, 2001, 22:249-57.
Clayton et al., "Association between osteoporosis and otosclerosis in women," J Laryngol Otol, 2004,118:617-21.
Doherty and Linthicum, "Spiral ligament and stria vascularis changes in cochlear otosclerosis: effect on hearing level," Otol Neurotol, 2004, 25:457-64.
Ealy and Smith, "Otosclerosis," Adv Otorhinolaryngol, 2011, 70:122-9.
Ebetino et al., "The relationship between the chemistry and biological activity of the bisphosphonates," Bone, 2011, 49:20-33.
Ernfors et al., "Studies on the physiological role of brain-derived neurotrophic factor and neurotrophin-3 in knockout mice," The International Journal of Developmental Biology, 1995, 39:799-807.
Fletcher and Gunning, "Mild, efficient and rapid O-debenzylation of ortho-substituted phenols with trifluoroacetic acid," Tetrahedron Letters, 2008, 49:4817-4819.
Frisch et al., "Estimation of volume referent bone turnover in the otic capsule after sequential point labeling," Ann Otol Rhinol Laryngol, 2000, 109:33-9.
Fritzsch et al., "Lack of neurotrophin 3 causes losses of both classes of spiral ganglion neurons in the cochlea in region-specific fashion," Journal of Neuroscience, 1997, 17:6213-6225.
Full Prescribing Information for Reclast (zoledronic acid), Novartis Pharmaceutical Corporation, 2011, 29 pages https://www.accessdata.fda.gov/drugsatfda_docs/nda/2011/021817Orig1s012.pdf.
Green et al., "The Trk A, B, C's of neurotrophins in the cochlea," Anatomical Record, 2012, 295:1877-1895.
Hirabayashi et al., "Bone-specific delivery and sustained release of diclofenac, a non-steroidal anti-inflammatory drug, via bisphosphonic prodrug based on the Osteotropic Drug Delivery System (ODDS)," Journal of Controlled Release, 2001, 70: 183-191.
Hodge et al, "The tipping point for combination therapy: cancer vaccines with radiation, chemotherapy, or targeted small molecule inhibitors," Semin Oncol, 2012, 39(3):323-39.
Hokugo et al., "Equilibrium-dependent bisphosphonate interaction with crystalline bone mineral explains anti-resorptive pharmacokinetics and prevalence of osteonecrosis of the jaw in rats," Bone, 2013, 53:59-68.
Ichida et al, "A small-molecule inhibitor of tgf-Beta signaling replaces sox2 in reprogramming by inducing nanog," 2009, Cell Stem Cell, 5(5):491-503.
Igarashi et al., "Morphometric comparison of endolymphatic and perilymphatic spaces in human temporal bones," Acta Otolaryngol, 1986, 101:161-4.
International Preliminary Report on Patentability in International Application No. PCT/US2017/014944, dated Jul. 31, 2018, 7 pages.
International Search Report and Written Opinion in International Application No. PCT/US2017/014944, dated Apr. 18, 2017, 12 pages.
Jang et al., "A selective TrkB agonist with potent neurotrophic activities by 7,8-dihydroxyflavone," PNAS, Feb. 2010, 107(6):2687-2692.
Kabbara et al., "Decisive criteria between stapedotomy and cochlear implantation in patients with far advanced otosclerosis," Otol Neurotol, 2015, 36:e73-8.
Kang et al., Direct Visualization of Cochlear Drug Delivery Using a Novel Fluorescent Bisphosphonate Compound, Presented at the 37th Annual Midwinter Meeting, San Diego, CA, Feb. 22-26, 2014, 14 pages.

Kang et al., "Improved Bisphosphonate Targeting to the Mammalian Cochlea via Local Delivery," Presented at the Collegium Oto-Rhino-Laryngologicum Amicitiae Sacrum Annual Meeting 2014, Istanbul, Aug. 24-28, 2014, 17 pages.
Kang et al., "Local Delivery of Bisphosphonate to the Mammalian Cochlea," Poster, 7th International Symposium on Middle Ear Mechanics in Research and Otology (MEMRO), Aalborg, Denmark, Jul. 1-5, 2015, 1 page.
Kang et al., "Non-Ototoxic Local Delivery of Bisphosphonate to the Mammalian Cochlea," Otology & Neurology, 2015; 36:953-960.
Kang et al., "OTOP-67: Ototoxicity of Intracochlear Zoledronate Delivery Confirmed with Direct Visualization over a Short-term and a Long-term Period," 2015 International Congress of Korean Society of Otorhinolaryngology—Head & Neck Surgery, Oral Presentation, Apr. 26, 2015, Seoul, Korea, p. 91.
Kang et al., "Ototoxicity of Intracochlear Zoledronate Delivery Over a Short-term and a Long-term Period," Presented at the 2015 International Congress of Korean Society of Otorhinolaryngology—Head & Neck Surgery, Seoul, South Korea, Apr. 24-26, 2015, 13 pages.
Kang et al., "Progress Towards Developing Inner Ear Drug Delivery Systems," Presented at the 2013 Asian Forum on Otology-Neurotology, Seoul, South Korea, 2013, 32 pages.
Kang et al., "Studies on local delivery of bisphosphonate for the treatment of cochlear otosclerosis," Presented at the 13th Triennial Meeting The International Otopathology Society, Boston, MA, Jun. 9-11, 2013, 15 pages.
Kang et al., Abstract #: PD-115: Direct Visualization of Cochlear Drug Delivery Using a Novel FluoPD—rescent Bisphosphonate Compound, ARO Abstracts, 37th Annual Midwinter Meeting, San Diego, CA, Feb. 22-26, 2014, 37:286-287.
Kao et al, "Loss of osteoprotegerin expression in the inner ear causes degeneration of the cochlear nerve and sensorineural hearing loss," Neurobiology of Disease, 2013, 56:25-33.
Kashemirov et al., "Fluorescently labeled risedronate and related analogues: "magic linker" synthesis," Bioconjug Chem, 2008, 19:2308-10.
Khetarpal and Schnknecht, "In search of pathologic correlates for hearing loss and vertigo in Paget's disease. A clinical and histopathologic study of 26 temporal bones," Ann Otol Rhinol Laryngol Suppl, 1990, 145:1-16.
Khoo et al., "Formulations for trans-tympanic antibiotic delivery," Biomaterials, 2013, 34:1281-8.
Kozloff et al., "Near-infrared fluorescent probe traces bisphosphonate delivery and retention in vivo," J Bone Miner Res, 2010, 25:1748-58.
Kucuk et al., "Microstructures of the bony modiolus in the human cochlea: a scanning electron microscopic study," J Electron Microsc (Tokyo), 1991,40:193-7.
Kujawa and Liberman, "Acceleration of age-related hearing loss by early noise exposure: evidence of a misspent youth," The Journal of Neuroscience, 2006, 26:2115-2123.
Kujawa and Liberman, "Adding insult to injury: cochlear nerve degeneration after "temporary" noiseinduced hearing loss," The Journal of Neuroscience, 2009, 29:14077-14085.
Kujawa and Liberman, "Synaptopathy in the noise-exposed and aging cochlea: Primary neural degeneration in acquired sensorineural hearing loss,"Hearing Research, 2015.
Lajud et al., "A regulated delivery system for inner ear drug application," J Control Release, 2013, 166:268-76.
Lee et al., "Syntheses and activities of new C10 beta-turn peptidomimetics," J Org Chem, 2004, 69:701-713.
Lewiecki, "Safety of long-term bisphosphonate therapy for the management of osteoporosis," Drugs, 2011, 71:791-814.
Li et al., "A kinase inhibitor screen identifies small-molecule enhancers of reprogramming and iPS cell generation," Nat Commun, 2012, 3:1085.
Lin et al., "Hearing Loss Prevalence and Risk Factors Among Older Adults in the United States," Journals of Gerontology: Series A—Biological Sciences and Medical Sciences, 2011, 66:582-590.
Lipton, "New therapeutic agents for the treatment of bone diseases," Expert Opin Biol Ther, 2005, 5:817-32.

(56) References Cited

OTHER PUBLICATIONS

Marma et al., "Synthesis and biological evaluation of alpha-halogenated bisphosphonate and phosphonocarboxylate analogues of risedronate," J Med Chem, 2007, 50:5967-5975.
Marshall et al., "Cochlear implantation in cochlear otosclerosis," Laryngoscope, 2005, 115:1728-33.
McKenna et al., "Abstract #: P8-2: Local delivery of bisphosphonate to the mammalian cochlea—a prelude to direct delivery in humans via a drug eluting stapes prosthesis," 7th International Symposium on Middle Ear Mechanics in Research and Otology (MEMRO), Jul. 1-5, 2015, Aalborg, Denmark, p. 69.
McKenna et al., "Association of otosclerosis with Sp1 binding site polymorphism in COL1A1 gene: evidence for a shared genetic etiology with osteoporosis," Otol Neurotol, 2004, 25:447-50.
Mueller and Barr-Gillespie, "New treatment options for hearing loss," Nature Reviews Drug Discovery, 2015, 14:346-U384.
Mynatt et al., "Demonstration of a longitudinal concentration gradient along scala tympani by sequential sampling of perilymph from the cochlear apex," J Assoc Res Otolaryngol, 2006, 7:182-93.
Nadol, Jr., "Patterns of neural degeneration in the human cochlea and auditory nerve: implications for cochlear implantation," Otolaryngology, 1997, 117:220-228.
Noushi et al., "Delivery of neurotrophin-3 to the cochlea using alginate beads," Otology & Neurotology, 2005, 26:528-533.
Ohyama et al., "Volume flow rate of perilymph in the guinea-pig cochlea," Hear Res, 1988, 35:119-29.
Paasche et al., "Technical report: modification of a cochlear implant electrode for drug delivery to the inner ear," Otol Neurotol, 2003, 24:222-7.
Papapetrou, "Bisphosphonate-associated adverse events," Hormones (Athens), 2009, 8:96-110.
Parker et al., "Primary culture and plasmid electroporation of the murine organ of Corti." J Vis Exp, 2010.
Peters et al., "Middle-ear endoscopy and trans-tympanic drug delivery using an interventional sialendoscope: feasibility study in human cadaveric temporal bones," J Laryngol Otol, 2010, 124:1263-7.
Pinchot et al, "Identification and validation of Notch pathway activating compounds through a novel high-throughput screening method," Cancer, 2011, 117(7):1386-98.
Plontke et al., "Concentration gradient along the scala tympani after local application of gentamicin to the round window membrane," Laryngoscope, 2007, 117:1191-8.
Pujol et al., "Pathophysiology of the glutamatergic synapses in the Cochlea," Acta oto-laryngologica,1993, 113:330-334.
Quesnel et al., "Third-Generation Bisphosphonates for Treatment of Sensorineural Hearing Loss in Otosclerosis," Otol Neurotol, 2012, 33:1308-1314.
Rama-Lopez et al., "Cochlear implantation of patients with far-advanced otosclerosis." Otol Neurotol, 2006, 27:153-8.
Ramekers et al., "Neurotrophins and their role in the cochlea," Hearing Research, 2012, 288:19-33.
Ramekers et al., "Temporary Neurotrophin Treatment Prevents Deafness-Induced Auditory Nerve Degeneration and Preserves Function," The Journal of Neuroscience, 2015, 35:12331-12345.
Ramsden et al., "Cochlear implantation in otosclerotic deafness," Adv Otorhinolaryngol, 2007, 65:328-34.
Rask-Andersen et al., "Perilymph/modiolar communication routes in the human cochlea," Ear Hear, 2006, 27:457-65.
Rauch et al., "Oral vs intratympanic corticosteroid therapy for idiopathic sudden sensorineural hearing loss: a randomized trial," Jama, 2011, 305:2071-2079.
Roelofs et al., "Fluorescent Risedronate Analogues Reveal Bisphosphonate Uptake by Bone Marrow Monocytes and Localization Around Osteocytes In Vivo," Journal of Bone and Mineral Research, 2010, 25:606-616.
Roelofs et al., "Influence of bone affinity on the skeletal distribution of fluorescently labeled bisphosphonates in vivo," J Bone Miner Res, 2012, 27:835-47.
Rogers et al., "Biochemical and molecular mechanisms of action of bisphosphonates," Bone, 2011, 49:34-41.
Roy et al., "Strategies for drug delivery to the human inner ear by multifunctional nanoparticles," Nanomedicine (Lond), 2012, 7:55-63.
Russell, "Bisphosphonates: mode of action and pharmacology," Pediatrics, 2007, 119 Suppl 2:S150-62.
Salt et al., "Marker entry into vestibular perilymph via the stapes following applications to the round window niche of guinea pigs," Hear Res, 2012, 283:14-23.
Salt et al., "Perilymph Kinetics of FITC—Dextran Reveals Homeostasis Dominated by the Cochlear Aqueduct and Cerebrospinal Fluid," J Assoc Res Otolaryngol, 2015, 16:357-71.
Salt et al., "Radial communication between the perilymphatic scalae of the cochlea. II: Estimation by bolus injection of tracer into the sealed cochlea," Hear Res, 1991, 56:37-43.
Salt, "Dexamethasone concentration gradients along scala tympani after application to the round window membrane," Otol Neurotol, 2008, 29:401-6.
Santos et al., "Otopathology in Osteogenesis Imperfecta," Otol Neurotol, 2012, 33:1562-6.
Schiller et al., "Summary health statistics for U.S. adults: National Health Interview Survey, 2010," Vital Health Stat, 2012, 252:1-207.
Schuknecht and Gacek, "Cochlear pathology in presbycusis," The Annals of Otology, Rhinology, and Laryngology, 1993, 102:1-16.
Semaan et al., "Cochlear implantation outcomes in patients with far advanced otosclerosis." Am J Otolaryngol, 2012, 33:608-14.
Sergeyenko et al., "Age-related cochlear synaptopathy: an early-onset contributor to auditory functional decline," The Journal of Neuroscience, 2013, 33:13686-13694.
Seyyedi et al., "Within-subject comparison of word recognition and spiral ganglion cell count in bilateral cochlear implant recipients," Otology & Neurotology, 2014, 35:1446-1450.
Shibata et al., "Transgenic BDNF induces nerve fiber regrowth into the auditory epithelium in deaf cochleae," Experimental Neurology, 2010, 223:464-472.
Shinomori et al., "Volumetric and dimensional analysis of the guinea pig inner ear," Ann Otol Rhinol Laryngol, 2001, 110:91-8.
Silos-Santiago et al., "Severe sensory deficits but normal CNS development in newborn mice lacking TrkB and TrkC tyrosine protein kinase receptors," The European Journal of Neuroscience, 1997, 9:2045-2056.
Silverman and Landesberg, "Osteonecrosis of the jaw and the role of bisphosphonates: a critical review," Am J Med, 2009, 122:S33-45.
Stankovic et al., "Survival of adult spiral ganglion neurons requires erbB receptor signaling in the inner ear," The Journal of Neuroscience, 2004, 24:8651-8661.
Sun et al., "Fluorescent bisphosphonate and carboxyphosphonate probes: a versatile imaging toolkit for applications in bone biology and biomedicine," Bioconjugate Chem, 2016, 27: 329-340.
Sun et al., "Studies on gambogic acid (IV): Exploring structure-activity relationship with I kappa B kinase-beta (IKK beta)," European Journal of Medicinal Chemistry, 2012, 51:110-123.
Sun et al., "Synthesis and characterization of novel fluorescent nitrogen-containing bisphosphonate imaging probes for bone active drugs," Phosphorus Sulfur Silicon Relat Elem, 2011, 186:970-1.
Swan et al., "Inner ear drug delivery for auditory Applications," Advanced Drug Delivery Reviews, 2008, 60:1583-1599.
Swan et al., "Proteomics analysis of perilymph and cerebrospinal fluid in mouse," Laryngoscope, 2009, 119:953-958.
Trott and Olson, "Software News and Update AutoDock Vina: Improving the Speed and Accuracy of Docking with a New Scoring Function, Efficient Optimization, and Multithreading," J Comput Chem, 2010, 31:455-461.
Turek et al., "Bisphosphonate binding affinity affects drug distribution in both intracortical and trabecular bone of rabbits," Calcif Tissue Int, 2012, 90:202-10.
Veldboer et al., "Determination of zoledronic acid in human urine and blood plasma using liquid chromatography/electrospray mass spectrometry," Journal of Chromatography B, 2011, 879:2073-2080.

(56) References Cited

OTHER PUBLICATIONS

Vermeer et al., "Jaw bone marrow-derived osteoclast precursors internalize more bisphosphonate than long-bone marrow precursors," Bone, 2013, 57:242-51.

Viana et al., "Cochlear neuropathy in human presbycusis: Confocal analysis of hidden hearing loss in post-mortem tissue," Hearing Research, 2015, 327:78-88.

Wan et al., "Neurotrophin-3 regulates ribbon synapse density in the cochlea and induces synapse regeneration after acoustic trauma," Elife, 2014, 3.

Wang and Green, "Functional role of neurotrophin-3 in synapse regeneration by spiral ganglion neurons on inner hair cells after excitotoxic trauma in vitro," The Journal of Neuroscience, 2011, 31:7938-7949.

Wang et al., "Dose-dependent sustained release of dexamethasone in inner ear cochlear fluids using a novel local delivery approach," Audiology & Neuro-Otology, 2009, 14:393-401.

Wang et al., "OTO-201: Nonclinical Assessment of a Sustained-Release Ciprofloxacin Hydrogel for the Treatment of Otitis Media," Otol Neurotol, 2014, 35:459-69.

Wang et al., "Principles of inner ear sustained release following intratympanic administration," Laryngoscope, 2011;121:385-91.

Wen et al., "Anatomic site variability in rat skeletal uptake and desorption of fluorescently labeled bisphosphonate," Oral Dis, 2011, 17:427-32.

Whitaker et al., "Bisphosphonates for osteoporosis—where do we go from here?," N Engl J Med, 2012, 366:2048-51.

Wise et al., "The effect of deafness duration on neurotrophin gene therapy for spiral ganglion neuron protection," Hearing Research, 2011, 278:69-76.

'www.sigmaadlrich.com' [online]. "Histone Deacetylase Inhibitors," dated on or before May 21, 2012 [retrieved on May 54, 2019]. Retrieved from the Internet: URL http://www.sigmaaldrich.com/life-science/molecular-biology/molecular-biology-products.html?TablePage=106211963, 2 pages.

Ylikoski et al., "Expression patterns of neurotrophin and their receptor mRNAs in the rat inner ear," Hearing Research, 1993, 65:69-78.

Yu et al., "Protection of spiral ganglion neurons from degeneration using smallmolecule TrkB receptor agonists," The Journal of Neuroscience, 2013, 33:13042-13052.

Zaccaro et al., "Selective Small Molecule Peptidomimetic Ligands of TrkC and TrkA Receptors Afford Discrete or Complete Neurotrophic Activities," Chemistry and Biology, 2005, 12:1015-1028.

Zhou et al., "Novel fluorescent risedronates: Synthesis, photodynamic inactivation and imaging of Bacillus subtilis," Bioorganic & Medicinal Chemistry Letters, 2013, 23: 949-954.

Zilberstein et al., "Inner hair cells are not required for survival of spiral ganglion neurons in the adult cochlea," The Journal of Neuroscience, 2012; 32:405-410.

Zou et al., "Communication between the perilymphatic scalae and spiral ligament visualized by in vivo MRI," Audiol Neurootol, 2005, 10:145-52.

\* cited by examiner

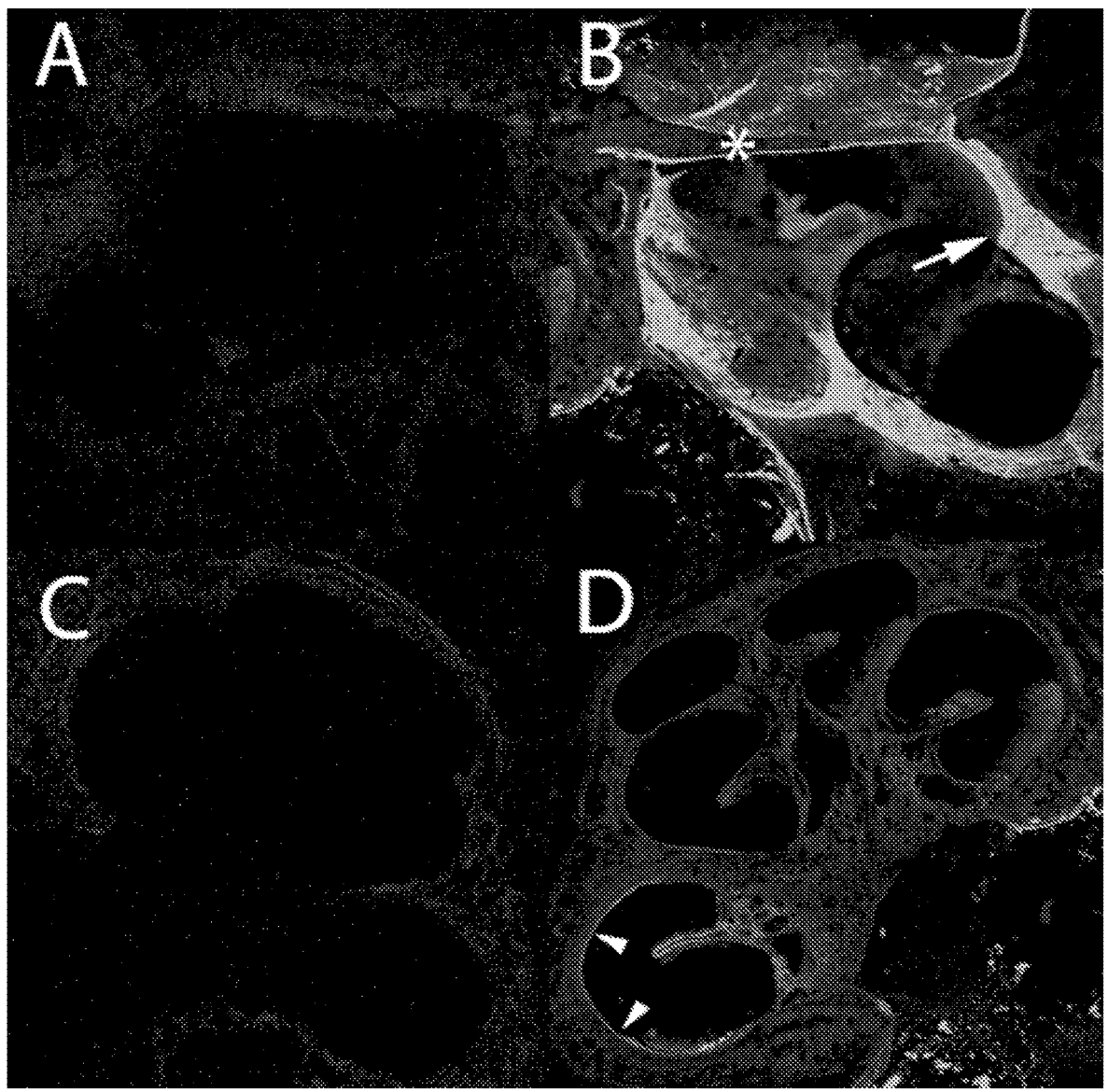
FIG. 12A-D

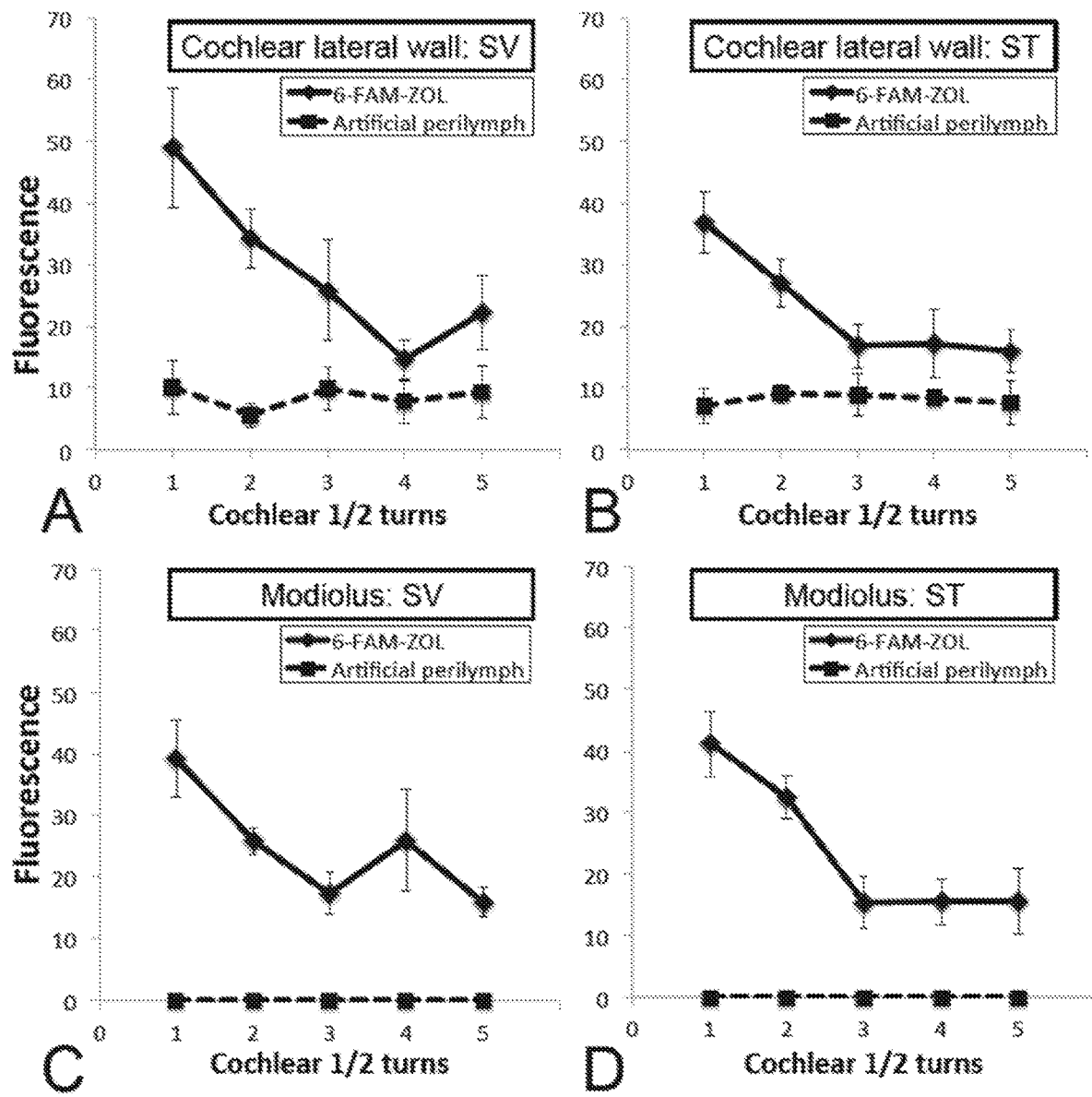
FIG. 13A-D

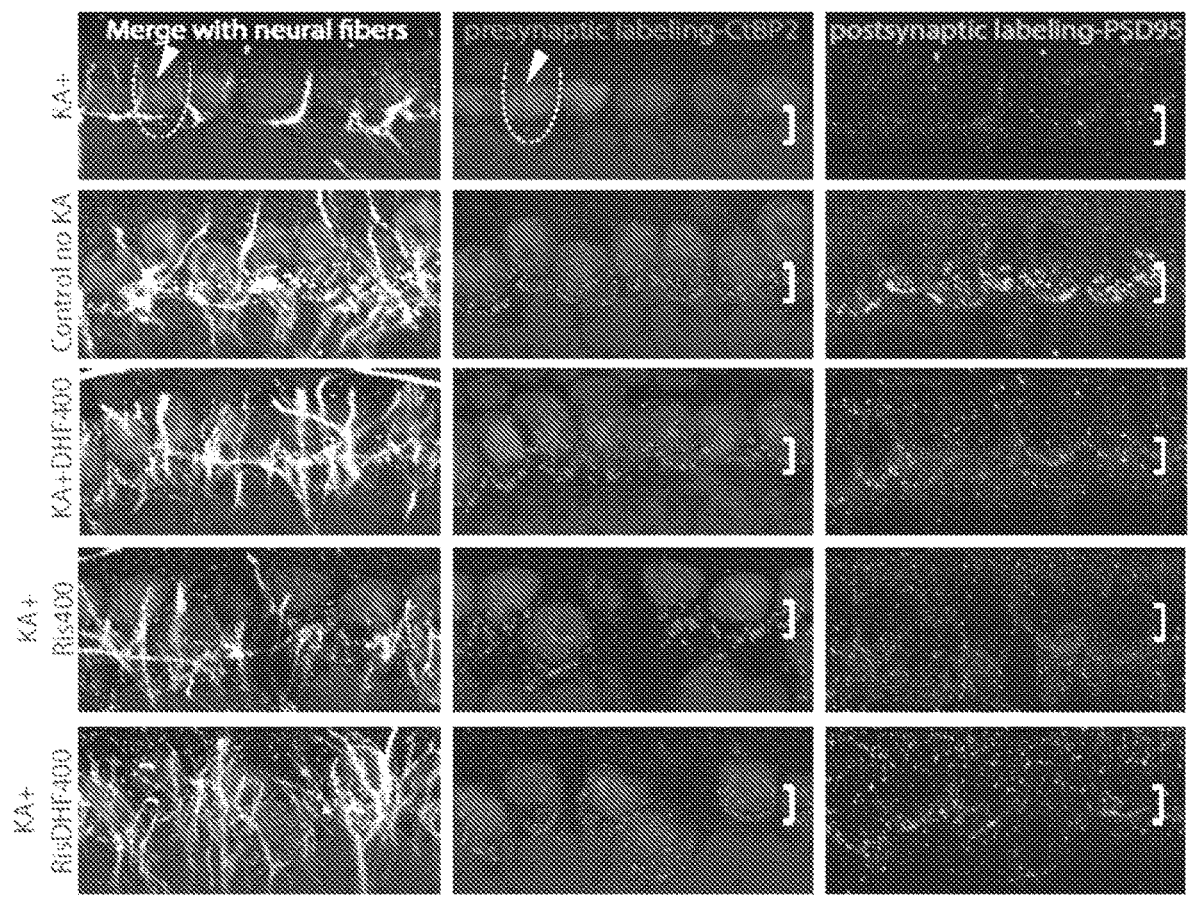
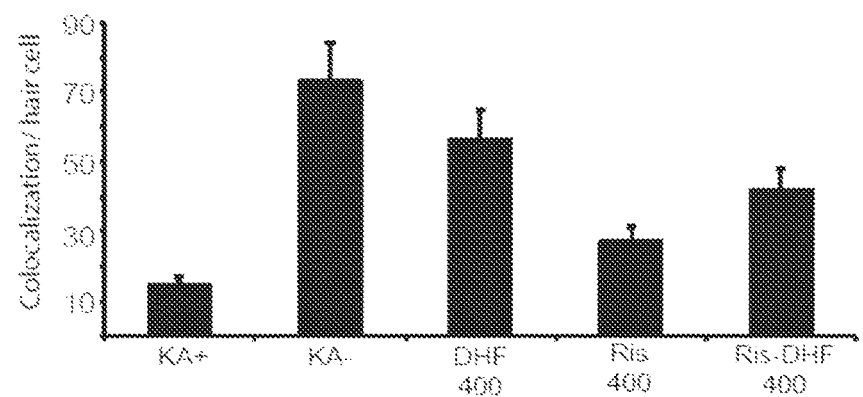
FIG. 14B

PHOSPHONATE-DRUG CONJUGATES

CROSS-REFERENCE TO RELATED APPLICATIONS

This application claims the benefit of U.S. Provisional Application Ser. No. 62/286,912, filed Jan. 25, 2016, the disclosure of which is incorporated herein by reference in its entirety.

STATEMENT OF FEDERALLY SPONSORED RESEARCH

This invention was made with government support under Grant Numbers DC015824, DC000038, and W81XWH-15-1-0472, awarded by the National Institutes of Health. The government has certain rights in the invention.

TECHNICAL FIELD

This invention relates to phosphonate conjugates that are useful for delivery of a drug to the middle and/or inner ear for treatment of a disease or disorder of the middle and/or inner ear.

BACKGROUND

Hearing aids and cochlear implants can significantly improve the quality of life for patients with hearing loss, although their performance remains limited. Improving spiral ganglion neuron (SGN) survival, neurite outgrowth, and synaptogenesis may therefore lead to significant gains both for deaf and hearing-impaired patients. Indeed, emerging evidence suggests that the loss of hair cells and neurons may underestimate the level of hearing impairment experienced by an individual, as noise damage may eliminate ribbon synapses while leaving hair cells and disconnected neurons in place. Since the middle and inner ear are encased within bone, bisphosphonates may provide an ideal vehicle with which to deliver drugs to the middle and inner ear.

SUMMARY

The present application provides, inter alia, a conjugate of Formula I:

$$B_p\text{-M-L-Z-D}$$

or a pharmaceutically acceptable salt thereof, wherein:
$B_p$ is a phosphonate moiety;
Z is NH or O;
M is a $C_{1-6}$ alkylamino group substituted by 1, 2, 3, or 4 $OR^C$ groups;
each $R^C$ is independently selected from the group consisting of H, $C_{1-6}$ alkyl, $C_{2-6}$ alkenyl, and $C_{2-6}$ alkynyl;
L is a linking group; and
D is a therapeutic agent.

In some embodiments, $B_p$ is a positively charged bisphosphonate moiety. In some embodiments, $B_p$ is a positively charged bisphosphonate moiety having the following formula:

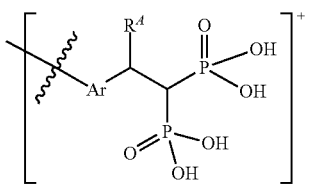

wherein:
∿∿ represents the location of the bond between $B_p$ and L;
$R^A$ is selected from the group consisting of H, halo, and OH; and
Ar is a 5-10 membered heteroaryl group.

In some embodiments, $R^A$ is selected from the group consisting of H, fluoro, chloro, and OH. In some embodiments, $R^A$ is H.

In some embodiments, Ar is selected from the group consisting of pyridinium, imidazolium, and imidazo[1,5-a]pyridinium. In some embodiments, Ar is selected from the group consisting of pyridinium and imidazolium.

In some embodiments, L is a hydrophobic linking group. In some embodiments, L is $C(O)R^B$, wherein $R^B$ is selected from the group consisting of $C_{1-10}$ alkylene, $C_{3-8}$ cycloalkylene, $C_{3-8}$ cycloalkylene-$C_{1-10}$ alkylene-, and $C_{1-10}$ alkylene-$C_{3-8}$ cycloalkylene-.

In some embodiments, $R^B$ is $C_{1-10}$ alkylene.

In some embodiments, L is a hydrophilic linking group. In some embodiments, L is —C(O)—($C_{1-4}$ alkylene)-$(CH_2CH_2O)_p$— and p is an integer from 1 to 10. In some embodiments, L is —C(O)—($CH_2CH_2$)—$(CH_2CH_2O)_p$— and p is an integer from 1 to 10.

In some embodiments, M is a $C_{1-6}$ alkylamino group substituted by 1 or 2 hydroxy groups. In some embodiments, M is a $C_{1-4}$ alkylamino group substituted by one hydroxy group. In some embodiments, M is —$CH_2CH(OH)CH_2NH$—.

In some embodiments, Z is NH. In some embodiments, Z is O.

In some embodiments, D is a therapeutic agent selected from the group consisting of a steroid, an antibiotic, a regenerative molecule, an epigenetic modifier, a chemotherapeutic agent, an immunotherapy agent, a single gene target, and an ion regulator.

In some embodiments, D is a steroid. In some embodiments, D is a steroid selected from the group consisting of cortisone, dexamethasone, hydrocortisone, methylprednisolone, prednisolone, and prednisone.

In some embodiments, D is an antibiotic. In some embodiments, D is an antibiotic selected from the group consisting of a cephalosporin, a carapenem, a monobactam, an aminoglycoside, a glycopeptide, an oxazolidinone, a lincosamide, a macrolide, a penicilin, a quinolone, a sulfonamide, and a tetracycline.

In some embodiments, D is a hair cell regenerative molecule. In some embodiments, D is a hair cell regenerative molecule selected from the group consisting of a gamma-secretase inhibitor, a Notch activator, a Wnt related small molecule, and a Sox2 activator.

In some embodiments, D is a neuron cell regenerative molecule. In some embodiments, D is a neuron cell regenerative molecule selected from the group consisting of a BDNF small molecule mimic, a neurotrophin-3 small molecule mimic, and a Sox2 inhibitor.

In some embodiments, D is an epigenetic modifier. In some embodiments, D is an epigenetic modifier selected from the group consisting of a DNA methyl transferase, a methyl-CpG-binding protein (MBP), a histone methyltransferase (HMT), a histone demethylase (HDM), a histone acetyltransferase (HAT), and a histone deacetylase (HDAC).

In some embodiments, D is a chemotherapeutic agent. In some embodiments, D is a chemotherapeutic agent selected from the group consisting of an alkylating agent, an antimetabolite, an anti-tumor antibiotic, a topoisomerase inhibitor, a mitotic inhibitor, and a hormone receptor inhibitor.

In some embodiments, D is an immunotherapy agent. In some embodiments, D is an immunotherapy agent selected from the group consisting of a cancer vaccine, a checkpoint inhibitor, and a monoclonal antibody.

In some embodiments, D is a single gene target. In some embodiments, D is a single gene target consisting of a CRISPR/Cas system.

In some embodiments, D is an ion regulator. In some embodiments, D is an ion regulator which is a calcium channel blocker.

In some embodiments, the conjugate of Formula I is a conjugate of Formula II:

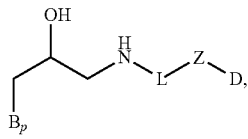

or a pharmaceutically acceptable salt thereof.

In some embodiments, conjugate of Formula I is a conjugate of Formula III:

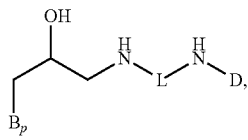

or a pharmaceutically acceptable salt thereof.

In some embodiments, the conjugate of Formula I is a conjugate of Formula IV:

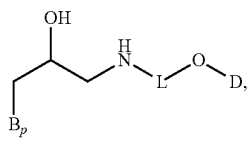

or a pharmaceutically acceptable salt thereof.

In some embodiments, the conjugate of Formula I is a conjugate of Formula V:

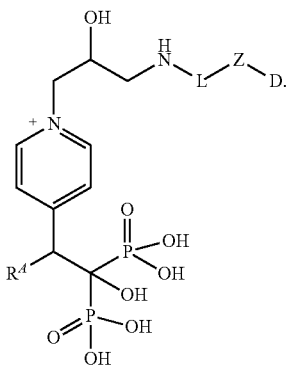

In some embodiments, the conjugate of Formula I is a conjugate of Formula VI:

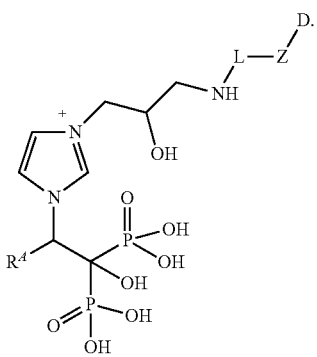

In some embodiments, the conjugate of Formula I is a conjugate of Formula VII:

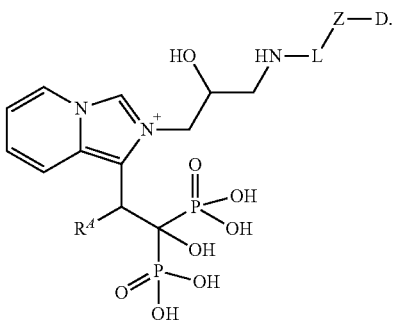

In some embodiments, the conjugate is selected from the group consisting of:

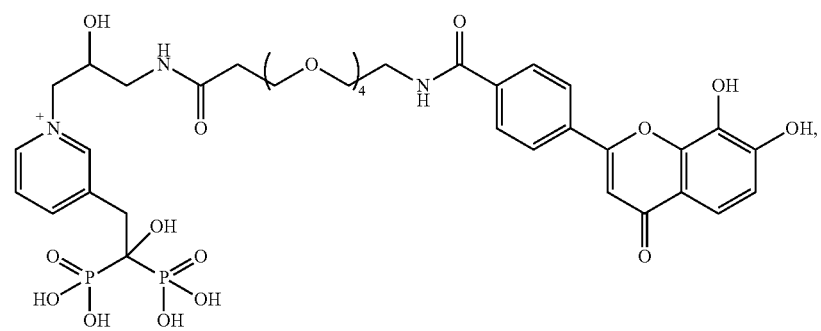

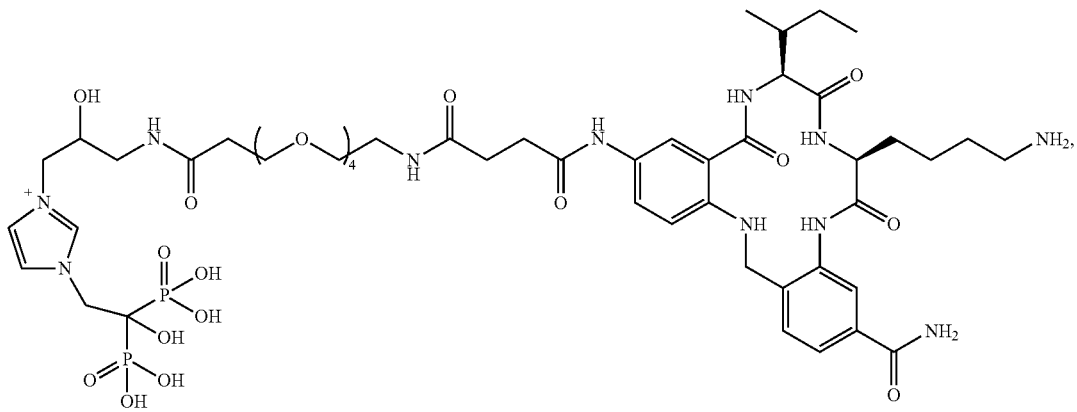
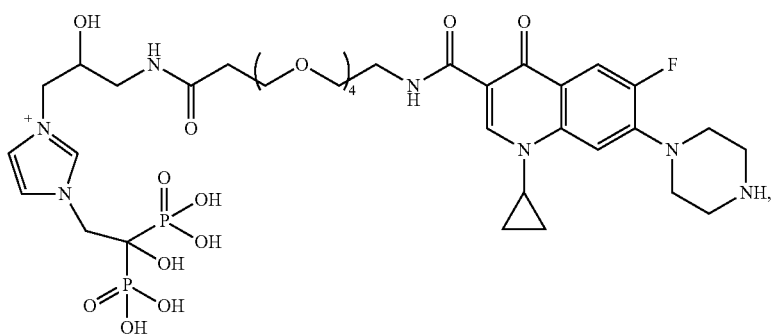
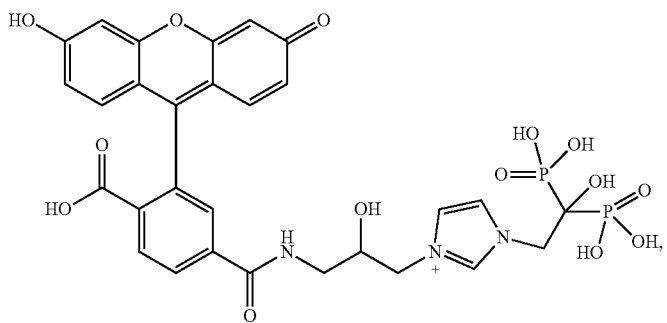
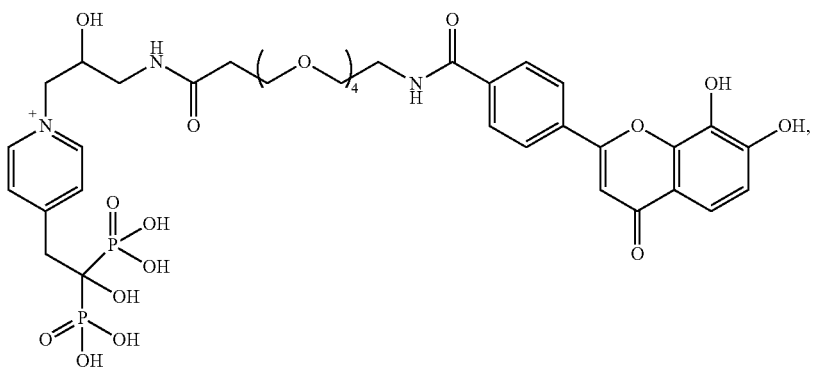

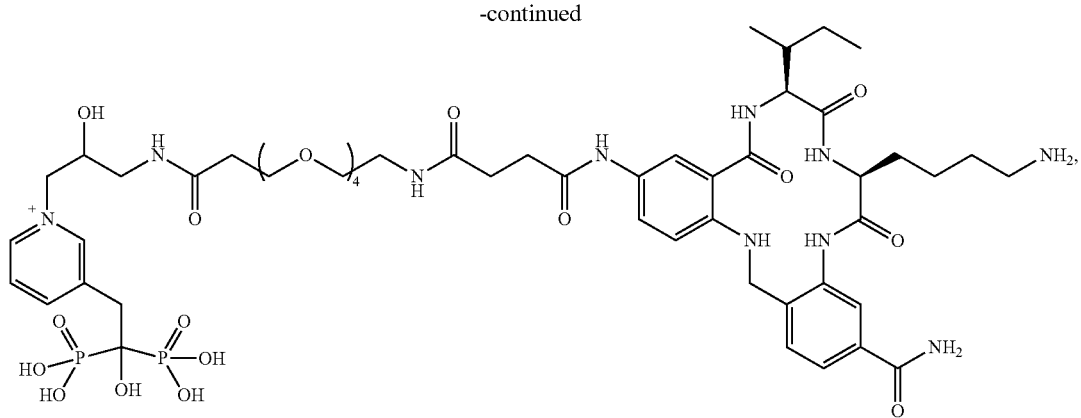
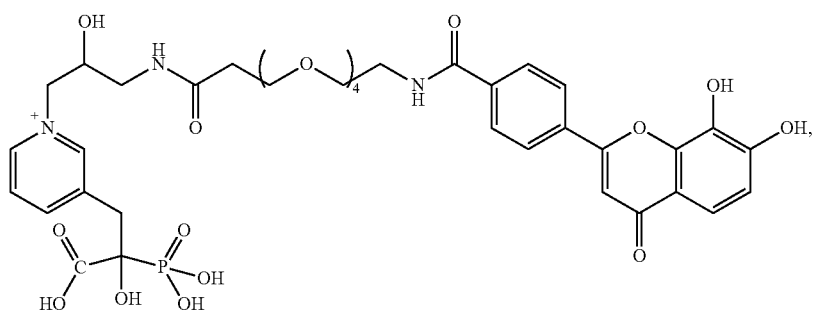
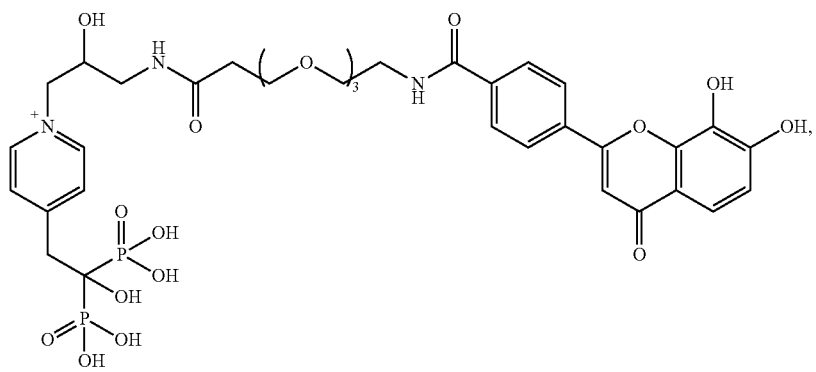
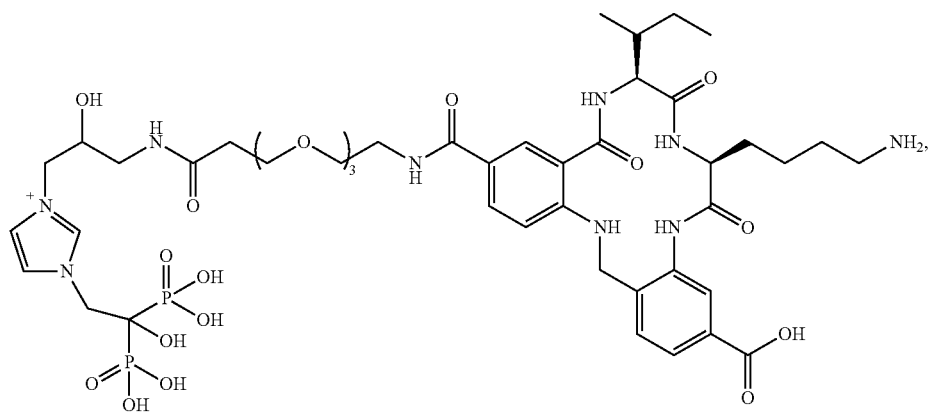

-continued
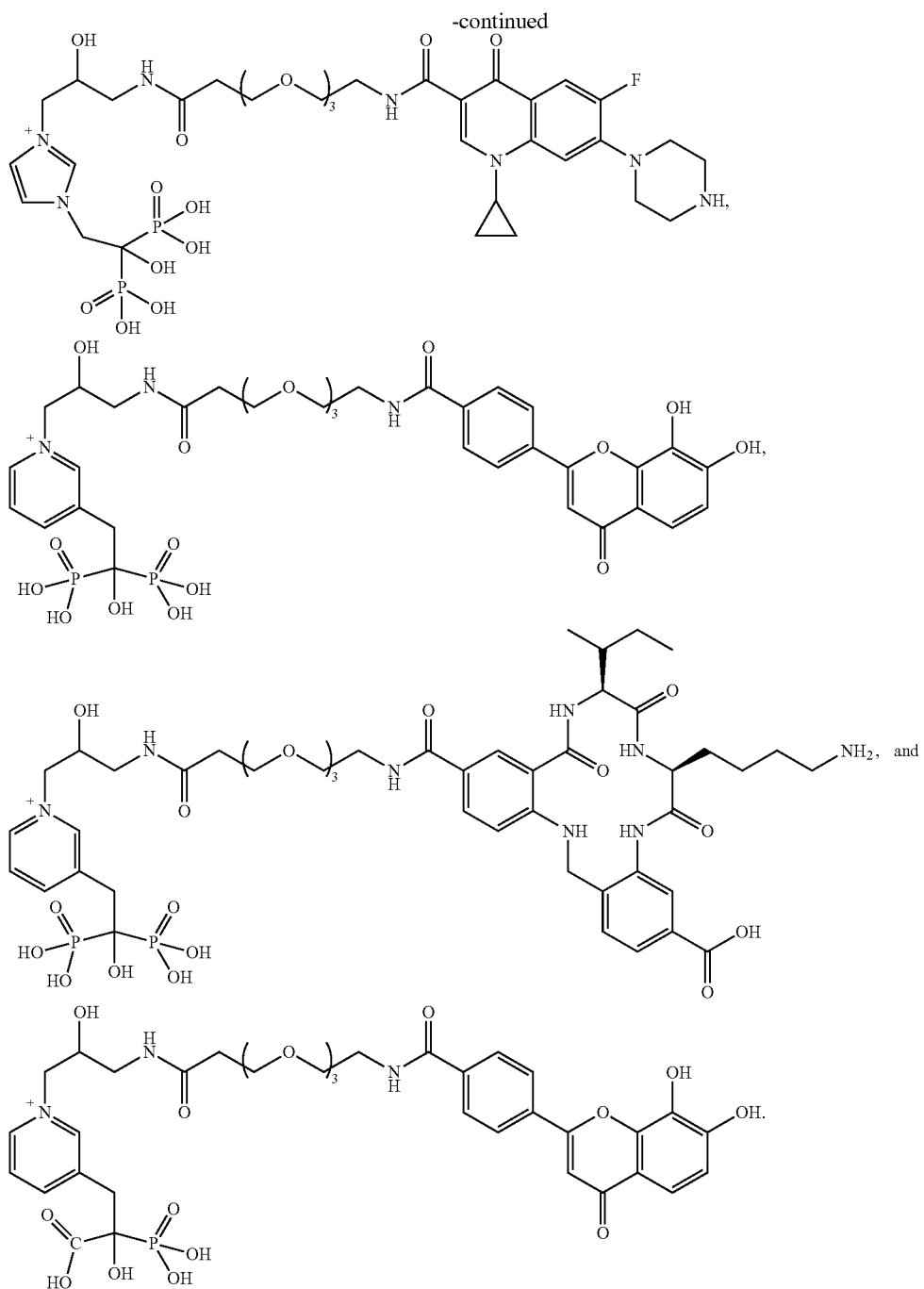
In some embodiments, the conjugate is selected from the group consisting of:
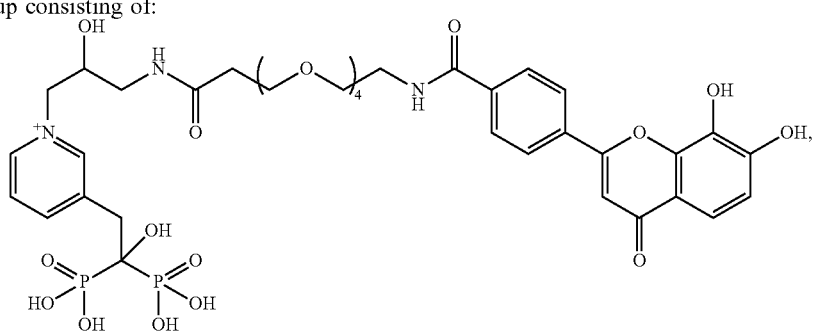

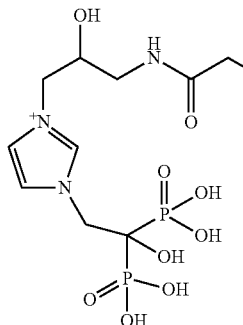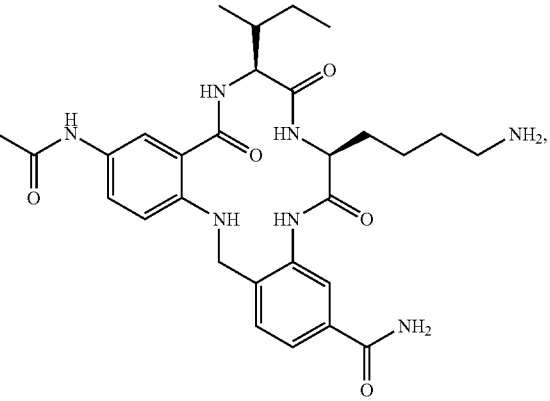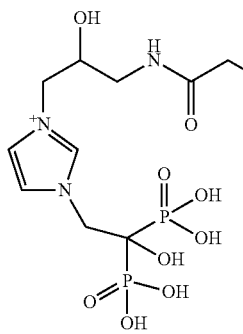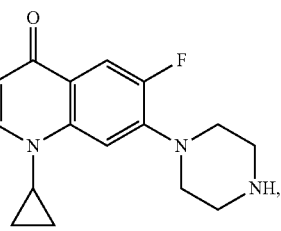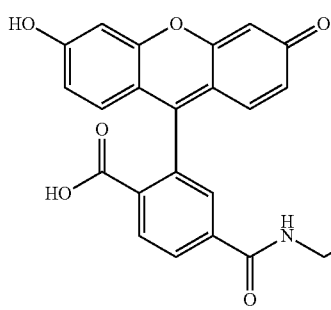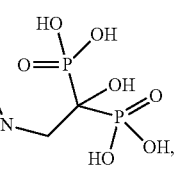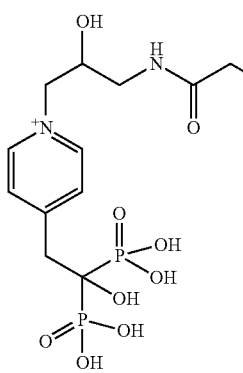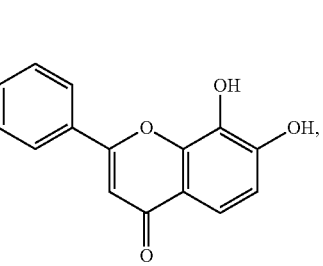

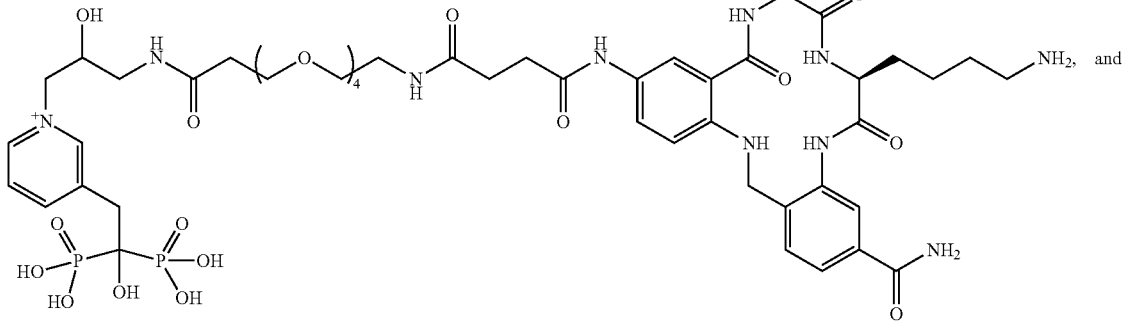
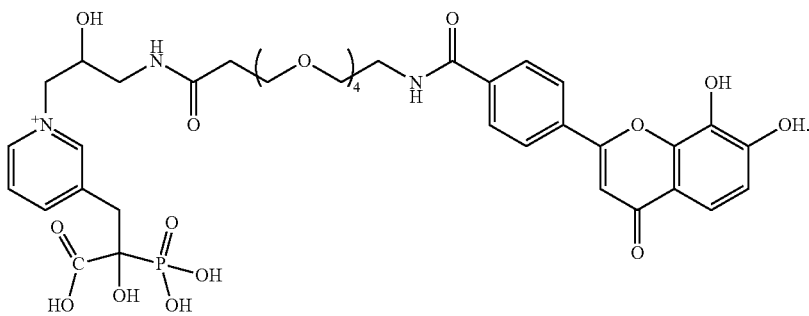
In some embodiments, the conjugate is selected from the group consisting of:
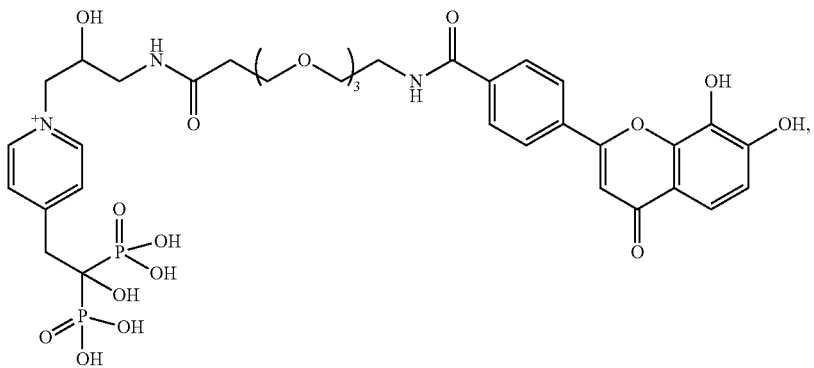
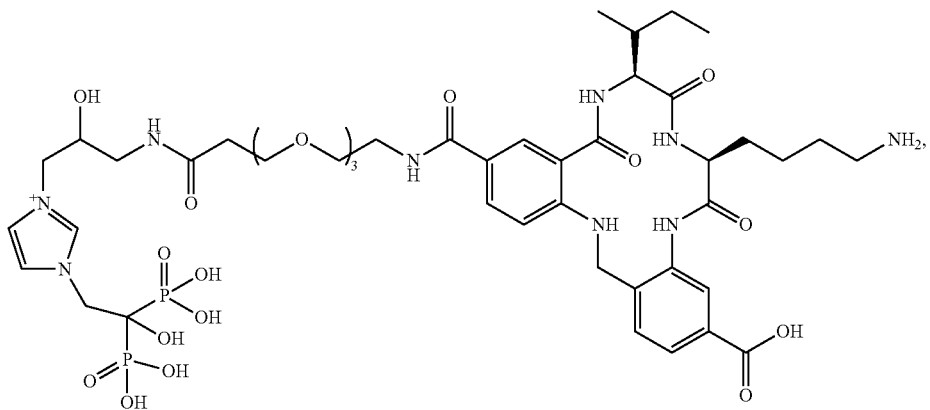

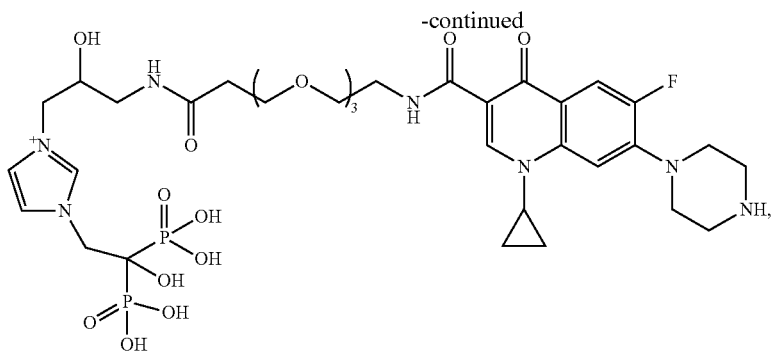

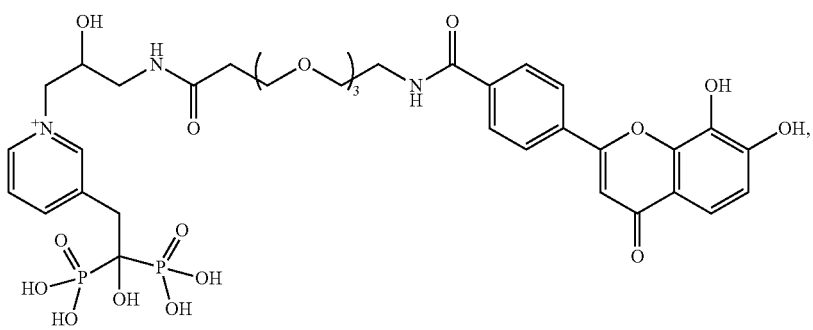

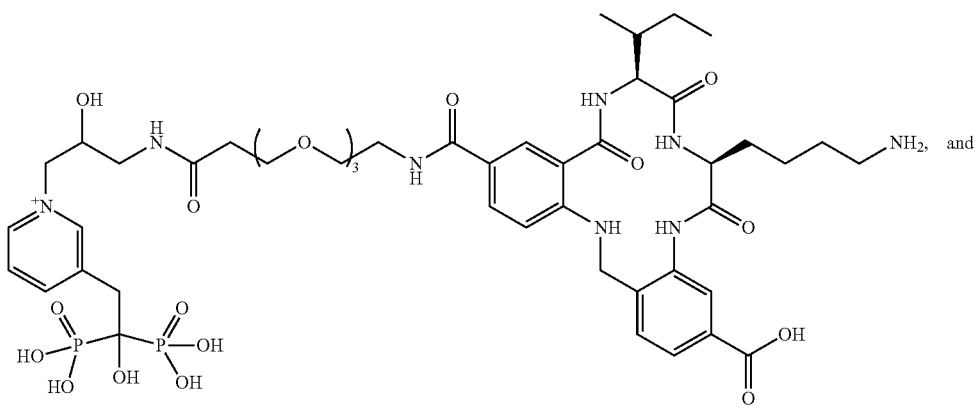

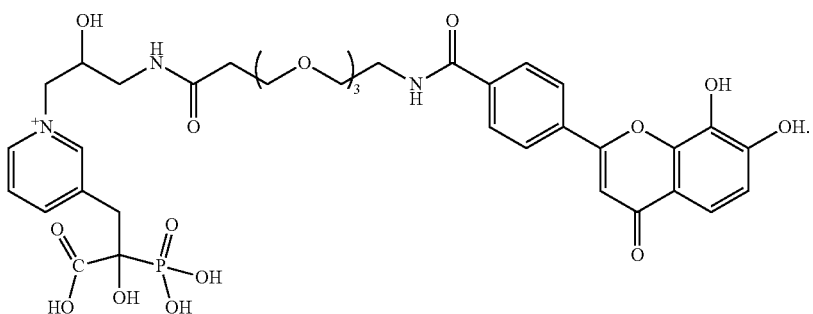

The present application further provides a method of treating a disease or disorder of the middle ear and/or inner ear in a subject, comprising administering to the subject a therapeutically effective amount of a conjugate provided herein, or a pharmaceutically acceptable salt thereof.

In some embodiments, the administering is localized at the round window membrane.

In some embodiments, the disease or disorder is associated with abnormal activity or dysregulation of spiral ganglion neuron cells. In some embodiments, the disease or disorder is associated with abnormal activity or dysregulation of one or more Tropomyosin receptor kinases. In some embodiments, the Tropomyosin receptor kinase is TrkB or TrkC.

In some embodiments, the disease or disorder of the middle ear and/or inner ear is selected from the group consisting of vestibular schwannoma, hearing loss, otitis media, cancer of the middle ear and/or inner ear, Meniere's disease, osteoporosis, Paget's disease, osteogenesis, osteomyelitis, otosclerosis, an autoimmune middle ear and/or inner ear disease, benign paroxysmal positional vertigo (BPPV), bilateral vestibular hypofunction, labyrinthitis, vestibular neuritis, secondary endolymphatic hydrops (SEH), tinnitus, vestibular hyperacusis, and vertebrobasilar insufficiency (VBI). In some embodiments, the autoimmune middle ear and/or inner ear disease is selected from the group consisting of Cogan's syndrome, relapsing polychondritis, polyarteritis *nodosa*, Wegener's granulomatosis, systemic lupus erythematosus, ulcerative colitis, Sjogren's syndrome, and rheumatoid arthritis. In some embodiments, the hearing loss comprises sudden sensorineural hearing, autoimmune hearing loss, or noise-induced hearing loss. In some embodiments, the otitis media is acute otitis media (AOM) or otitis media with effusion (OME). In some embodiments, the cancer of the middle ear and/or inner ear is selected from the group consisting of squamous cell carcinoma, basal cell cancer, melanoma, adenoid cystic carcinoma, and adenocarcimona.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DESCRIPTION OF DRAWINGS

FIG. 12A shows confocal images taken at mid-modiolar cochlear sections for the vestibule of a human cochlea treated with artificial perilymph alone.

FIG. 12B shows confocal images taken at mid-modiolar cochlear sections for the vestibule of a human cochlea treated with 6-FAM-ZOL. The asterisk indicates the stapes footplate and the arrow indicates the lateral wall of the vestibule.

FIG. 12C shows confocal images taken at mid-modiolar cochlear sections for a human cochlea treated with artificial perilymph alone.

FIG. 12D shows confocal images taken at mid-modiolar cochlear sections for a human cochlea treated with 6-FAM-ZOL. The arrowhead indicates the lateral wall of the basal cochlear turn.

FIG. 13A shows quantification of 6-FAM-ZOL following intracochlear administration in a human bone model. Using ImageJ, measurements were taken at each of five cochlear half-turns from base to apex in the human temporal bone specimens, along both the lateral cochlear wall. The p values for the effect of 6-FAM-ZOL are 0.04 in the SV (scala vestibule).

FIG. 13B shows quantification of 6-FAM-ZOL following intracochlear administration in a human bone model. Using ImageJ, measurements were taken at each of five cochlear half-turns from base to apex in the human temporal bone specimens, along both the lateral cochlear wall. The p values for the effect of 6-FAM-ZOL 0.03 in the ST (scala tympani).

FIG. 13C shows quantification of 6-FAM-ZOL following intracochlear administration in a human bone model. Using ImageJ, measurements were taken at each of five cochlear half-turns from base to apex in the human temporal bone specimens, along the modiolus. The p values for the effect of 6-FAM-ZOL are 0.001 in the SV (scala vestibule).

FIG. 13D shows quantification of 6-FAM-ZOL following intracochlear administration in a human bone model. Using ImageJ, measurements were taken at each of five cochlear half-turns from base to apex in the human temporal bone specimens, along the modiolus. The p values for the effect of 6-FAM-ZOL are 0.002 in the ST (scala tympani).

FIG. 14B shows regeneration of ribbon synapses after KA treatment. CtBP2 marks the presynaptic area of the inner hair cell, while PSD95 marks the postsynaptic area of the neuron; synapses are defined as overlapping dots. Neurofilament (NF) marks all neurons. The graph shows quantification of synapses.

DETAILED DESCRIPTION

Figure 1:
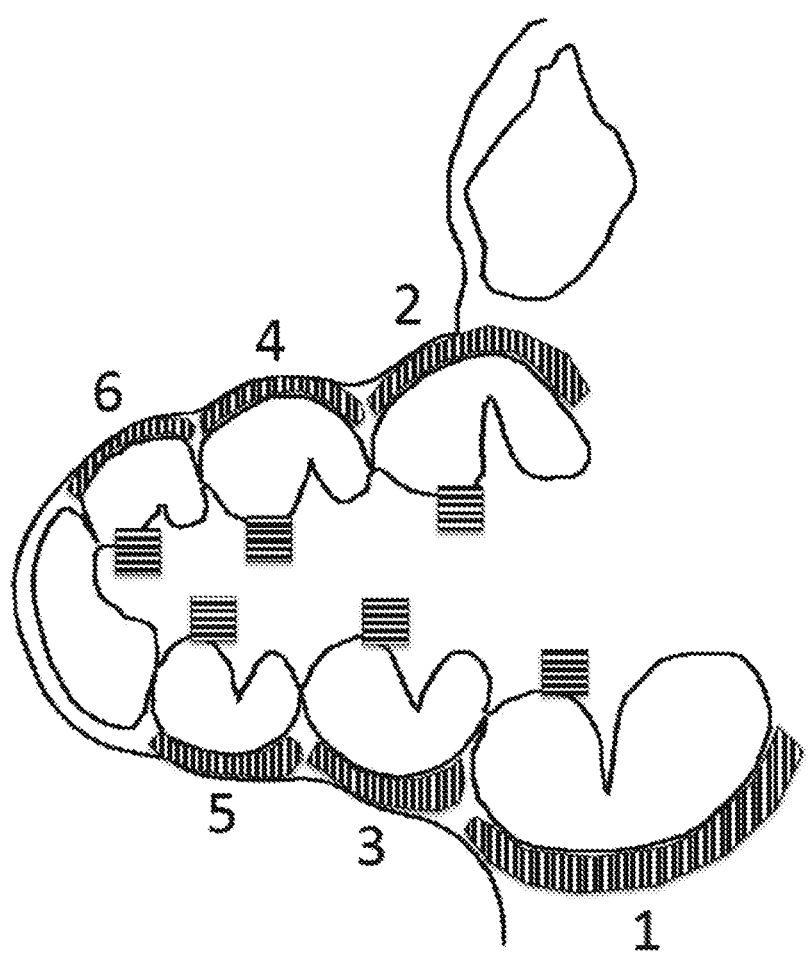
FIG. 1 shows a schematic of a guinea pig cochlea taken at a mid-modiolar section. Shaded areas of the modiolus and lateral cochlear wall at each half-turn were measured for average fluorescence.

Current drug delivery methods to the inner ear include diffusion across the round window membrane (RWM), direct infusion via cochleostomy, or systemic delivery (see e.g., Swan et al., *Advanced Drug Delivery Reviews*, 2008, 60:1583-1599). RWM delivery using intratympanic injection of solutions is in common clinical practice (see e.g., Rauch et al., *Jama* 2011, 305:2071-2079) and use of a hydrogel to improve RWM delivery is in human clinical trials (see e.g., Wang et al., Official Publication of the American Otological Society, American Neurotology Society [and] European Academy of Otology and Neurotology, 2014, 35:459-469).

Although the previous studies utilizing viral vectors and osmotic pumps have shown some benefit in neuronal survival following deafening, several aspects of those approaches render them problematic for application to clinical practice. For example, an osmotic pump presents significant engineering challenges and requires placement of a cochleostomy with high risk to acoustical hearing. In addition, since the required length of treatment to promote SGN survival, neurite outgrowth, and synaptogenesis remains unclear, there may be a need to refill or replace the pump, which in patients could require additional surgery. Viral vectors trophic for supporting cells potentially represents an effective method of delivering therapeutic neurotrophins, but current technology is associated with very low rates of infection limited to the basal turn and modest results (see e.g., Wise et al., *Hearing Research*, 2011, 278:69-76).

The present application provides phosphonate-drug conjugates that are useful for localized delivery of the drug across the RWM for the treatment of diseases and disorders of the middle ear and/or inner ear. The present application further provides fluorescently-labeled bisphosphonate conjugates used to quantify the increased efficiency of RWM delivery and infusion via a cochleostomy. For a given systemic dose, 30% delivered across the RWM and 2% delivered through direct infusion delivered an equivalent dose to the cochlea (see e.g., Kang et al., Official Publication of the American Otological Society, American Neurotology Society [and] European Academy of Otology and Neurotology 2015; 36:953-960). Local delivery methods therefore maximize local concentration while minimizing systemic effects.

Conjugates

The present application provides inter alia, a conjugate of Formula I:

$B_p$-M-L-Z-D or a pharmaceutically acceptable salt thereof, wherein:

$B_p$ is a phosphonate moiety;

Z is NH or O;

M is a $C_{1-6}$ alkylamino group substituted by 1, 2, 3, or 4 $OR^C$ groups;

each $R^C$ is independently selected from the group consisting of H, $C_{1-6}$ alkyl, $C_{2-6}$ alkenyl, and $C_{2-6}$ alkynyl;

L is a linking group; and

D is a therapeutic agent.

Phosphonate Moiety

In some embodiments, $B_p$ is a monophosphonate moiety. In some embodiments, $B_p$ is a positively charged monophosphonate moiety. In some embodiments, $B_p$ is a positively charged monophosphonate moiety having the following formula:

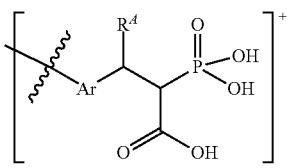

wherein:

∿∿∿ represents the location of the bond between $B_p$ and L;

$R^A$ is selected from the group consisting of H, halo, and OH;

Ar is a 5-10 membered heteroaryl group.

In some embodiments, $B_p$ is a bisphosphonate moiety. In some embodiments, $B_p$ is a positively charged bisphosphonate moiety. In some embodiments, $B_p$ is a positively charged bisphosphonate moiety having the following formula:

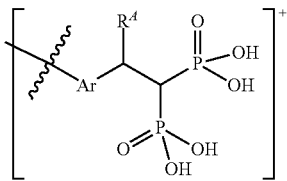

wherein:

∿∿∿ represents the location of the bond between $B_p$ and L;

$R^A$ is selected from the group consisting of H, halo, and OH;

Ar is a 5-10 membered heteroaryl group.

In some embodiments, $B_p$ is selected from the group consisting of:

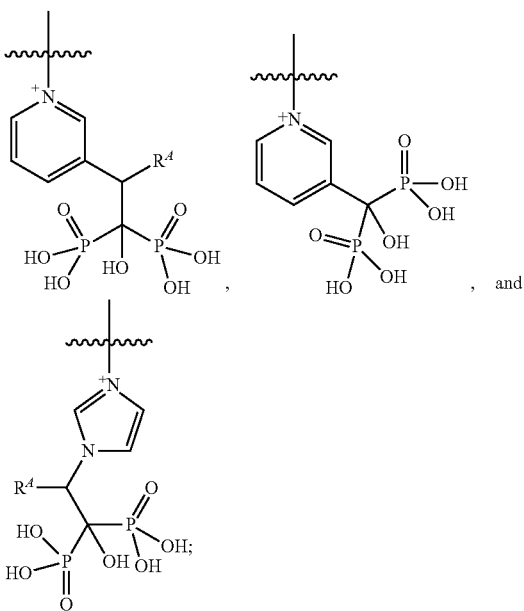

wherein ∿∿∿ represents the location of the bond between $B_p$ and L.

In some embodiments, $R^A$ is selected from the group consisting of H, fluoro, chloro, and OH. In some embodiments, $R^A$ is H. In some embodiments, $R^A$ is halo. In some embodiments, $R^A$ is fluoro or chloro. In some embodiments, $R^A$ is fluoro. In some embodiments, $R^A$ is chloro. In some embodiments, $R^A$ is OH.

In some embodiments, Ar is a positively charged 5-10 membered heteroaryl group. In some embodiments, Ar is a positively charged 5-10 membered heteroaryl group, wherein the heteroaryl group has 1, 2, or 3 heteroatom ring members selected from sulfur, oxygen, and nitrogen. In some embodiments, Ar is a positively charged 5-10 membered heteroaryl group, wherein the heteroaryl group has 1 or 2 nitrogen ring members. In some embodiments, Ar is a positively charged 5-6 membered heteroaryl group. In some embodiments, Ar is a positively charged 5-6 membered heteroaryl group, wherein the heteroaryl group has 1, 2, or 3 heteroatom ring members selected from sulfur, oxygen, and nitrogen. In some embodiments, Ar is a positively charged 5-6 membered heteroaryl group, wherein the heteroaryl group has 1 or 2 nitrogen ring members. In some embodiments, Ar is selected from the group consisting of pyridinium, imidazolium, and imidazo[1,5-a]pyridinium. In some embodiments, Ar is selected from the group consisting of pyridinium and imidazolium. In some embodiments, Ar is imidazo[1,5-a]pyridinium. In some embodiments, Ar is pyridinium. In some embodiments, Ar is imidazolium.

Linkers

In some embodiments, L is a hydrophobic linking group. In some embodiments, L is a hydrophobic linking group comprising 1 to 20 carbon atoms, for example, 1 to 20 carbon atoms, 1 to 15 carbon atoms, 1 to 10 carbon atoms, 1 to 8 carbon atoms, 1 to 6 carbon atoms, 1 to 4 carbon atoms, 1 to 2 carbon atoms, 2 to 20 carbon atoms, 2 to 15 carbon atoms, 2 to 10 carbon atoms, 2 to 8 carbon atoms, 2 to 6 carbon atoms, 2 to 4 carbon atoms, 4 to 20 carbon atoms, 4 to 15 carbon atoms, 4 to 10 carbon atoms, 4 to 8 carbon atoms, 4 to 6 carbon atoms, 6 to 20 carbon atoms, 6 to 15 carbon atoms, 6 to 10 carbon atoms, 6 to 8 carbon atoms, 8 to 20 carbon atoms, 8 to 15 carbon atoms, 8 to 10 carbon atoms, 10 to 20 carbon atoms, 10 to 15 carbon atoms, or 15 to 20 carbon atoms. In some embodiments, L is a hydrophobic linking group comprising one carbonyl group and one or more alkylene groups, or one or more alkenylene groups, or one or more alkynylene groups, or any combination thereof.

In some embodiments, L is $C(O)R^B$, wherein $R^B$ is selected from the group consisting of $C_{1-20}$ alkylene, $C_{2-20}$ alkenylene, $C_{2-20}$ alkynylene, $C_{3-20}$ cycloalkylene, $C_{3-20}$ cycloalkylene-$C_{1-20}$ alkylene, $C_{3-20}$ cycloalkylene-$C_{2-20}$ alkenylene, and $C_{3-20}$ cycloalkylene-$C_{2-20}$ alkynylene. In some embodiments, $R^B$ is selected from the group consisting of $C_{1-8}$ alkylene, $C_{3-8}$ cycloalkylene, $C_{3-8}$ cycloalkylene-$C_{1-8}$ alkylene-, or $C_{1-8}$ alkylene-$C_{3-8}$ cycloalkylene-. In some embodiments, L is $C(O)R^B$, wherein $R^B$ is selected from the group consisting of $C_{1-20}$ alkylene, $C_{3-20}$ cycloalkylene, $C_{3-20}$ cycloalkylene-$C_{1-20}$ alkylene-, or $C_{1-20}$ alkylene-$C_{3-20}$ cycloalkylene-.

In some embodiments, $R^B$ is selected from the group consisting of $C_{1-8}$ alkylene, $C_{3-8}$ cycloalkylene, $C_{3-8}$ cycloalkylene-$C_{1-8}$ alkylene-, or $C_{1-8}$ alkylene-$C_{3-8}$ cycloalkylene-. In some embodiments $R^B$ is selected from the group consisting of $C_{1-8}$ alkylene and $C_{3-8}$ cycloalkylene. In some embodiments, $R^B$ is $C_{1-8}$ alkylene. In some embodiments $R^B$ is $C_{3-8}$ cycloalkylene.

In some embodiments, L is a hydrophilic linking group. In some embodiments, L is a hydrophilic linking group comprising one or more alkyleneoxy groups. In some embodiments, L is a hydrophilic linking group comprising one carbonyl group and one or more alkyleneoxy groups.

In some embodiments, L is a hydrophilic linking group comprising 1 to 3000 alkyleneoxy groups, for example, 1 to 3000, 1 to 2500, 1 to 2000, 1 to 1500, 1 to 1000, 1 to 500, 1 to 250, 1 to 100, 1 to 50, 1 to 20, 1 to 10, 1 to 5, 5 to 3000, 5 to 2500, 5 to 2000, 5 to 1500, 5 to 1000, 5 to 500, 5 to 250, 5 to 100, 5 to 50, 5 to 20, 5 to 10, 10 to 3000, 10 to 2500, 10 to 2000, 10 to 1500, 10 to 1000, 10 to 500, 10 to 250, 10 to 100, 10 to 50, 10 to 20, 20 to 3000, 20 to 2500, 20 to 2000, 20 to 1500, 20 to 1000, 20 to 500, 20 to 250, 20 to 100, 20 to 50, 50 to 3000, 50 to 2500, 50 to 2000, 50 to 1500, 50 to 1000, 50 to 500, 50 to 250, 50 to 100, 100 to 3000, 100 to 2500, 100 to 2000, 100 to 1500, 100 to 1000, 100 to 500, 100 to 250, 250 to 3000, 250 to 2500, 250 to 2000, 250 to 1500, 250 to 1000, 250 to 500, 500 to 3000, 500 to 2500, 500 to 2000, 500 to 1500, 500 to 1000, 1000 to 3000, 1000 to 2500, 1000 to 2000, 1000 to 1500, 1500 to 3000, 1500 to 2500, 1500 to 2000, 2000 to 3000, 2000 to 2500, or 2500 to 3000 alkyleneoxy groups.

In some embodiments, each of the one or more alkyleneoxy groups is independently a group having the formula -(alkylene-O)—. In some embodiments, each of the one or more alkyleneoxy groups is independently a group having formula —($C_{1-6}$ alkylene-O)—. In some embodiments, each of the one or more alkyleneoxy groups is a group having formula —($CH_2CH_2O$)— or —($CH_2O$)—. In some embodiments, L is —C(O)—($CH_2CH_2O$)$_p$— and p is an integer from 1 to 3000. In some embodiments, L is —C(O)—($CH_2CH_2O$)$_p$— and p is an integer from 1 to 10. In some embodiments, p is an integer from 1 to 2500. In some embodiments, p is an integer from 1 to 2000. In some embodiments, p is an integer from 1 to 2000. In some embodiments, p is an integer from 1 to 1500. In some embodiments, p is an integer from 1 to 1000. In some embodiments, p is an integer from 1 to 750. In some embodiments, p is an integer from 1 to 500. In some embodiments, p is an integer from 1 to 250. In some embodiments, p is an integer from 1 to 100. In some embodiments, p is an integer from 1 to 50. In some embodiments, p is an integer from 1 to 25. In some embodiments, p is an integer from 1 to 10. In some embodiments, p is an integer from 1 to 5.

In some embodiments, M is a $C_{1-6}$ alkylamino group substituted by 1, 2, 3, or 4 OR$^C$ groups, wherein each R$^C$ is independently selected from the group consisting of H and $C_{1-6}$ alkyl. In some embodiments, M is a $C_{1-6}$ alkylamino group substituted by 1 or 2 OR$^C$ groups, wherein each R$^C$ is independently selected from the group consisting of H and $C_{1-6}$ alkyl. In some embodiments, M is a $C_{1-6}$ alkylamino group substituted by 1 or 2 hydroxy groups. In some embodiments, M is a $C_{1-4}$ alkylamino group substituted by one hydroxyl group. In some embodiments, M is —$CH_2CH(OH)CH_2NH$—.

In some embodiments, Z is NH. In some embodiments, Z is O.

Therapeutic Agents

In some embodiments, D is a therapeutic agent selected from the group consisting of a steroid, an antibiotic, a regenerative molecule, an epigenetic modifier, a chemotherapy agent, an immunotherapy agent, a single gene target, an ion regulator, and a microglial inhibitor. In some embodiments, D is a therapeutic agent selected from the group consisting of a steroid, an antibiotic, a regenerative molecule, an epigenetic modifier, a chemotherapeutic agent, an immunotherapy agent, a single gene target, and an ion regulator.

In some embodiments, D is a steroid. Example steroids include, but are not limited to, corticosteroids. In some embodiments, the steroid is a corticosteroid. In some embodiments, the steroid is selected from the group consisting of cortisone, dexamethasone, hydrocortisone, methylprednisolone, prednisolone, prednisone.

In some embodiments, D is an antibiotic. Example antibiotics include, but are not limited to, cephalosporins (e.g., first, second, third, fourth, or fifth generation cephalosporins), carapenems, monobactams, aminoglycosides, glycopeptides, oxazolidinones, lincosamides, macrolides, penicilins, quinolones, sulfonamides, and tetracyclines.

In some embodiments the antibiotic is selected from the group consisting of a first generation cephalosporin, a second generation cephalosporin, a third generation cephalosporin, a fourth generation cephalosporin, a fifth generation cephalosporin, a carapenem, a monobactam, an aminoglycoside, a glycopeptide, an oxazolidinone, a lincosamide, a macrolide, a penicilin, a quinolone, a sulfonamide, and a tetracycline.

In some embodiments, the antibiotic is a first generation cephalosporin. In some embodiments, the antibiotic is a first generation cephalosporin selected from the group consisting of cefacetrile (i.e., cephacetrile), cefadroxil (i.e., cefadroxyl), cefalexin (i.e., cephalexin), cefaloglycin (i.e., cephaloglycin), cefalonium (i.e., cephalonium), cefaloridine (i.e., cephaloradine), cefalotin (i.e., cephalothin), cefapirin (i.e., cephapirin), cefatrizine, cefazaflur, cefazedone, cefazolin (i.e., cephazolin), cefradine (i.e., cephradine), cefroxadine, and ceftezole.

In some embodiments, the antibiotic is a second generation cephalosporin. In some embodiments, the antibiotic is a second generation cephalosporin selected from the group consisting of cefaclor, cefamandole, cefmetazole, cefonicid, cefotetan, cefoxitin, cefprozil (i.e., cefproxil), cefuroxime, and cefuzonam.

In some embodiments, the antibiotic is a third generation cephalosporin. In some embodiments, the antibiotic is a third generation cephalosporin selected from the group consisting of cefcapene, cefdaloxime, cefdinir, cefditoren, cefetamet, cefixime, cefmenoxime, cefodizime, cefotaxime, cefpimizole, cefpodoxime, cefteram, ceftibuten, ceftiofur, ceftiolene, ceftizoxime, ceftriaxone, cefoperazone, and ceftazidime.

In some embodiments, the antibiotic is a fourth generation cephalosporin. In some embodiments, the antibiotic is a fourth generation cephalosporin selected from the group consisting of cefclidine, cefepime, cefluprenam, cefoselis, cefozopran, cefpirome, cefquinome.

In some embodiments, the antibiotic is a fifth generation cephalosporin. In some embodiments, the antibiotic is a fifth generation cephalosporin selected from the group consisting of ceftobiprole and ceftaroline.

In some embodiments, the antibiotic is a carapenem. In some embodiments, the antibiotic is a carapenem selected from the group consisting of ertapenem, meropenem, and imipenem.

In some embodiments, the antibiotic is a monobactam. In some embodiments, the antibiotic is a monobactam which is aztreonam.

In some embodiments, the antibiotic is an aminoglycoside. In some embodiments, the antibiotic is an aminoglycoside selected from the group consisting of amikacin, gentamicin, and tobramycin.

In some embodiments, the antibiotic is a glycopeptide. In some embodiments, the antibiotic is a glycopeptide which is vancomycin.

In some embodiments, the antibiotic is an oxazolidinone. In some embodiments, the antibiotic is an oxazolidinone which is linezolid.

In some embodiments, the antibiotic is a lincosamide. In some embodiments, the antibiotic is a lincosamide selected from the group consisting of clindamycin and lincomycin.

In some embodiments, the antibiotic is a macrolide. In some embodiments, the antibiotic is a macrolide selected from the group consisting of azithromycin, clarithromycin, erythromycin, and telithromycin.

In some embodiments, the antibiotic is a penicillin. In some embodiments, the antibiotic is a penicillin selected from the group consisting of amoxicillin, ampicillin, dicloxacillin, nafcillin, oxacillin, penicillin, ticarcillin, and piperacillin.

In some embodiments, the antibiotic is a quinolone. In some embodiments, the antibiotic is a quinolone selected from the group consisting of ciprofloxacin, levofloxacin, moxifloxacin, and ofloxacin.

In some embodiments, the antibiotic is a sulfonamide. In some embodiments, the antibiotic is a sulfonamide which is bactrim.

In some embodiments, the antibiotic is a tetracycline. In some embodiments, the antibiotic is a tetracycline selected from the group consisting of doxycycline and minocycline.

In some embodiments, D is a regenerative molecule. Example regenerative molecules include, but are not limited to, molecules for regenerating a hair cell and molecules for a regenerating a neuron cell.

In some embodiments, the regenerative molecule is a molecule for regenerating a hair cell. In some embodiments, the regenerative molecule is a molecule for regenerating a hair cell, wherein the molecule is selected from the group consisting of a gamma-secretase inhibitor (e.g., Merck GSI MK-0752; Lilly GSI L685458; LY411575, DAPT, and MDL28170), a Notch activator (e.g., Resveratrol; see, for example, Pinchot et al, *Identification and validation of Notch pathway activating compounds through a novel high-throughput screening method.*, 2011, Cancer, 117(7): 1386-98), a Wnt related small molecule (e.g., CWP232228, IQ1, QS11, IWR, XAV939, DCA, 2-amino-4-[3,4-(methylenedioxy)benzyl-amino]-6-(3-methoxyphenyl)pyrimidine, and a (hetero)arylpyrimidine compound). Additional Wnt related small molecules may be found, for example, at http://web.stanford.edu/~rnusse/assays/smallmol.html, the disclosure of which is incorporated by reference herein in its entirety. Aurora A Kinase (see e.g., Zhonghan Li et al, *A kinase inhibitor screen identifies small-molecule enhancers of reprogramming and iPS cell generation*, 2012, Nat Commun., 3:1085); a GSK-3beta inhibitor, (e.g., Lithium-Chloride and valproic acid (VPA)), and a Sox activator (e.g., RepSox; see, for example, Ichida et al, *A small-molecule inhibitor of tgf-Beta signaling replaces sox2 in reprogramming by inducing nanog*, 2009, Cell Stem Cell. 6; 5(5):491-503).

In some embodiments, the regenerative molecule is a molecule for regenerating a neuron cell. In some embodiments, the regenerative molecule is a molecule for regenerating a neuron cell selected from the group consisting of a BDNF small molecule mimic (e.g., cianidanol, diosmetin, methoxyvone, quercetin, epicatechin, 7,8-dihydroxyflavone, pinocembrin, epiafzelechin, and fisetinidol. See e.g., Jang et al, *Proceedings of the National Academy of Sciences of the United States of America*, 2010, 107(6):2687-2692), a Neurotrophin-3 small molecule mimic (example Neurotrophin-3 small molecule mimics may be found in Zaccaro et al., *Chemistry and Biology*, 2005, 12:1015-1028), and valproic acid (VPA).

In some embodiments, D is an epigenetic modifier. In some embodiments, D is an epigenetic modifier selected from the group consisting of a DNA methyltransferase inhibitor, (e.g., Zebularine, 5-Azacytidine, Procaine, Hydralazine, Procainamide, Caffeic acid, Chlorogenic acid), a methyl-CpG-binding protein (MBP), a histone methyltransferase (HMT, e.g., H3 peptide substrate-competitive inhibitors and S-adenosylmethionine (SAM) cofactor-competitive inhibitors, BIX-01338, and BRD9539), a histone demethylase (HDM), a histone acetyltransferase (HAT), for example, CPTH2, Curcumin, and MB-3; and a histone deacetylase (HDAC) inhibitor, for example resveratrol. Additional HDAC inhibitors may be found, for example, at http://www.sigmaaldrich.com/life-science/molecular-biology/molecular-biology-products.html?TablePage=106211963, the disclosure of which is incorporated by reference herein in its entirety).

In some embodiments, D is a chemotherapeutic agent. Example chemotherapeutic agents include, but are not limited to, alkylating agents, antimetabolites, anti-tumor antibiotics, topoisomerase inhibitors, mitotic inhibitors, and hormone receptor inhibitors.

In some embodiments, D is an alkylating agent selected from the group consisting of cyclophosphamide, ifosfamide, cisplatin, carboplatin. In some embodiments, D is an antimetabolite selected from the group consisting of 5-fluorouracil, 6-mercaptopurine, gemcitabine, methotrexate, and hydroxyurea. In some embodiments, D is an anti-tumor antibiotic selected from the group consisting of doxorubicin, daunorubicin, bleomycin, and mitomycin-C. In some embodiments, D is a topoisomerase inhibitor selected from the group consisting of etoposide and topotecan. In some embodiments, D is a mitotic inhibitor selected from the group consisting of paclitaxel and vincristine. In some embodiments, D is a hormone receptor inhibitor selected from the group consisting of bevacizumab and a VEGF inhibitor.

In some embodiments, D is an immunotherapy agent. In some embodiments, Example immunotherapy agents include, but are not limited to, small molecule cancer vaccines, checkpoint inhibitors, and monoclonal antibodies. In some embodiments, D is an immunotherapy agent selected from the group consisting of a small molecule cancer vaccine (e.g., rV/F-CEA/TRICOM, Hodge et al, *The tipping point for combination therapy: cancer vaccines with radiation, chemotherapy, or targeted small molecule inhibitors*, 2012 Semin Oncol., 39(3):323-39; WT1), a checkpoint inhibitor (e.g., SP4206, Barakat, K, *Do We Need Small Molecule Inhibitors for the Immune Checkpoints?* 2014, J Pharma Care Health Sys, 1:e119), and a monoclonal antibody (e.g., trastuzumab, ipilimumab, rivolumab, and pembrolizumab).

In some embodiments, D is a single gene target. Example single gene targets include, but are not limited to, CRISPR/Cas systems. In some embodiments, D is a single gene target which is a Cas9 protein.

In some embodiments, D is an ion regulator. In some embodiments, D is an ion regular which is a calcium channel inhibitor. In some embodiments, D is a calcium channel inhibitor selected from the group consisting of nifedipine, diltiazem, nimodipine, verapamil.

In some embodiments, D is a therapeutic agent selected from the group consisting of cisplatin, doxorubicin, taxol, etoposide, irinotecan, topotecan, paclitaxel, docetaxel, epothilones, tamoxifen, 5-fluorouracil, methotrexate, temozolomide, cyclophosphamide, tipifarnib, gefitinib, erlotinib hydrochloride, antibodies to EGFR, imatinib mesylate, gemcitabine, uracil mustard, chlormethine, ifosfamide, melphalan, chlorambucil, pipobroman, triethylenemelamine, triethyl enethiophosphoramine, busulfan, carmustine, lomustine, streptozocin, dacarbazine, floxuridine, cytarabine, 6-mercaptopurine, 6-thioguanine, fludarabine phosphate, oxaliplatin, folinic acid, pentostatin, vinblastine, vincristine, vindesine, bleomycin, dactinomycin, daunorubicin, epirubicin, idarubicin, mithramycin, deoxycoformycin, mitomycin-C, L-asparaginase, teniposide, 17α-ethinylestradiol, diethylstilbestrol, testosterone, prednisone, fluoxymesterone, dromostanolone propionate, testolactone, megestrol acetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, vinorelbine, anastrazole, letrozole, capecitabine, reloxafine, hexamethylmelamine, bevacizumab, bexxar, velcade, zevalin, trisenox, xeloda, porfimer, erbitux, thiotepa, altretamine, trastuzumab, fulvestrant, exemestane, rituximab, alemtuzumab, clofarabine, cladribine, aphidicolin, sunitinib, dasatinib, tezacitabine, triapine, didox, trimidox, amidox, bendamustine, ofatumumab, and idelalisib.

In some embodiments, D is a microglial inhibitor. Example microglial inhibitors include, but are not limited to, naltrexone, dextro-naltrexone, minocycline, spironolactone, dextromethorphan, rapamycin, everolimus, rifampin, propentofylline, ceftriaxone, glatiramer acetate, ibudilast, and the like. In some embodiments, D is a microglial inhibitor selected from the group consisting of naltrexone, dextro-naltrexone, minocycline, spironolactone, dextromethorphan, rapamycin, everolimus, rifampin, propentofylline, ceftriaxone, glatiramer acetate, and ibudilast.

In some embodiments, D is a carbonyl-substituted analog of a therapeutic agent.

As used herein, the term "carbonyl-substituted analog" refers to a therapeutic agent that has been modified to include an additional carbonyl group (CO). For example, 7,8-dihydroxyflavone and a corresponding carbonyl-substituted analog are shown below:

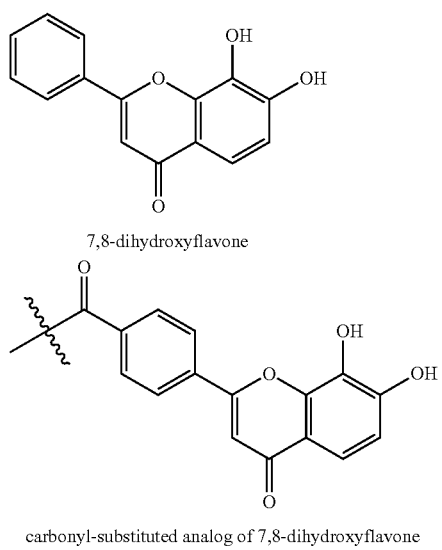 [SMILES: O=c1cc(-c2ccccc2)oc2c(O)c(O)ccc12 ; *C(=O)c1ccc(-c2cc(=O)c3ccc(O)c(O)c3o2)cc1]

7,8-dihydroxyflavone carbonyl-substituted analog of 7,8-dihydroxyflavone where ⌇⌇⌇ represents the location of the bond between D and Z.

In some embodiments, the conjugate of Formula I is a conjugate of Formula II:

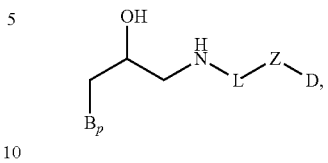

or a pharmaceutically acceptable salt thereof, wherein variables $B_p$, L, Z, and D are defined according to the definitions provided herein for conjugates of Formula I.

In some embodiments, the conjugate of Formula I is a conjugate of Formula IIa:

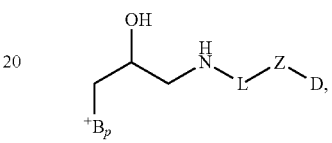

wherein variables $B_p$, L, Z, and D are defined according to the definitions provided herein for conjugates of Formula I.

In some embodiments, the conjugate of Formula I is a conjugate of Formula III:

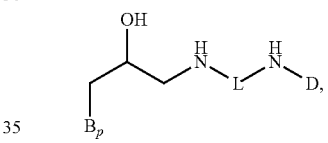

or a pharmaceutically acceptable salt thereof, wherein variables $B_p$, L, and D are defined according to the definitions provided herein for conjugates of Formula I.

In some embodiments, the conjugate of Formula I is a conjugate of Formula IIIa:

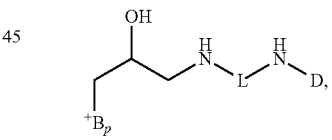

wherein variables $B_p$, L, and D are defined according to the definitions provided herein for conjugates of Formula I.

In some embodiments, the conjugate of Formula I is a conjugate of Formula IV:

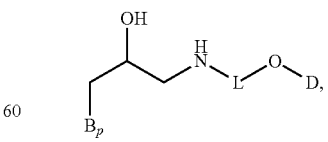

or a pharmaceutically acceptable salt thereof, wherein variables $B_p$, L, and D are defined according to the definitions provided herein for conjugates of Formula I.

In some embodiments, the conjugate of Formula I is a conjugate of Formula IV:

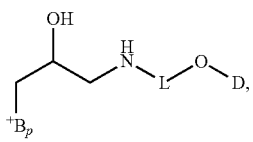

wherein variables $B_p$, L, and D are defined according to the definitions provided herein for conjugates of Formula I.

In some embodiments, the conjugate of Formula I is a conjugate of Formula V:

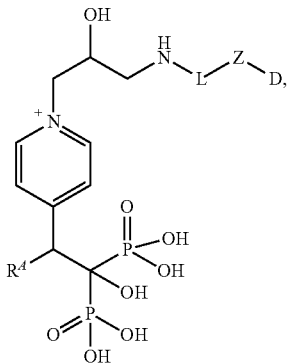

wherein variables $R^A$, L, Z, and D are defined according to the definitions provided herein for conjugates of Formula I.

In some embodiments, the conjugate of Formula I is a conjugate of Formula VI:

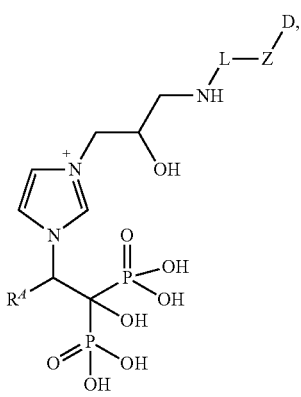

wherein variables $R^A$, L, Z, and D are defined according to the definitions provided herein for conjugates of Formula I.

In some embodiments, the conjugate of Formula I is a conjugate of Formula VII:

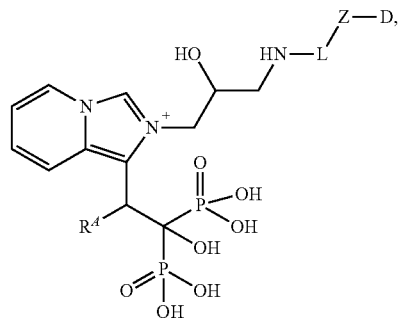

wherein variables $R^A$, L, Z, and D are defined according to the definitions provided herein for conjugates of Formula I.

In some embodiments, the conjugate of Formula I is a conjugate of Formula VIII:

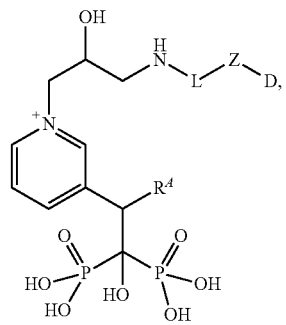

wherein variables $R^A$, L, Z, and D are defined according to the definitions provided herein for conjugates of Formula I.

In some embodiments, the conjugate of Formula I is a conjugate of Formula IX:

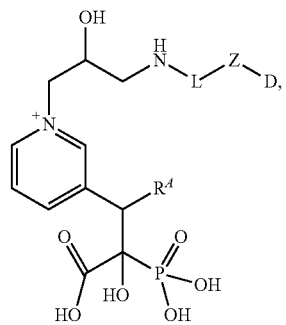

wherein variables $R^A$, L, Z, and D are defined according to the definitions provided herein for conjugates of Formula I.

In some embodiments, the conjugate of Formula I is selected from the group consisting of:

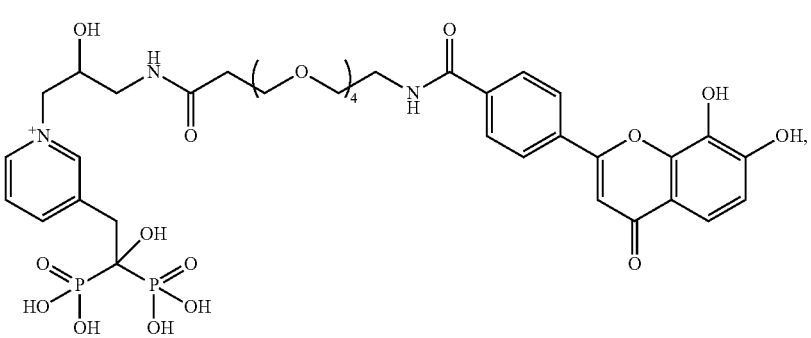

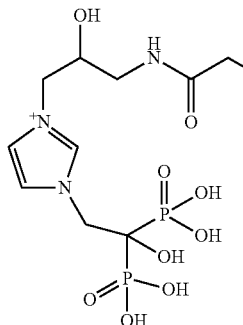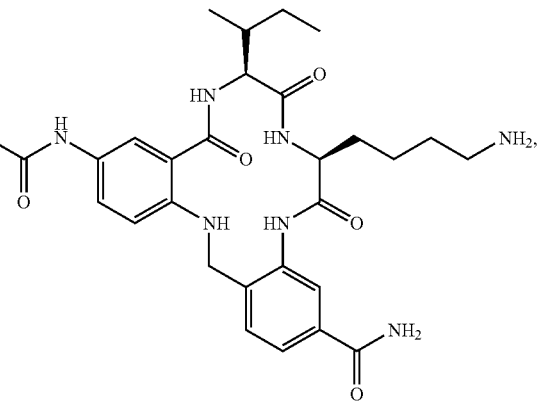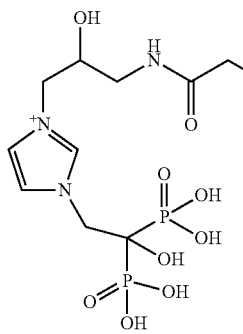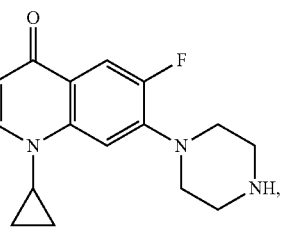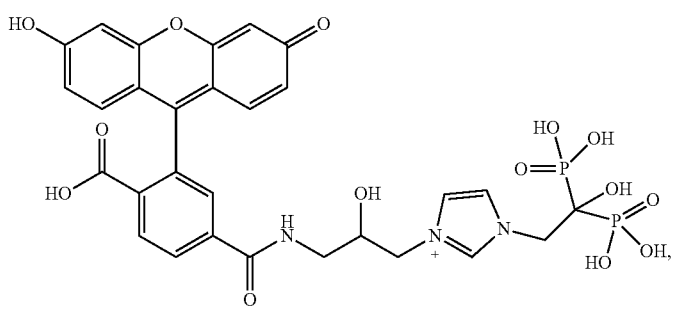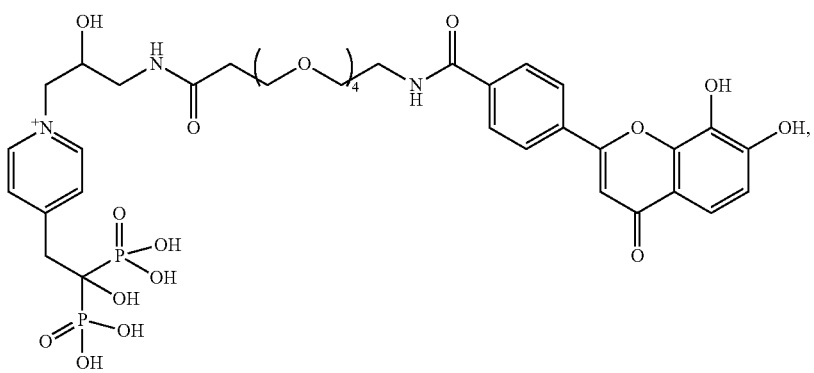

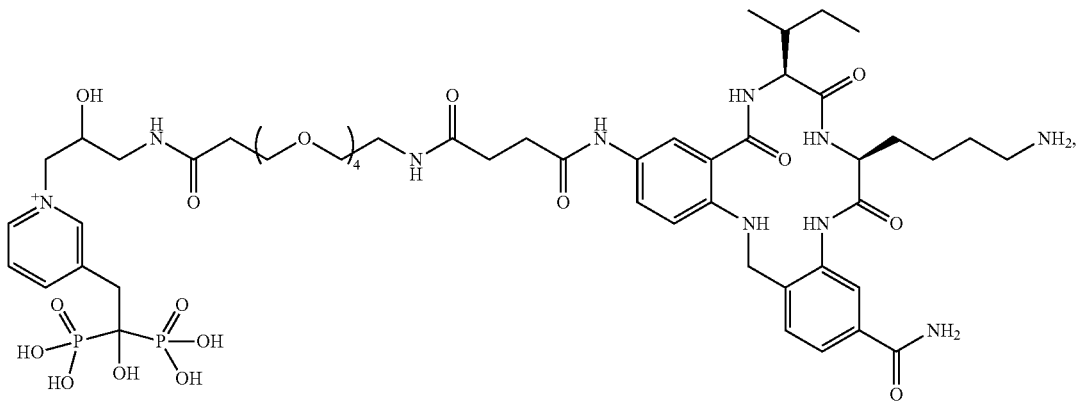
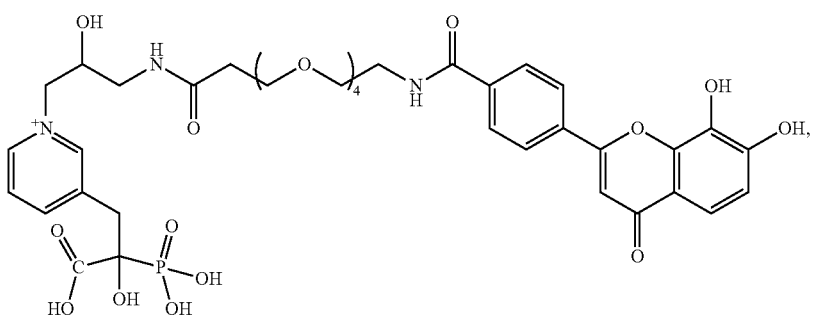
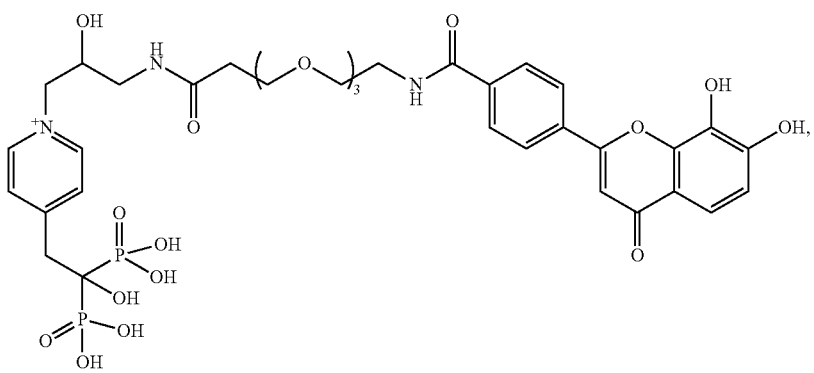
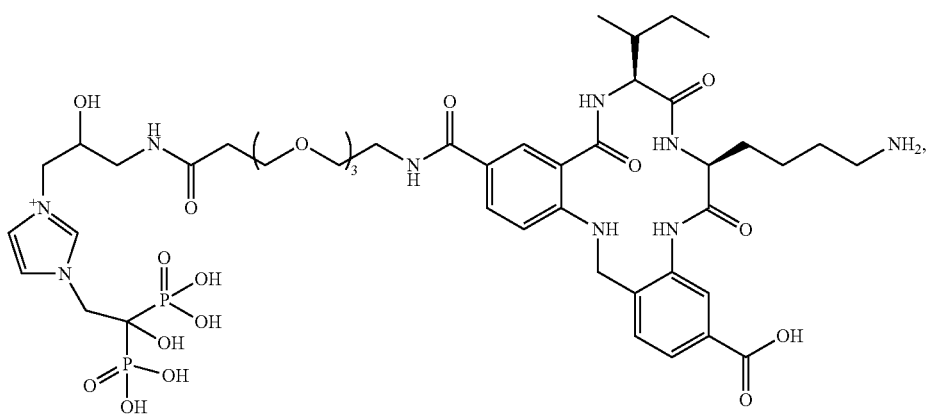

-continued
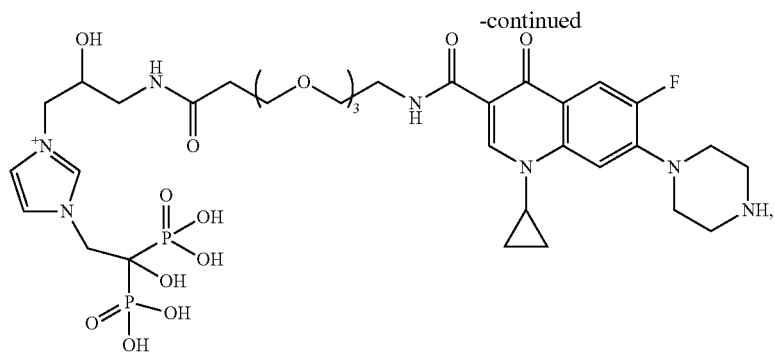
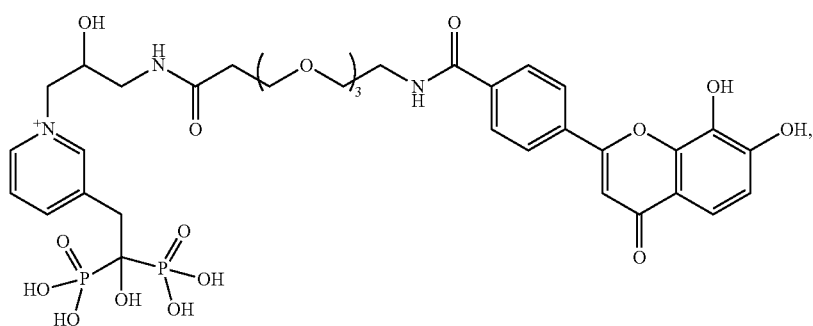
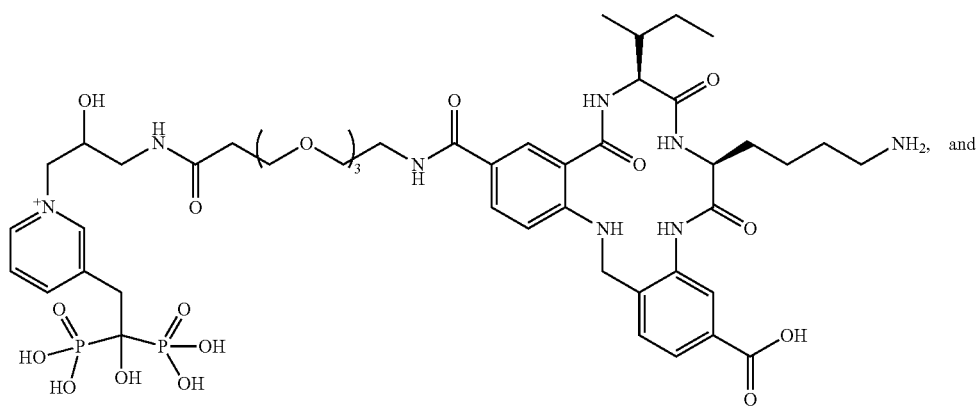
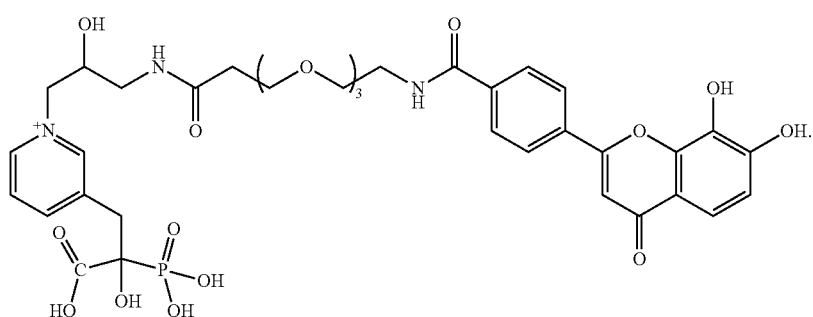
In some embodiments, the conjugate is selected from the group consisting of:

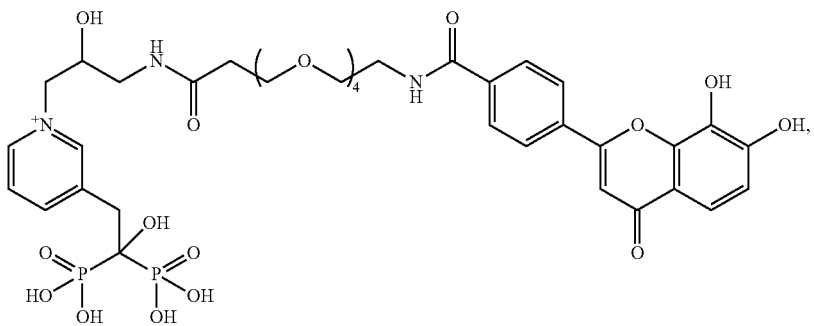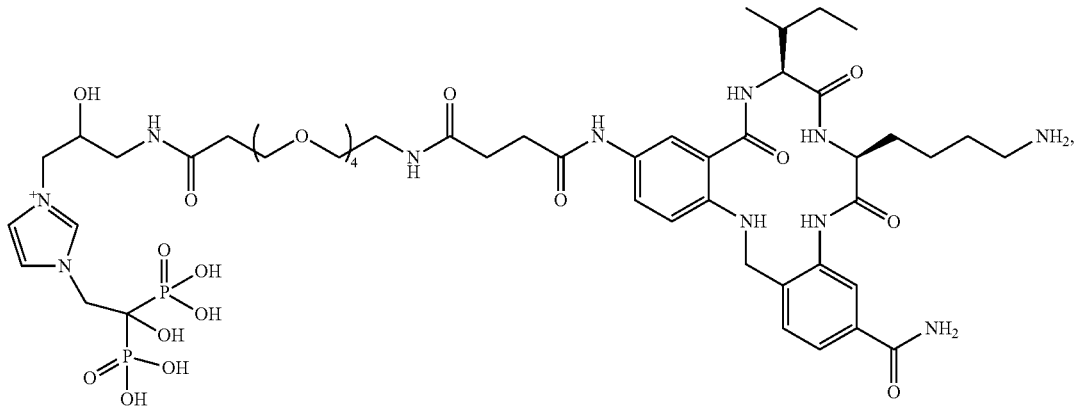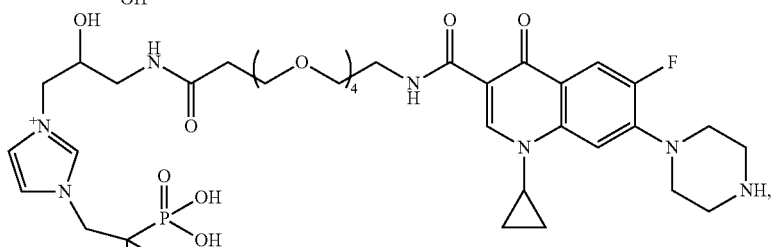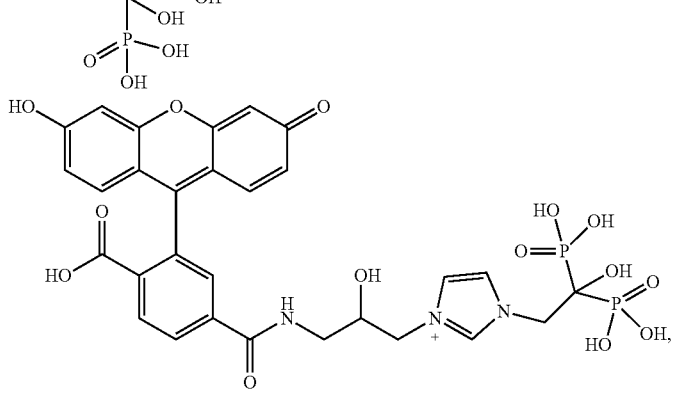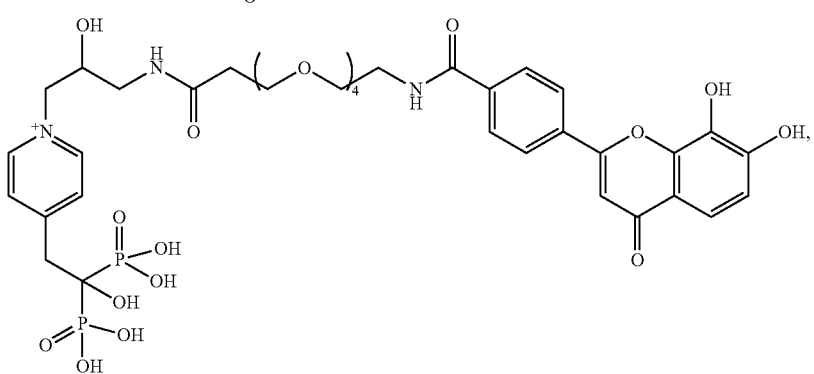

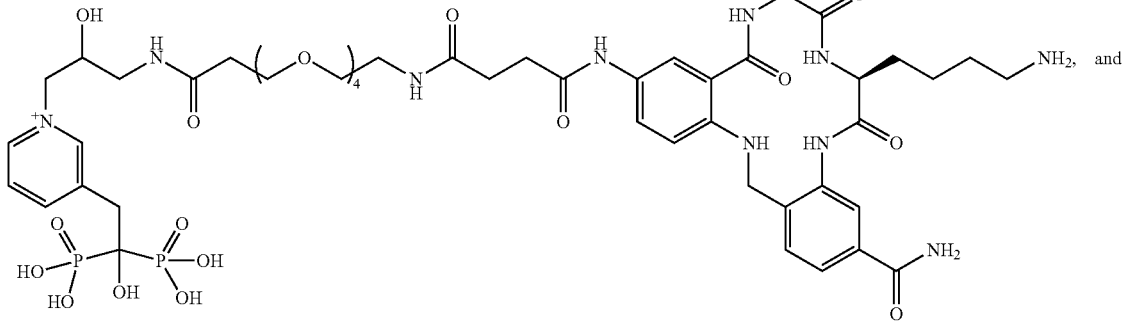
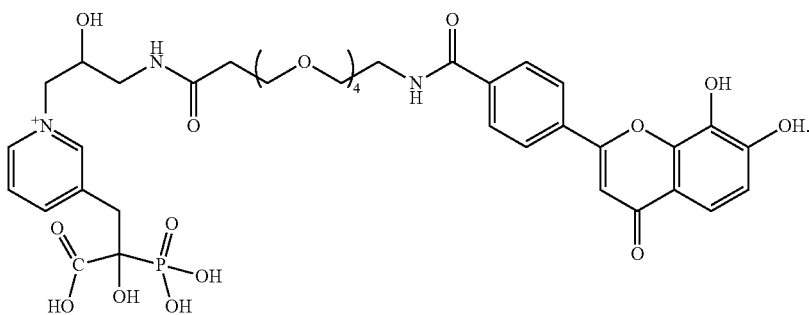
In some embodiments, the conjugate of Formula I is selected from the group consisting of:
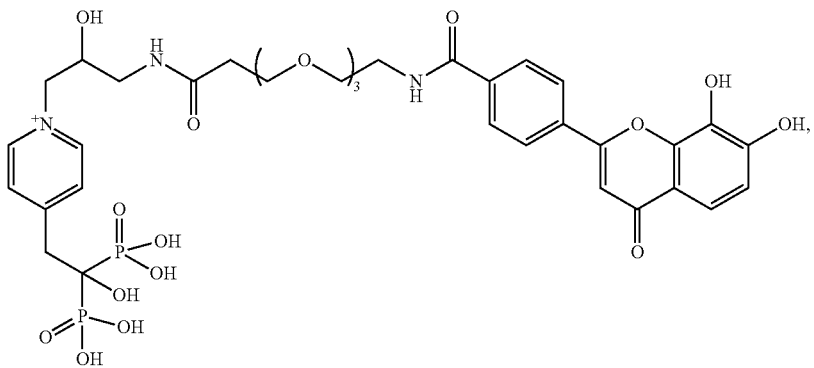
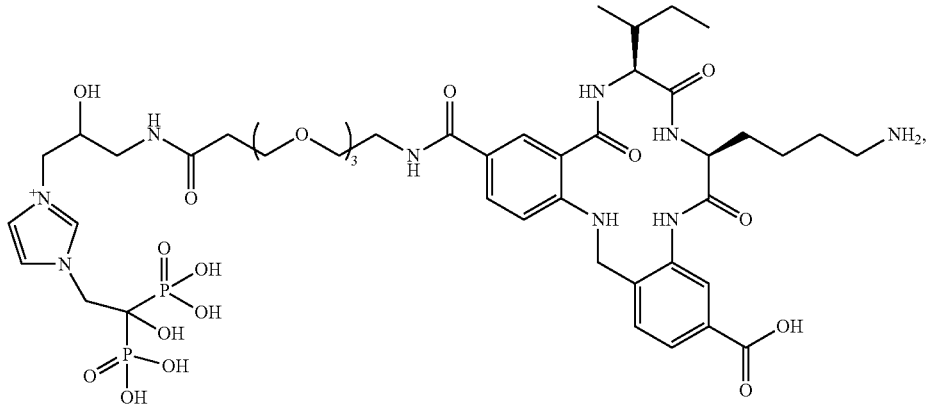

-continued
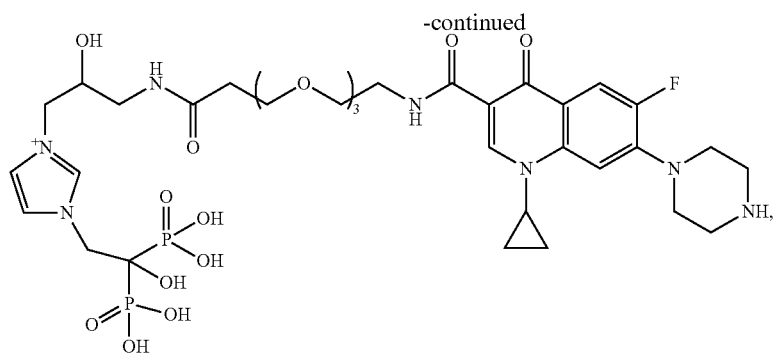
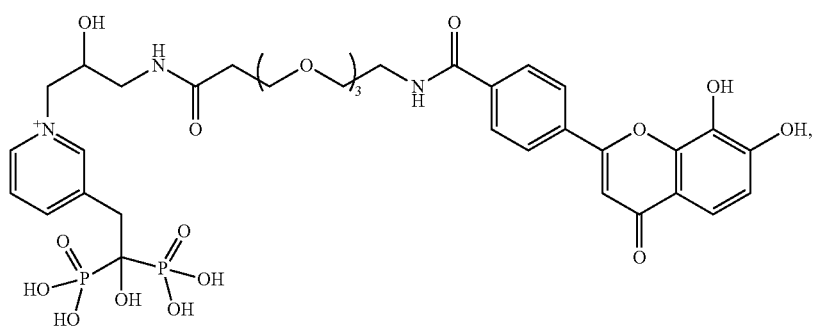
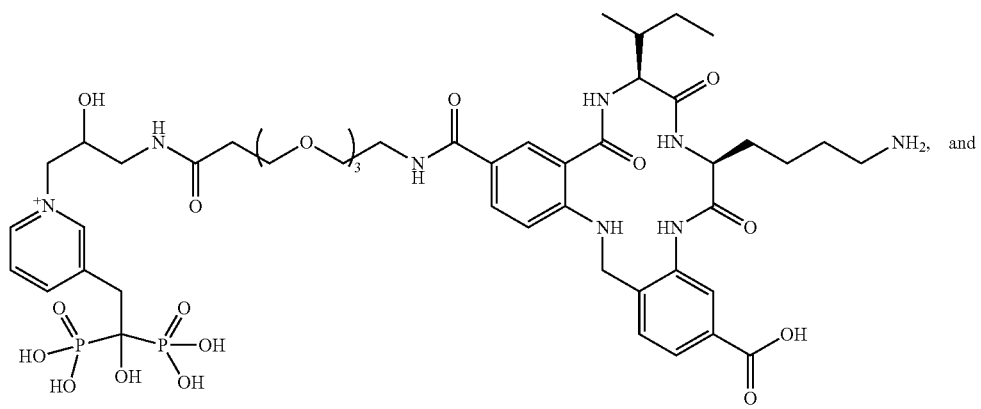
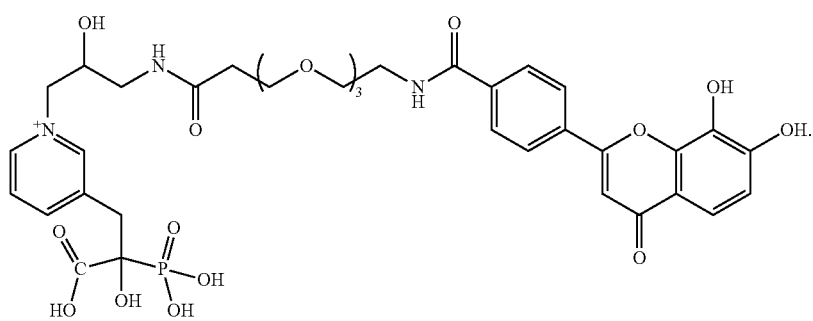
In some embodiments, the conjugate of Formula I is selected from the group consisting of:

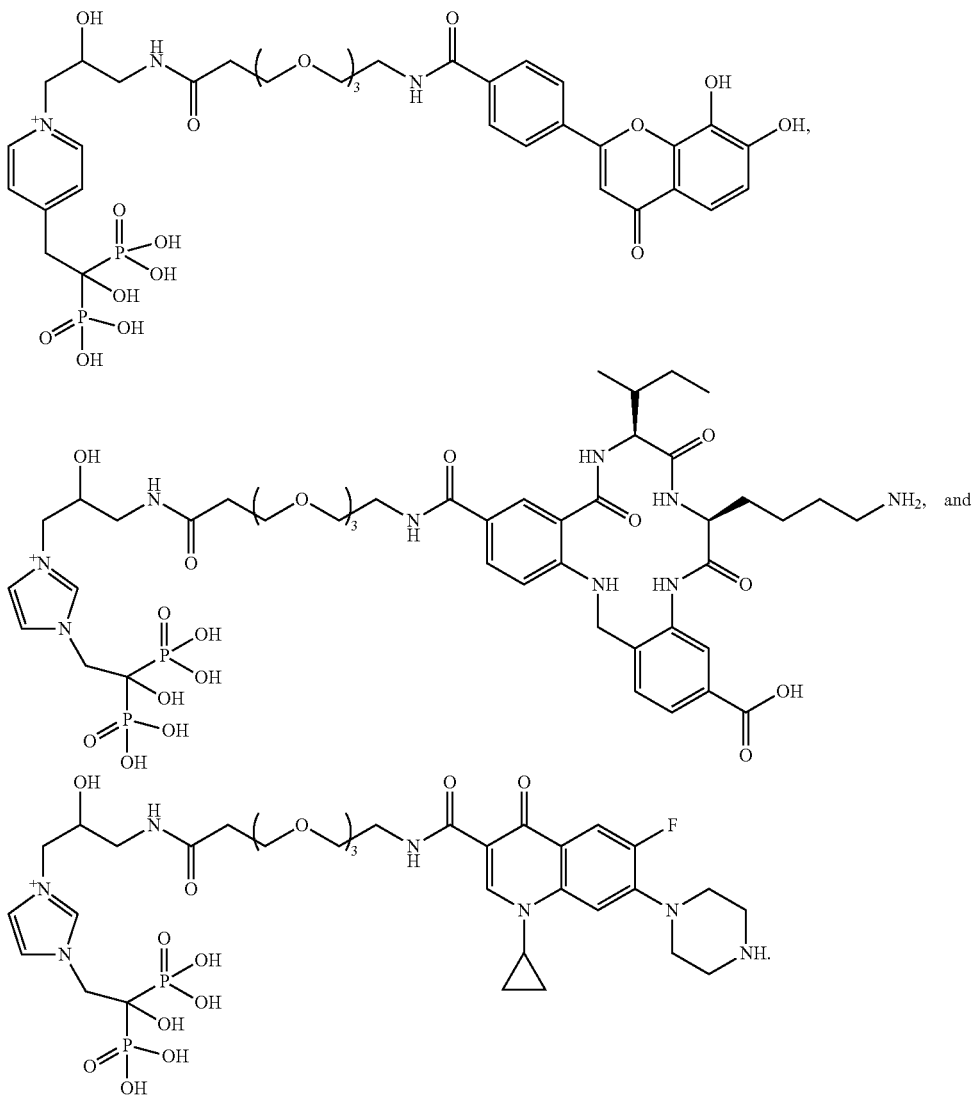

Synthesis

As will be appreciated, the conjugates provided herein can be prepared using known organic synthesis techniques and can be synthesized according to any of numerous possible synthetic routes.

For example, the conjugates of Formula I may be prepared according to the procedure shown in Scheme 1. Protecting group X for the carboxylic group in linker L may be tert-butyl but also can be other groups including, but not limited to, methyl, benzyl, ortho-nitrobenzyl or other commonly used protecting groups for a carboxylic group. The general synthesis shown in Scheme 1 is applicable to a wide range of drugs and small molecules. In particular, this approach works well with any drug or small molecule that contains a carboxylic moiety in its native structure. This carboxylic group will allow the conjugation of the drug D to linker 2, a PEG linker, followed by subsequent coupling with 5a, a bisphosphonate linker derivative, to obtain the desired conjugate 6a. In some embodiments, the drug or small molecule is a therapeutic agent provided herein, for example, a steroid, an antibiotic, a regenerative molecule, an epigenetic modifier, a chemotherapeutic agent, an immunotherapy agent, a single gene target, and an ion regulator. In some embodiments, the drug or small molecule is a therapeutic agent selected from the group consisting of a neurotrophic agent (e.g., a 7,8-dihydroxy flavone (DHF) derivative, peptidomimetics), a β-lactam antibiotic (e.g, penicillins, cephalosporins, carapenems, etc.), a quinolone, a glycopeptide (e.g., vancomycin), and an antimetabolite (e.g., methotrexate).

If necessary, protection of amino and hydroxyl groups that may be present in the drug can be first performed before the synthetic route shown in Scheme 1 is carried out for D-COOH. The protecting group for the amino group may be t-BOC or appropriate N-protecting groups including, but not limited to, Fmoc, Cbz, Bn, Mtt, ortho-nitrobenzyl. The protecting group for the hydroxyl group may be benzyl ether or other O-protecting groups including, but not limited to, silyl, tert-butyl, Mtt, or ortho-nitrobenzyl. Methods for the deprotection of these amino and hydroxyl moieties can be the same; however, methods of the N- or O-deprotection cannot overlap with that of the protected carboxyl group in linker L.

Scheme 1.

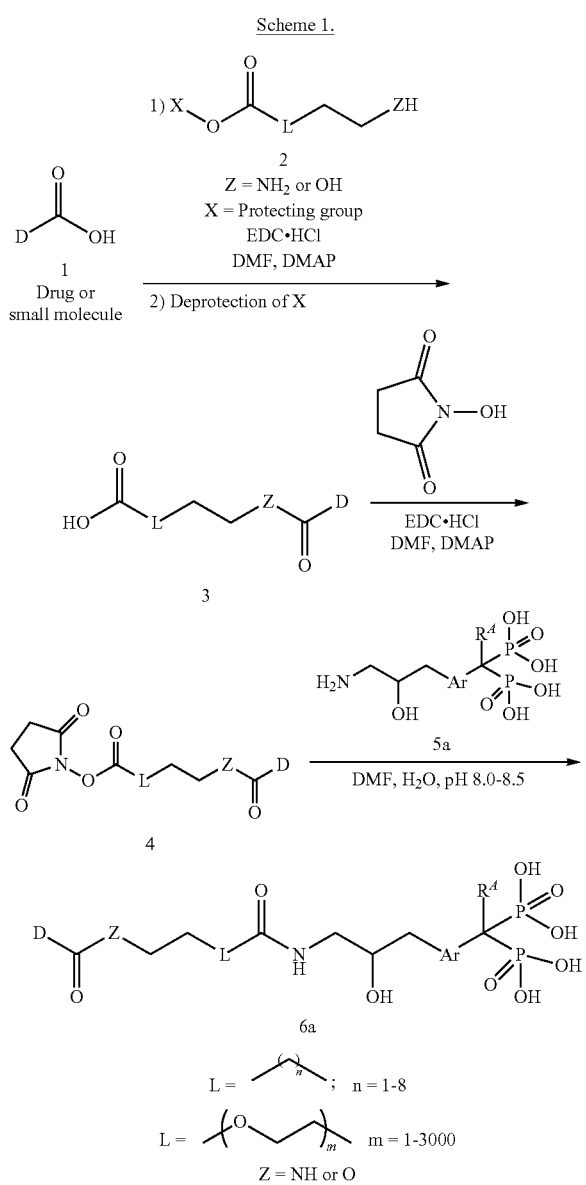

The conjugates of Formula I can also be prepared, for example, according to the procedure shown in Scheme 2. Synthesis of Drug-linker PC conjugates will be achieved using approach shown in Scheme 2.

Similar to the description of bisphosphonates (BPs) in Scheme 1, phosphonocarboxylate (PC) conjugates used for this synthesis can have either 3-ethyl-pyridinium, 1-ethyl-1H-imidazolium, or 1-ethylimidazo[1,5-a]pyridinium substituents at the Ar position, or with any other attaching positions on the N-heterocyclic rings (e.g. 2-ethyl-pyridinium, 4-ethyl-pyridinium, etc.), in combination with $R^A$=H, OH, F, or Cl.

The general synthesis provided in Scheme 2 is applicable to a wide range of drugs and small molecules. Similar to Scheme 1, this approach works particularly well with any drug or small molecule that contains a carboxylic moiety in their native structures. This carboxylic group will allow the conjugation of the molecule of interest to linker 2, a PEG linker, followed by subsequent coupling with 5b, PC linker derivatives, to obtain the desired conjugate 6b. In some embodiments, the drug or small molecule is a therapeutic agent provided herein, for example, a steroid, an antibiotic, a regenerative molecule, an epigenetic modifier, a chemotherapeutic agent, an immunotherapy agent, a single gene target, and an ion regulator. In some embodiments, the drug or small molecule is a therapeutic agent selected from the group consisting of a neurotrophic agent (e.g., a 7,8-dihydroxy flavone (DHF) derivative, peptidomimetics), a β-lactam antibiotic (e.g, penicillins, cephalosporins, carapenems, etc.), a quinolone, a glycopeptide (e.g., vancomycin), and an antimetabolite (e.g., methotrexate).

Protecting group X for the carboxylic group in linker G may be tert-butyl but also can be other groups, such as methyl, Bn, ortho-nitrobenzyl or other commonly used protecting groups for the carboxylic group.

If necessary, protection of amino and hydroxyl groups that may be present in the drug can be first performed before the synthetic route shown in Scheme 2 is carried out for D-COOH. The protecting group for the amino group may be t-BOC or appropriate N-protecting groups including, but not limited to, Fmoc, Cbz, Bn, Mtt, ortho-nitrobenzyl. The protecting group for the hydroxyl group may be benzyl ether or other O-protecting groups including, but not limited to, silyl ether, tert-butyl ether, Mtt, or ortho-nitrobenzyl ether. Methods for the deprotection of these amino and hydroxyl moieties can be the same; however, methods of the N- or O-deprotection cannot overlap with that of the protected carboxyl group in linker L.

Scheme 2.

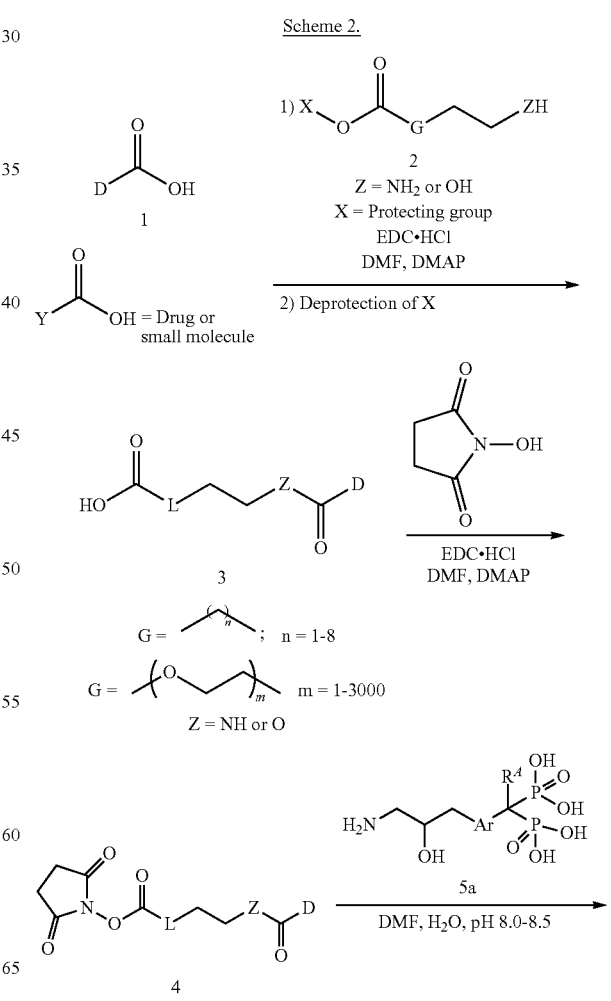

-continued

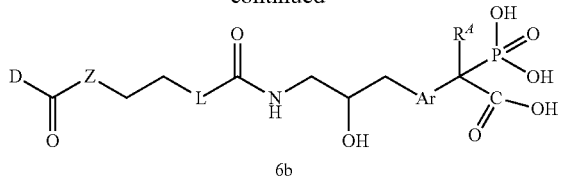

The conjugates of Formula I can also be prepared, for example, according to the procedure shown in Scheme 3. The synthesis of DHF-linker-BP conjugates using an amido linkage was achieved using the approach described in Scheme 1. The synthesis was performed with a risedronate analogue and a new derivative of (DHF) containing a carboxylic moiety that allows further conjugation.

Scheme 3.

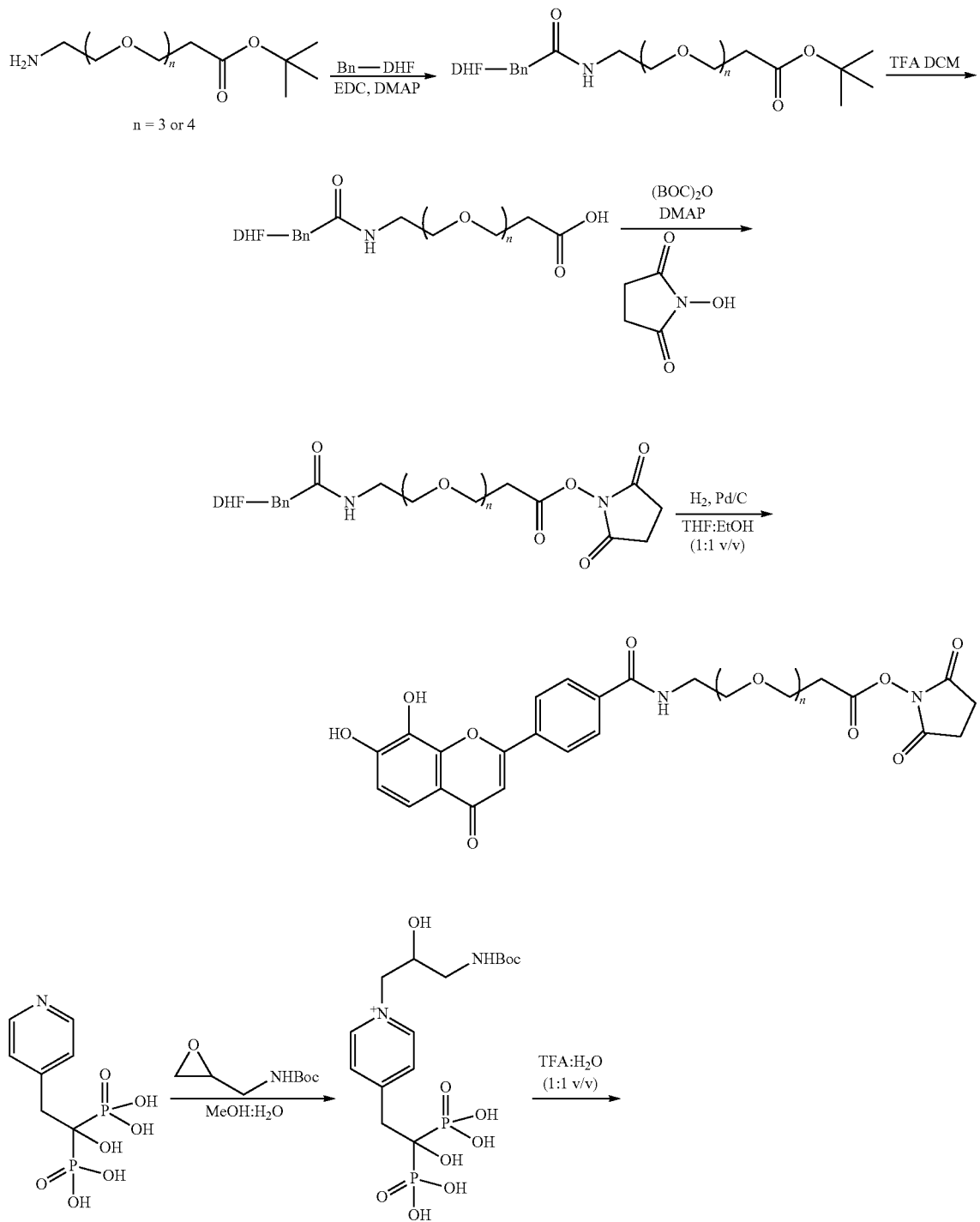

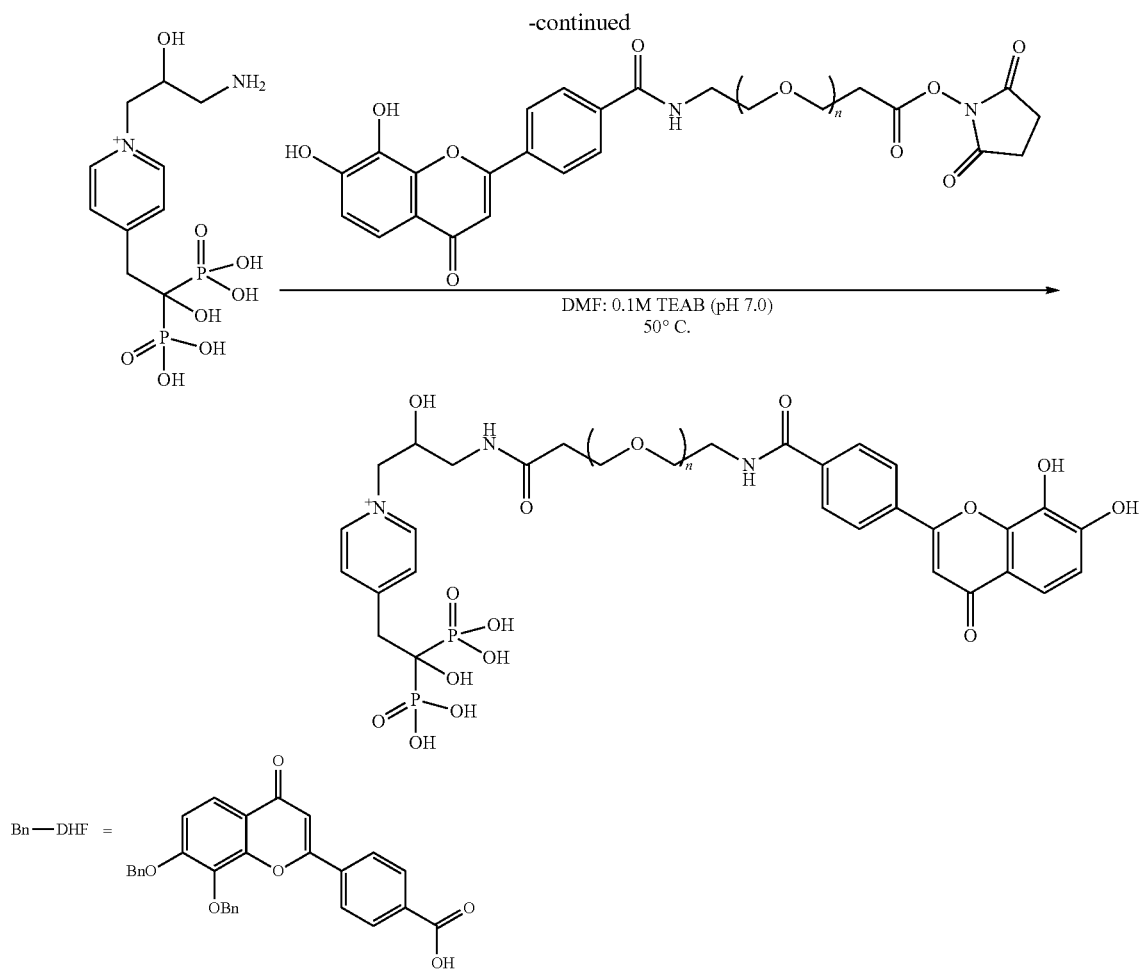
The conjugates of Formula I can also be prepared, for example, according to the procedure shown in Scheme 3a.
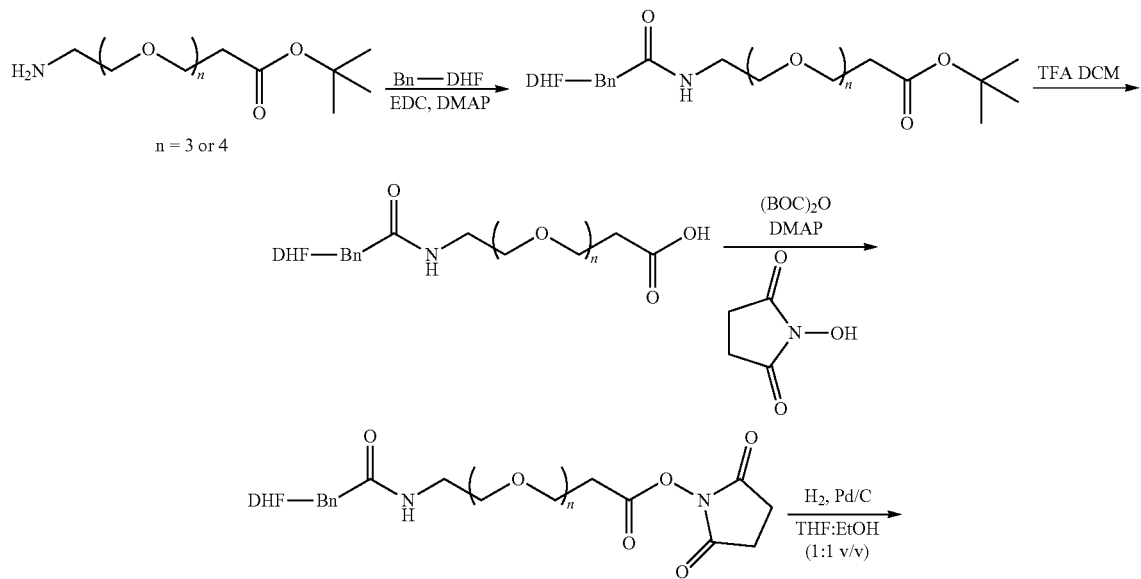

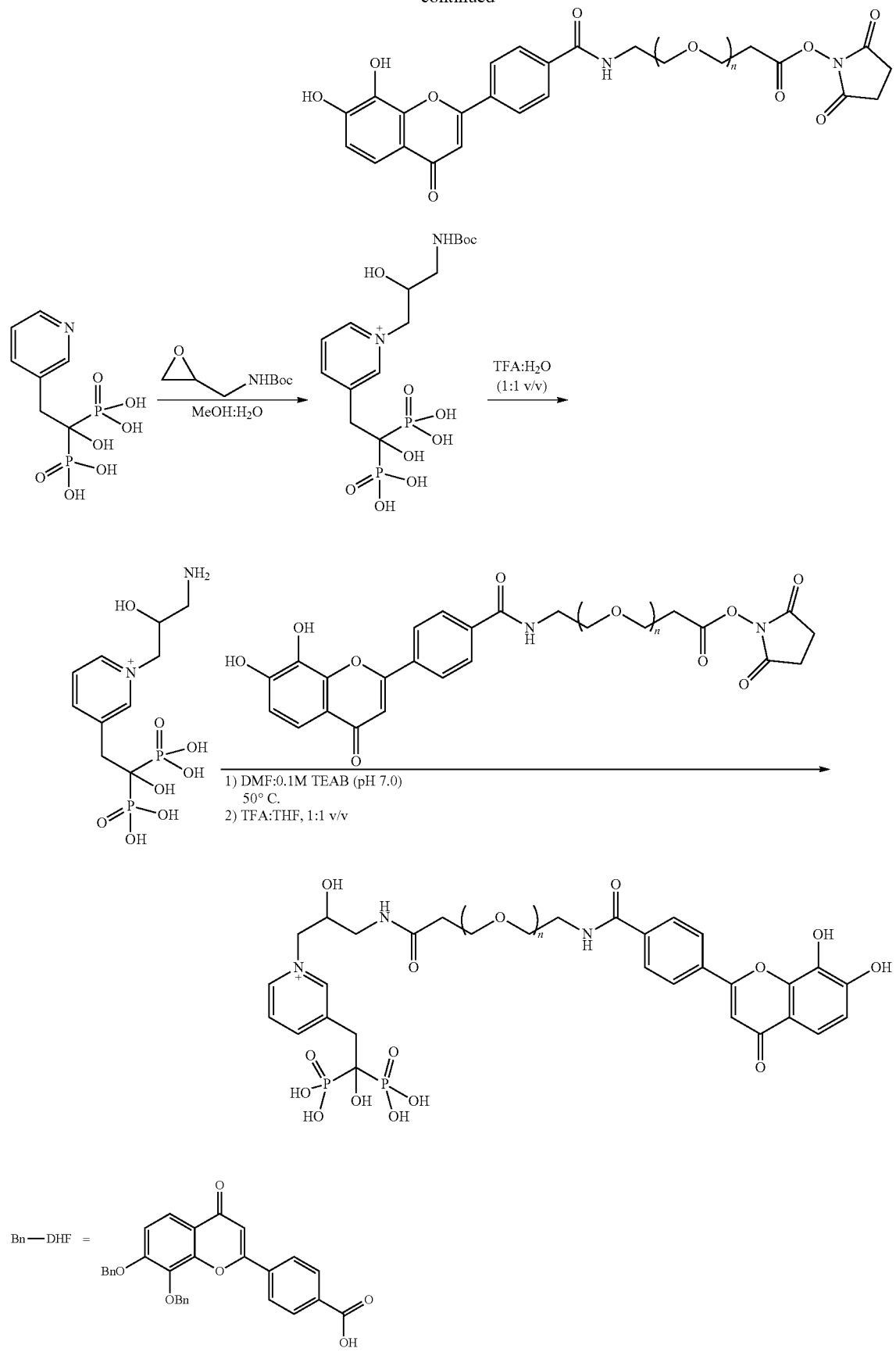

The conjugates of Formula I can also be prepared, for example, according to the procedure shown in Scheme 4.
Scheme 4.
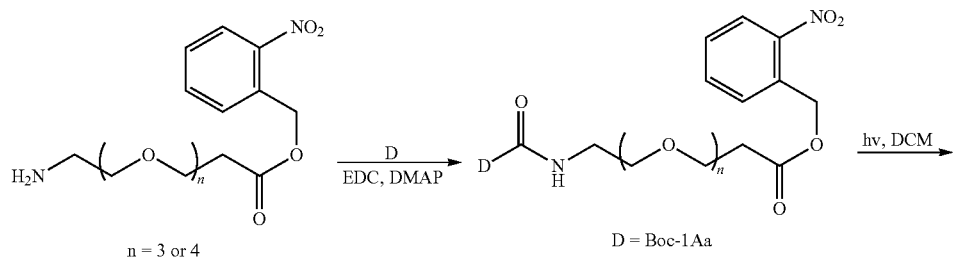
n = 3 or 4    D = Boc-1Aa
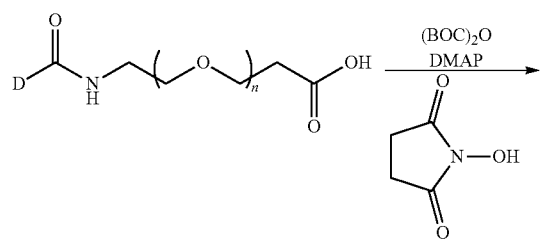
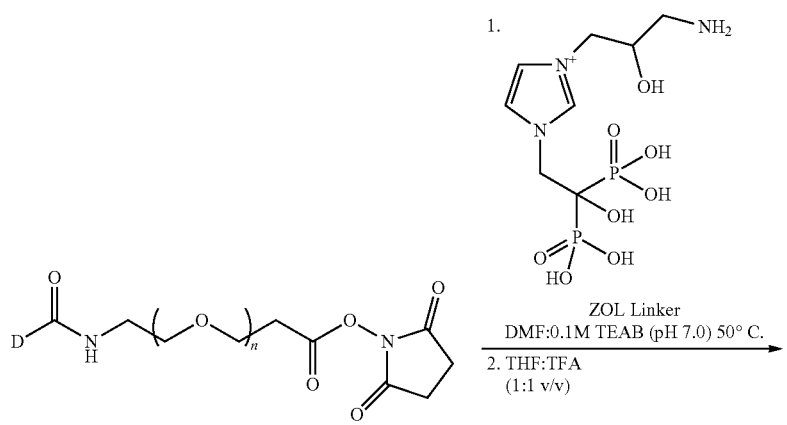
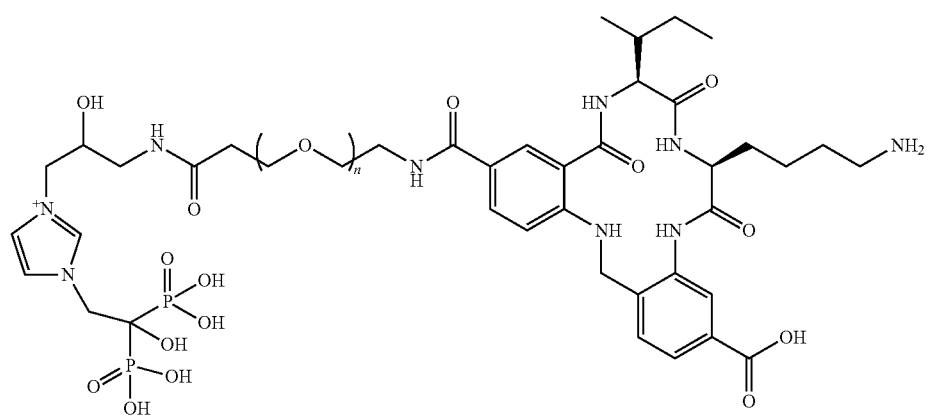

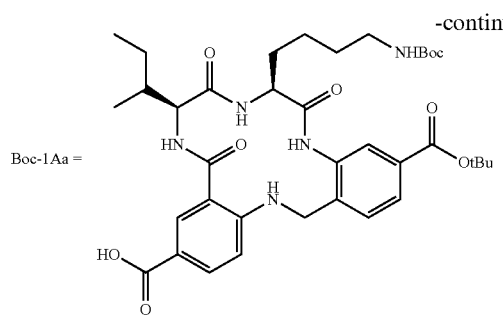
The conjugates of Formula I can also be prepared, for example, according to the procedure shown in Scheme 4a.
Scheme 4a.
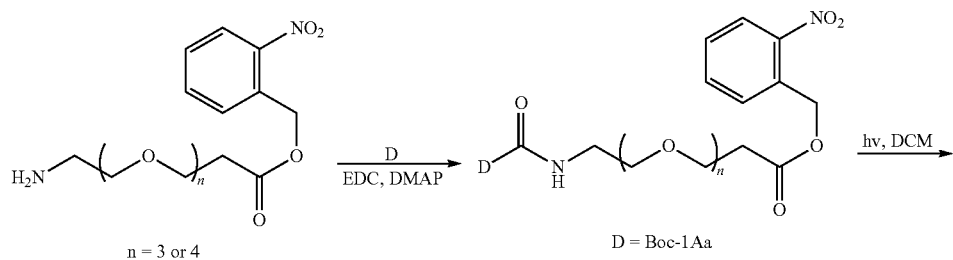
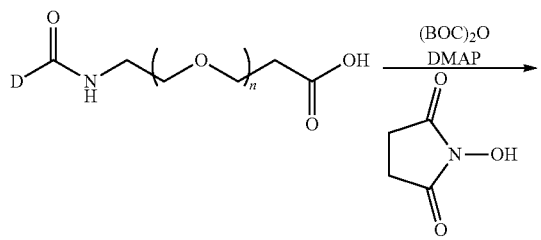
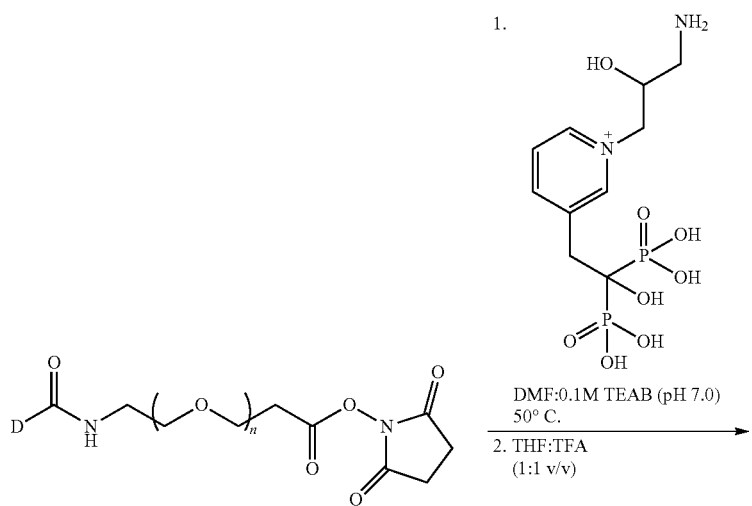

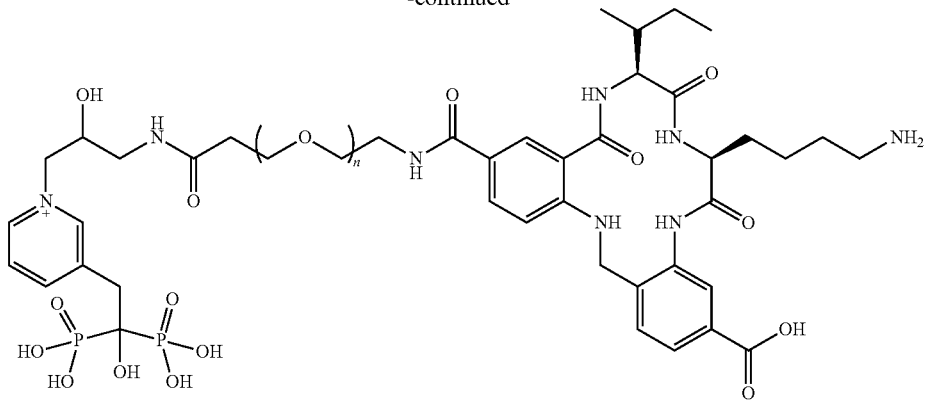
The conjugates of Formula I can also be prepared, for example, according to the procedure shown in Scheme 5.
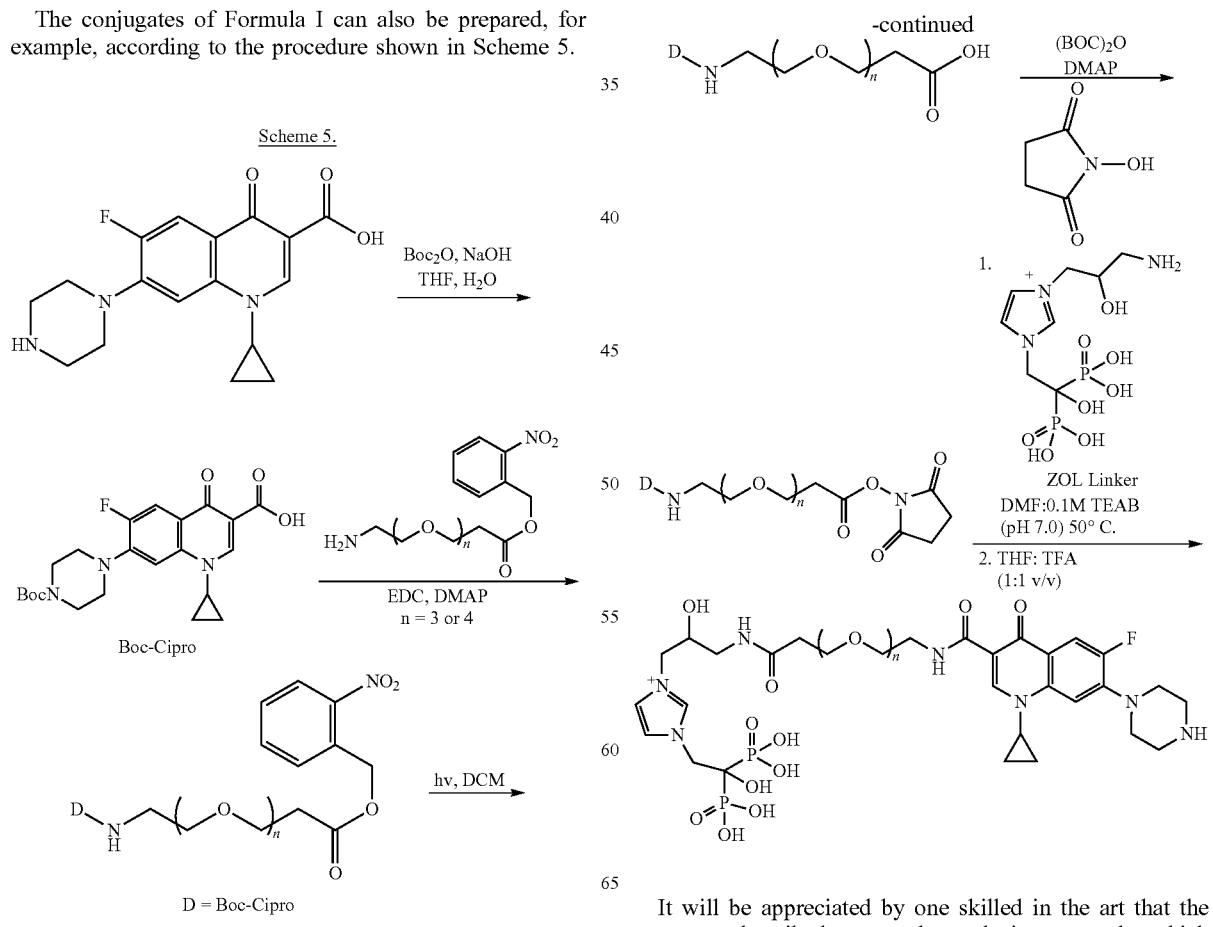
It will be appreciated by one skilled in the art that the processes described are not the exclusive means by which conjugates provided herein may be synthesized and that a broad repertoire of synthetic organic reactions is available to be potentially employed in synthesizing conjugates provided herein. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry Vols.* 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, $6^{th}$ Ed. (Wiley, 2007); Trost et al. (Ed.), *Comprehensive Organic Synthesis* (Pergamon Press, 1991).

The reactions for preparing conjugates described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

Preparation of conjugates described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, $3^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). The conjugates can be purified by those skilled in the art by a variety of methods, including high performance liquid chromatography (HPLC) and normal phase silica chromatography.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl linking group having n to m carbon atoms. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n-m}$ alkenylene", employed alone or in combination with other terms, refers to a divalent alkenylene linking group having n to m carbon atoms. Example alkenylene groups include, but are not limited to, 1,4-but-2-enylene, 1,5-but-2-enylene, 1,3-prop-2-enylene, and the like. In some embodiments, the alkenylene moiety contains 2 to 6, 2 to 4, or 2 to 3 carbon atoms.

As used herein, the term "$C_{n-m}$ alkynylene", employed alone or in combination with other terms, refers to a divalent alkynylene linking group having n to m carbon atoms. Examples of alkynylene groups include, but are not limited to 1,4-but-1-ynylene, 1,3-but-1-ynylene, 1,4-but-2-ynylene, 1,4-pent-2-ynylene, 1,5-pent-2-ynylene, and the like. In some embodiments, the alkynylene moiety contains 2 to 6, 2 to 4, or 2 to 3 carbon atoms.

As used herein, the term "$C_{n-m}$ cycloalkylene", employed alone or in combination with other terms, refers to a divalent cycloalkylene group having n to m carbon atoms. Examples of cycloalkylene groups include, but are not limited to, 1,3-cyclobutylene, 1,4-cyclopentylene, 2,5-cyclohexylene, and the like. In some embodiments, the cycloalkylene moiety contains 3 to 10, 3 to 8, or 3 to 6, 4 to 6, or 5 to 6 carbon atoms.

As used herein, the term "$C_{n-m}$ alkoxy", employed alone or in combination with other terms, refers to a group of formula —O-alkyl, wherein the alkyl group has n to m carbons. Example alkoxy groups include methoxy, ethoxy, propoxy (e.g., n-propoxy and isopropoxy), tert-butoxy, and the like. In some embodiments, the alkyl group has 1 to 6, 1 to 4, or 1 to 3 carbon atoms.

As used herein, the term "amino" refers to a group of formula —$NH_2$.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "carbonyl", employed alone or in combination with other terms, refers to a —C(=O)— group, which may also be written as C(O).

As used herein, "halo" refers to fluoro, chloro, bromo, or iodo. In some embodiments, a halo is fluoro, chloro, or bromo. In some embodiments, a halo is fluoro or chloro.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Cycloalkyl groups can have 3, 4, 5, 6, 7, 8, 9, or 10 ring-forming carbons ($C_{3-10}$). Ring-forming carbon atoms of a cycloalkyl group can be optionally substituted by oxo or sulfido (e.g., C(O) or C(S)). Cycloalkyl groups also include cycloalkylidenes. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In some embodiments, cycloalkyl is cyclopropyl, cyclobutyl, cyclopentyl, cyclohexyl, cyclopentyl, or adamantyl. In some embodiments, the cycloalkyl has 6-10 ring-forming carbon atoms. In some embodiments, cycloalkyl is adamantyl. Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring.

As used herein, "phosphonate" refers to a group of formula $P(O)(OH)_2$. In some embodiments, $B_p$ is a monophosphonate moiety. In some embodiments, $B_p$ is a bisphosphonate moiety.

As used here, "phosphonocarboxylate" refers to a conjugate or moiety having one or more carboxylic acid group (COOH) or one or more carboxylate group (COOR) and one or more phosphonate group ($P(O)(OH)_2$). In some embodiments, $B_p$ is a phosphonocarboxylate moiety.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

The term "compound" or "conjugate" as used herein is meant to include all stereoisomers, geometric isomers, tautomers, and isotopes of the structures depicted. Compounds or conjugates herein identified by name or structure as one particular tautomeric form are intended to include other tautomeric forms unless otherwise specified.

Conjugates provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

All conjugates, and pharmaceutically acceptable salts thereof, can be found together with other substances such as water and solvents (e.g., hydrates and solvates) or can be isolated.

In some embodiments, preparation of conjugates can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the conjugates provided herein, or salts thereof, are substantially isolated. By "substantially isolated" is meant that the conjugate is at least partially or substantially separated from the environment in which it was formed or detected. Partial separation can include, for example, a composition enriched in the conjugates provided herein. Substantial separation can include compositions containing at least about 50%, at least about 60%, at least about 70%, at least about 80%, at least about 90%, at least about 95%, at least about 97%, or at least about 99% by weight of the conjugates provided herein, or salt thereof. Methods for isolating conjugates and their salts are routine in the art.

The expressions, "ambient temperature" and "room temperature" or "rt" as used herein, are understood in the art, and refer generally to a temperature, e.g. a reaction temperature, that is about the temperature of the room in which the reaction is carried out, for example, a temperature from about 20° C. to about 30° C.

The phrase "pharmaceutically acceptable" is employed herein to refer to those conjugates, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the conjugates described herein. As used herein, "pharmaceutically acceptable salts" refers to derivatives of the disclosed conjugates wherein the parent conjugate is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent conjugate formed, for example, from non-toxic inorganic or organic acids. The pharmaceutically acceptable salts of the present application can be synthesized from the parent conjugate which contains a basic or acidic moiety by conventional chemical methods. Generally, such salts can be prepared by reacting the free acid or base forms of these conjugates with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977). Conventional methods for preparing salt forms are described, for example, in *Handbook of Pharmaceutical Salts: Properties, Selection, and Use*, Wiley-VCH, 2002.

Unless specifically defined, conjugates provided herein can include all isotopes of atoms occurring in the intermediates or final conjugates. Isotopes include those atoms having the same atomic number but different mass numbers. Unless otherwise stated, when an atom is designated as an isotope or radioisotope (e.g., deuterium, [$^{11}$C], or [$^{18}$F]), the atom is understood to comprise the isotope or radioisotope in an amount at least greater than the natural abundance of the isotope or radioisotope. For example, when an atom is designated as "D" or "deuterium", the position is understood to have deuterium at an abundance that is at least 3000 times greater than the natural abundance of deuterium, which is 0.015% (i.e., at least 45% incorporation of deuterium). Synthetic methods for incorporating radioisotopes into organic compounds are well known in the art, and one of ordinary skill in the art will readily recognize methods applicable for the conjugates provided herein.

Methods of Treatment

The present application further provides methods of treating a disease in a subject in need thereof. As used herein, the term "subject," refers to any animal, including mammals. For example, mice, rats, other rodents, guinea pigs, rabbits, dogs, cats, swine, cattle, sheep, horses, primates, and humans. In some embodiments, the subject is a human.

In some embodiments, the method is a method of treating a disease or disorder of the middle ear and/or inner ear in a subject, comprising administering to the subject a therapeutically effective amount of a conjugate provided herein (e.g. a conjugate of Formula I), or a pharmaceutically acceptable salt thereof.

In some embodiments, the administration is localized in the ear. In some embodiments, the administration is localized in the middle ear or inner ear. In some embodiments, the administration is localized in the inner ear. In some embodiments, the conjugate administered to the inner ear comprises a therapeutic agent (i.e., group D of Formula I) selected from the group consisting of a regenerative molecule, a steroid, and an epigenetic modifier provided herein. In some embodiments, the administration is localized in the cochlea or semicircular canal. In some embodiments, the administration is localized in the middle ear. In some embodiments, the conjugate administered to the middle ear comprises a therapeutic agent (i.e., group D of Formula I) selected from the group consisting of an antibiotic, a steroid, a chemotherapeutic agent, and an immunotherapy agent provided herein. In some embodiments, the administration is localized in the space medial to the tympanic membrane and defined by the epi-, meso-, and hypotympanum. In some embodiments, the administration is localized at the round window membrane.

In some embodiments, the disease or disorder of the middle ear and/or inner ear is selected from the group consisting of vestibular schwannoma, hearing loss, otitis media, cancer of the middle ear and/or inner ear, Meniere's disease, osteoporosis, Paget's disease, osteogenesis, osteomyelitis, otosclerosis, an autoimmune middle ear and/or inner ear disease, benign paroxysmal positional vertigo (BPPV), bilateral vestibular hypofunction, labyrinthitis, vestibular neuritis, secondary endolymphatic hydrops (SEH), tinnitus, vestibular hyperacusis, and vertebrobasilar insufficiency (VBI).

In some embodiments, the autoimmune middle ear and/or inner ear disease is selected from the group consisting of Cogan's syndrome, relapsing polychondritis, polyarteritis nodosa, Wegener's granulomatosis, systemic lupus erythematosus, ulcerative colitis, Sjogren's syndrome, and rheumatoid arthritis.

In some embodiments, the cancer of the middle ear and/or inner ear is selected from the group consisting of squamous cell carcinoma, basal cell cancer, melanoma, adenoid cystic carcinoma, and adenocarcimona.

In some embodiments, the hearing loss comprises sudden sensorineural hearing, autoimmune hearing loss, or noise-induced hearing loss.

In some embodiments, the otitis media is acute otitis media (AOM) or otitis media with effusion (OME).

In some embodiments, the disease or disorder is associated with abnormal activity or dysregulation of one or more Tropomyosin receptor kinases. In some embodiments, the Tropomyosin receptor kinase is TrkB or TrkC. In some embodiments, the Tropomyosin receptor kinase is TrkB. In some embodiments, the Tropomyosin receptor kinase is TrkC. In some embodiments, the disease or disorder is associated with abnormal activity or dysregulation of spiral ganglion neuron cells.

The present application further provides methods of modulating one or more Tropomyosin receptor kinases (Trk(s)), comprising contacting the one or more Tropomyosin receptor kinases with a conjugate provided herein (e.g., a conjugate of Formula I). In some embodiments, the Tropomyosin receptor kinase is TrkB.

Tropomyosin receptor kinase is TrkC. In some embodiments, the contacting modulates TrkB and TrkC. In some embodiments, the modulating is activating.

As used herein, the term "contacting" refers to the bringing together of indicated moieties in an in vitro system or an in vivo system. For example, "contacting" a Tropomyosin receptor kinase with a conjugate provided herein includes the administration of a conjugate of the present invention to subject, such as a human, having a Tropomyosin receptor kinase, as well as, for example, introducing a conjugate provided herein into a sample containing a cellular or purified preparation containing the Tropomyosin receptor kinase.

One or more additional therapeutic agents such as, for example, a therapeutic agent provided herein, can be used in combination with a conjugate provided herein, or a pharmaceutically acceptable salt thereof, for treatment of the diseases or disorders provided herein.

As used herein, the phrase "therapeutically effective amount" refers to the amount of active compound (i.e., a conjugate of Formula I) or pharmaceutical agent that elicits the biological or medicinal response that is being sought in a tissue, system, animal, individual or human by a researcher, veterinarian, medical doctor or other clinician. In some embodiments, the dosage of the conjugate, or a pharmaceutically acceptable salt thereof, administered to a subject or individual is about 1 mg to about 2 g, about 1 mg to about 1000 mg, about 1 mg to about 500 mg, about 1 mg to about 100 mg, about 1 mg to 50 mg, or about 50 mg to about 500 mg.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or reducing or alleviating one or more symptoms of the disease.

Pharmaceutical Compositions

When employed as pharmaceuticals, the conjugates provided herein can be administered in the form of pharmaceutical compositions. These compositions can be prepared as described herein or elsewhere, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, (e.g., intrathecal or intraventricular, administration). Parenteral administration can be in the form of a single bolus dose, or may be, for example, by a continuous perfusion pump. In some embodiments, the conjugates provided herein (e.g., conjugates of Formula I, or a pharmaceutically acceptable salt thereof) are suitable for parenteral administration. In some embodiments, the conjugates provided herein are suitable for intravenous administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. In some embodiments, the pharmaceutical compositions provided herein are suitable for parenteral administration. In some embodiments, the compositions provided herein are suitable for intravenous administration.

Also provided are pharmaceutical compositions which contain, as the active ingredient, a conjugate provided herein, or a pharmaceutically acceptable salt thereof, in combination with one or more pharmaceutically acceptable carriers (excipients). In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

The active conjugate can be effective over a wide dosage range and is generally administered in a pharmaceutically effective amount, for example, from about 1 µg to about 500 mg, from about 1 µg to about 250 mg, from about 1 µg to about 100 mg, from about 1 µg to about 50 mg, from about 1 µg to about 10 mg, from about 1 µg to about 1 mg, from about 1 µg to about 500 µg, from about 1 µg to about 250 µg, from about 1 µg to about 100 µg, from about 1 µg to about 50 µg, from about 1 µg to about 10 µg, from about 10 µg to about 500 mg, from about 10 µg to about 250 mg, from about 10 µg to about 100 mg, from about 10 µg to about 50 mg, from about 10 µg to about 10 mg, from about 10 µg to about 1 mg, from about 10 µg to about 500 µg, from about 10 µg to about 250 µg, from about 10 µg to about 100 µg, from about 10 µg to about 50 µg, from about 50 µg to about 500 mg, from about 50 µg to about 250 mg, from about 50 µg to about 100 mg, from about 50 µg to about 50 mg, from about 50 µg to about 10 mg, from about 50 µg to about 1 mg, from about 50 µg to about 500 µg, from about 50 µg to about 250 µg, from about 50 µg to about 100 µg, from about 100 µg to about 500 mg, from about 100 µg to about 250 mg, from about 100 µg to about 100 mg, from about 100 µg to about 50 mg, from about 100 µg to about 10 mg, from about 100 µg to about 1 mg, from about 100 µg to about 500 µg, from about 100 µg to about 250 µg, from about 250 µg to about 500 mg, from about 250 µg to about 250 mg, from about 250 µg to about 100 mg, from about 250 µg to about 50 mg, from about 250 µg to about 10 mg, from about 250 µg to about 1 mg, from about 250 µg to about 500 µg, from about 500 µg to about 500 mg, from about 500 µg to about 250 mg, from about 500 µg to about 100 mg, from about 500 g to about 50 mg, from about 500 µg to about 10 mg, from about 500 µg to about 1 mg, from about 1 mg to about 500 mg, from about 1 mg to about 250 mg, from about 1 mg to about 100 mg, from about 1 mg to about 50 mg, from about 1 mg to about 25 mg, from about 1 mg to about 10 mg, from about 1 mg to about 5 mg. from about 5 mg to about 500 mg, from about 5 mg to about 250 mg, from about 5 mg to about 100 mg, from about 5 mg to about 50 mg, from about 5 mg to about 25 mg, from about 5 mg to about 10 mg, from about 10 mg to about 500 mg, from about 10 mg to about 250 mg, from about 10 mg to about 100 mg, from about 10 mg to about 50 mg, from about 10 mg to about 25 mg, from about 25 mg to about 500 mg, from about 25 mg to about 250 mg, from about 25 mg to about 100 mg, from about 25 mg to about 50 mg, from about 50 mg to about 500 mg, from about 50 mg to about 250 mg, from about 50 mg to about 100 mg, from about 100 mg to about 500 mg, from about 100 mg to about 250 mg, or from about 250 mg to about 500 mg. It will be understood, however, that the amount of the conjugate actually administered will usually be determined by a physician, according to the relevant circumstances, including the condition to be treated, the chosen route of administration, the actual conjugate administered, the age, weight, and response of the individual subject, the severity of the subject's symptoms, and the like.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

Example 1. Synthesis of DHF-Linker-RIS

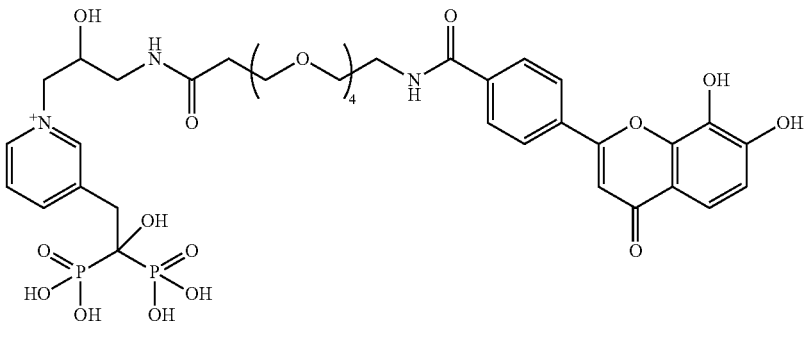

DHF-linker-RIS

The title conjugate was prepared according to the procedure described in Scheme 3a. The final DHF-linker-RIS conjugate was purified using reversed-phase (RP), gradient C18 HPLC on a C18 (21.2 mm×250 mm, 5μ, 100 Å pore size) column, flow rate 8.0 mL/min, using 10% MeCN 0.1 N TEAC (pH 7.0) as buffer A and 75% MeCN 0.1 N TEAC (pH 7.8) as buffer B with the gradient increasing to 40% of buffer B for 25 minutes, then 100% of Buffer B for 75 minutes. UV detection was set at 260 nm. Characterization of the compound was performed using mass spectrometry, $^1$H NMR, and $^{31}$P NMR spectroscopy.

$^1$H NMR (400 MHz, D$_2$O) δ 8.68 (s, 1H), 8.54-8.39 (m, 2H), 8.19-7.90 (m, 1H), 7.79 (s, 1H), 7.11 (d, J=8.4 Hz, 1H), 6.75 (d, J=8.6 Hz, 0H), 6.47 (s, 0H), 4.31-4.18 (m, 1H), 4.06 (s, 1H), 3.62-3.10 (m, 20H), 2.32 (s, 2H); $^{31}$P{$^1$H} NMR (162 MHz, D$_2$O) δ 15.3-18.6 (br, 2P).

ESI-MS: calcd for $C_{37}H_{48}N_3O_{18}P_2^+$: 884.74 m/z; found 882.4 [M$^-$] m/z.

Example 2. Synthesis of 1Aa-Linker-Zoledronate (ZOL)

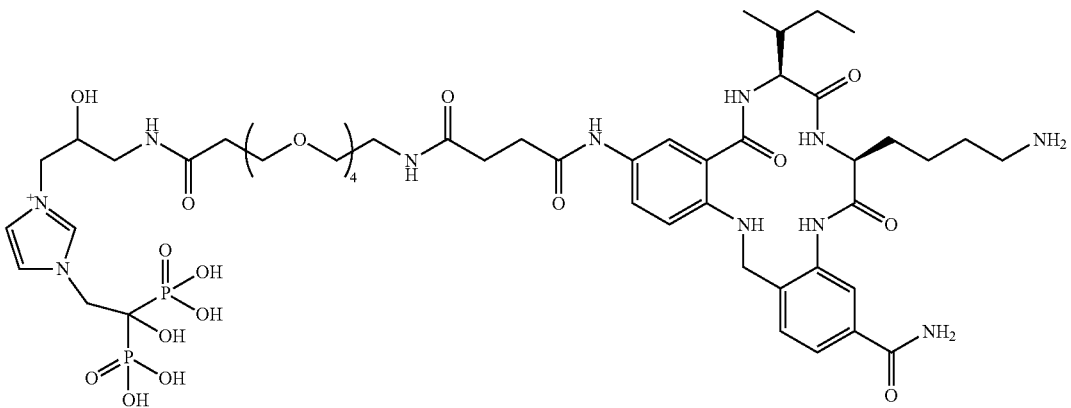

1Aa-linker-ZOL

The title conjugate was prepared according to the procedure described in Scheme 4. (7 S, 10 S)-4-amino-7-(4-aminobutyl)-10-((S)-sec-butyl)-6,9,12-trioxo-5,6,7,8,9,10,11,12,17,18-decahydrodibenzo[h,1][1,4,7,11]tetraazacyclotetradecine-3-carboxamide, designated as 1Aa, is a peptidomimetic that exhibits high neurotrophic activities. The synthesis of 1Aa-linker-ZOL using both cleavable and noncleavable linkages was achieved using the approach described in Scheme 4. The synthesis was performed with a ZOL analogue (ZOL linker) and a ZOL derivative of N-Boc-protected 1Aa containing a carboxylic moiety that allows further conjugation.

Example 3. Synthesis of Ciprofloxacin-Linker-ZOL

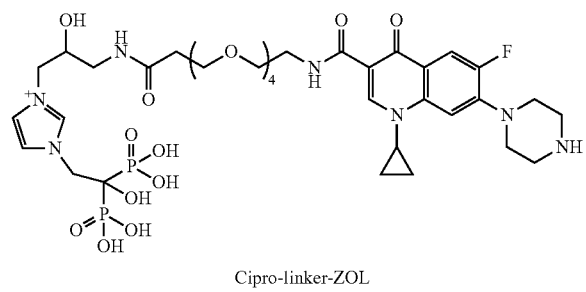

Cipro-linker-ZOL

The title conjugate was prepared according to the procedure described in Scheme 5. Ciprofloxacin is a member of quinolone family. It is commonly used to treat ear infections. As mentioned above, extra protection of the parent drug may be needed before conjugation is performed. In this case, Boc protection of the amino group in ciprofloxacin was performed, followed by conjugation with PEG linker and ZOL linker, respectively as shown in Scheme 5. The final product was obtained via Boc deprotection of the amino group.

Example 4. Synthesis of 6-FAM-ZOL

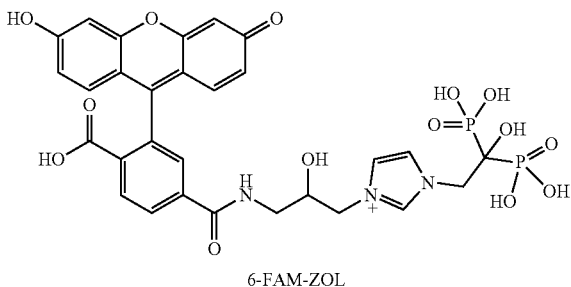 [SMILES: O=C(NCC(O)C[n+]1ccn(CC(O)(P(=O)(O)O)P(=O)(O)O)c1)c1ccc(C(=O)O)c(-c2c3ccc(=O)cc-3oc3cc(O)ccc23)c1]

6-FAM-ZOL

Zoledronate was purchased from Molekula Limited, UK; 5(6)-carboxyfluorescein, succinimidyl ester was purchased from Invitrogen, CA, USA. 6-FAM-ZOL was synthesized as described previously (see e.g., Kashemirov et al, *Bioconjug. Chem.* 2008; 19:2308-10; and Sun et al, *Phosphorous Sulfur Silicon Relat. Elem.* 2011, 186:970-971). The synthesis is based on attachment of a functionalized epoxide linker to the imidazolyl nitrogen of zoledronate under mild reaction conditions (e.g., aqueous solution, near neutral pH, about 21-40° C.). The resulting drug-linker intermediate has an amino group available for reaction with 5(6)-carboxyfluorescein, succinimidyl ester in the next step. The final conjugate, 6-FAM-ZOL, was isolated by HPLC (purity >95%) and fully characterized by $^1$H, $^{31}$P NMR, HRMS, UV-VIS and fluorescent spectroscopy. 6-FAM-ZOL binds to hydroxyapatite with approximately 70% affinity relative to native zoledronate (see e.g., Sun et al, *Chemistry*. Los Angeles: University of Southern California, 2013).

Example 5. General Methods—Guinea Pig Model

Animals

Male albino guinea pigs (Hartley strain; Charles River Laboratories, Inc., Wilmington, Mass.), each weighing approximately 350 g, were used. Nembutal (12.5 mg/kg intraperitoneally), Fentanyl (0.1 mg/kg intramuscularly), and Droperidol (5 mg/kg intramuscularly) were given for anesthesia. Supplemental doses of 0.7 mg/kg Fentanyl and 3.0 mg/kg Droperidol alternating with 6.25 mg/kg Nembutal were administered as needed. Animals were euthanized using pentobarbital (Fatal-Plus) at 390 mg/kg. The Massachusetts Eye and Ear Infirmary Institutional Animal Care and Use Committee approved all procedures.

Hearing Measurements

Acoustic stimuli were digitally generated and auditory responses were monitored using a National Instruments PXI stimulus generation/data acquisition system, which included a 24 bit digital I-O board (PXI-4461) and a 16 bit digital I-O board (PXI-6221) and the Eaton Peabody Laboratories Cochlear Function Test Suite. To elicit the auditory brainstem responses (ABRs) and the compound action potentials (CAPs), 5 ms tone pip stimuli were used with 0.5 ms rise/fall times (cosine squared) in alternating polarity at 33/s.

Acoustic stimuli were delivered via a custom acoustic assembly comprising two dynamic drivers as sound sources and a miniature electret microphone to measure sound pressure in situ (for a complete description, see e.g., http://www.masseyeandear.org/research/otolaryngology/investigators/laboratories/eaton-peabody-laboratories/epl-engineering-resources). The response from the electrodes was amplified (10,000×), filtered (0.3-3 kHz bandpass), and averaged (512 samples at each frequency-level combination for ABRs and 128 samples for CAPs).

ABRs were recorded via subdermal needle electrodes (vertex-ventrolateral to the pinna of the test ear with a ground at the base of the tail). The CAPs electrode was located near the round window niche. Sound level was incremented in 5 dB steps, from ~10 dB below threshold to 90 dB sound pressure level (SPL). Threshold for ABRs and CAPs was defined as the lowest stimulus level at which a repeatable wave could be identified in the response waveform.

Distortion product otoacoustic emissions (DPOAEs) were recorded for primary tones (f1, f2) over the same f2 range of frequencies, with a frequency ratio of 1.2, and with the level of the f2 primary 10 dB less than f1 level. Primaries were incremented together in 5 dB steps from ~10 dB below threshold to 80 dB SPL. Ear-canal sound pressure was amplified and digitally sampled, FFTs were computed and averaged, and the 2f1-f2 DPOAE and surrounding noise floor were extracted. Iso-response contours were interpolated from plots of response amplitude vs. sound level. Threshold is defined as the f1 level required to produce a DPOAE of −5 dB SPL.

Distortion product otoacoustic emissions (DPOAEs) and auditory brainstem responses (ABRs) were measured in the systemic and round window membrane (RWM) delivery experiments. For the cochleostomy experiments, compound action potentials (CAPs) from the auditory nerve were substituted for ABRs. Hearing was measured at 2.78, 4, 5.6, 8, 12, 16, 24, and 32 kHz.

Timing of Analyses

In humans, bone deposition and renal excretion rapidly clear zoledronate from plasma, with two half-lives at 0.2 and 1.4 hours, and less than 1% of the drug remaining in plasma after 24 hours (see e.g., Chen et al, *J. Clin. Pharmacol.* 2002, 42:1228-36). All animals were therefore analyzed after maximal bisphosphonate deposition. Systemic delivery animals were analyzed at 48 hrs to account for potential differences between IP (our system) and IV (human) delivery. Round window delivery animals were analyzed at 3 weeks to allow middle ear inflammation to subside prior to hearing analysis and to account for transit across the RWM. Intracochlear delivery animals were analyzed at 3 hours as this timepoint allowed for high levels of delivery while avoiding the potential long-term effects of a cochleostomy.

Specimen Processing

The inner ears were harvested and stripped of soft tissue. All subsequent steps were performed in covered vials to prevent 6-FAM-ZOL bleaching. Specimens were fixed in an excess volume of neutral buffered formalin (10%, Fisher Scientific, Pittsburgh Pa.) at room temperature for 24 hours. The neutral buffered formalin was changed and fixation continued for another 24 hours. To prepare for resin embedding, specimens were dehydrated in an ascending series of ethanol (Fisher Scientific, 24 hr at 70%, 1 hr at 70%, 1 hr at 85%, 0.5 hr at 95%, 0.5 hr at 100%) followed by a wash in xylene (Fisher Scientific) and a 15 minute immersion in xylene. Specimens were cleared of xylene by a 1 hour infiltration in methyl methacrylate (MMA, Acrylosin soft, Dorn and Hart, Villa Park, Ill.) under vacuum. The MMA solution was changed and samples were infiltrated for 24 hours under vacuum. The infiltration solution was changed and the process was repeated for another 24 hours. Specimens were embedded in a solution of MMA containing 0.25% w/v (2.5 g/L) of perkadox-16 (Dorn and Hart) for several hours under vacuum. After several hours, specimens were sealed in 50 mL polypropylene tubes and maintained at room temperature in a heat sink until fully cured (approximately 5 days).

Sections were prepared for fluorescent imaging by orienting and grinding the sample surface to the level of the mid-modiolus. Surfaces were polished on a 12" table mounted rotary wheel using water and a progressively finer series of silicon carbide abrasive papers ending with 2400 grit (Buehler, Lake Bluff, Ill.). The methyl methacrylate embedding material possessed excellent optical clarity, which, in combination with the high level of polishing, resulted in a transparent interface for imaging.

6-FAM-ZOL Quantification and Data Normalization

High-resolution images (1360 by 1024; 16 bit) were taken under FITC illumination (470/40 excitation, 495 lp dicroic; 525/50 emission) using a Carl Zeiss Axiovert 200 Inverted Microscope. ImageJ (Rasband WS, ImageJ, United States National Institutes of Health, Bethesda, Md., USA, 1997-2014) was used to quantify the amount of fluorescence within the cochlear wall and modiolus at each half-turn, as shown in FIG. 1. Background fluorescence, defined as the average amount of fluorescence in an area of the resin block containing no sample, was subtracted from all measurements. Fluorescence remained stable over at least two weeks after grinding if samples were kept in the dark at room temperature. Some images were also collected using a Leica TCS-SP2 confocal microscope. Confocal images were collected over a depth of 500 µm to generate maximum fluorescence images.

Statistical Analysis

Statistical data analysis was performed using the SAS software package. Null hypotheses were rejected at p>0.05.

Mixed model analysis of variance was used to analyze the effect of dose on fluorescent response in the cochlea. A separate model was fit for each experiment. The model included a fixed effect of dose and a random effect of dose within each replicate. For each dose level the reported estimated response is the model based least squares mean and standard error of the mean.

Mixed model analysis of variance was used to analyze the effect of dose on fluorescent response in the tibia. The model included a fixed effect of dose and a random intercept within each replicate. For each dose level the reported estimated response is the model based least squares mean and standard error of the mean.

Mixed model analysis of variance was used to analyze the effect of location on fluorescent response in the cochlea. A separate model was fit for each experiment. The model included a fixed effect of dose and location and a random effect of location within each replicate by dose level.

Example 6. Systemic Drug Delivery: Intraperitoneal 6-FAM-ZOL Injection in a Guinea Pig Model Doses of 6-FAM-ZOL were administered that corresponded by molar weight to either one or three times the human systemic dose (5 mg injection) of zoledronate recommended for osteoporosis. 6-FAM-ZOL was diluted into 1 mL of artificial perilymph (AP) or phosphate buffered saline (PBS) for injection at 0.185 mg/kg (i.e., 1×6-FAM-ZOL dose) and 0.555 mg/kg (i.e., 3×6-FAM-ZOL dose). AP and PBS were both used as carriers in different experiments and no differences were observed. Animals were anesthetized and a 0.5 cm incision was made in the abdomen through which 6-FAM-ZOL was injected into the peritoneum. We injected 1 mL of vehicle alone, either AP or PBS, in the control animals. All guinea pigs underwent DPOAEs and ABRs both at the time of treatment and immediately before being sacrificed. Four independent experiments, each with one vehicle-only control, one 1× dose animal, and one 3× dose animal, were performed with AP and three independent experiments with PBS. The content of the AP was as follows: 130 mM NaCl, 3.5 mM KCl, 1.5 mM $CaCl_2$, 5.5 mM glucose, 20 mM HEPES, and pH 7.4. PBS was as follows: 137 mM NaCl, 2.7 mM KCl, 10 mM $Na_2HPO_4$, 1.8 mM $KH_2PO_4$, and pH 7.4).

Figure 2A:
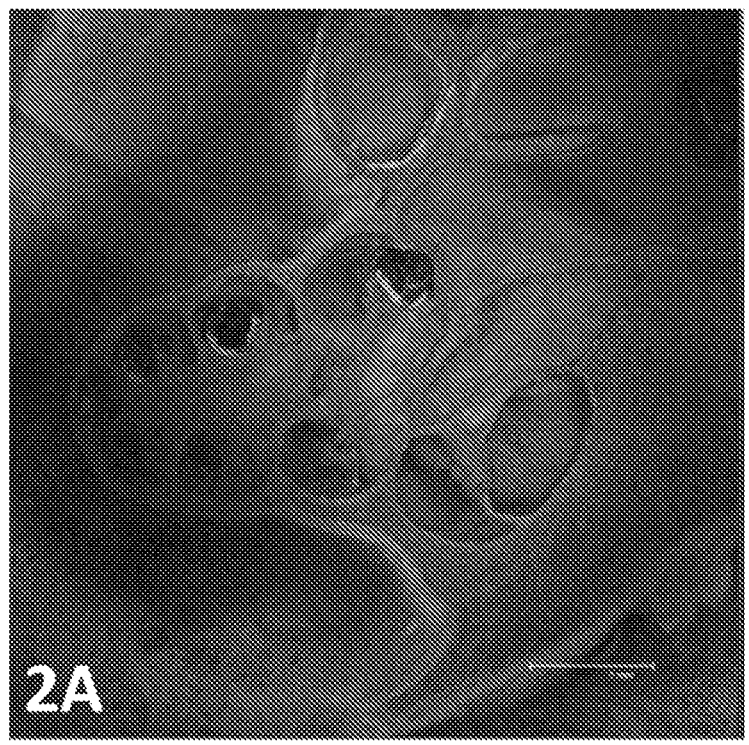
FIG. 2A shows fluorescent photomicrographs taken at mid-modiolar cochlear for untreated cochlea in a guinea pig. Scale bar is 1 mm.
Figure 2B:
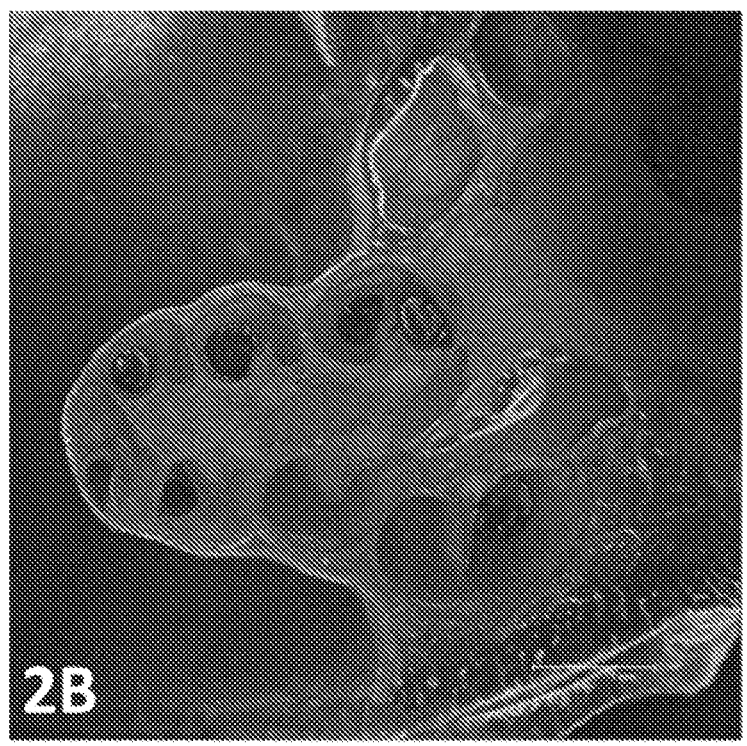
FIG. 2B shows fluorescent photomicrographs taken at mid-modiolar cochlear sections for treatment with 1× the human zoledronate dose (by molar mass) in a guinea pig. Scale bar is 1 mm.
Figure 2C:
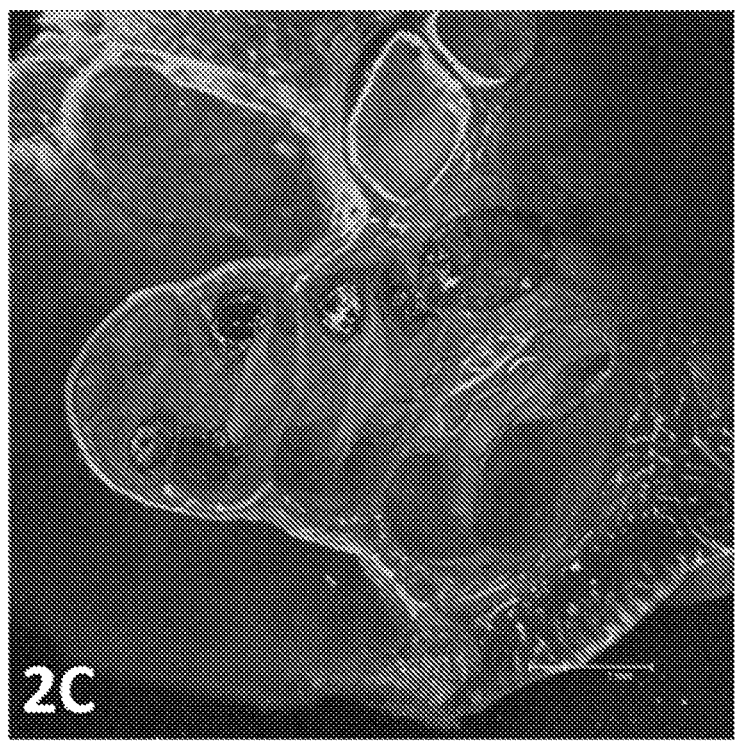
FIG. 2C shows fluorescent photomicrographs taken at mid-modiolar cochlear sections for treatment with 3× the human zoledronate dose (by molar mass) in a guinea pig. Scale bar is 1 mm.
Figure 2D:
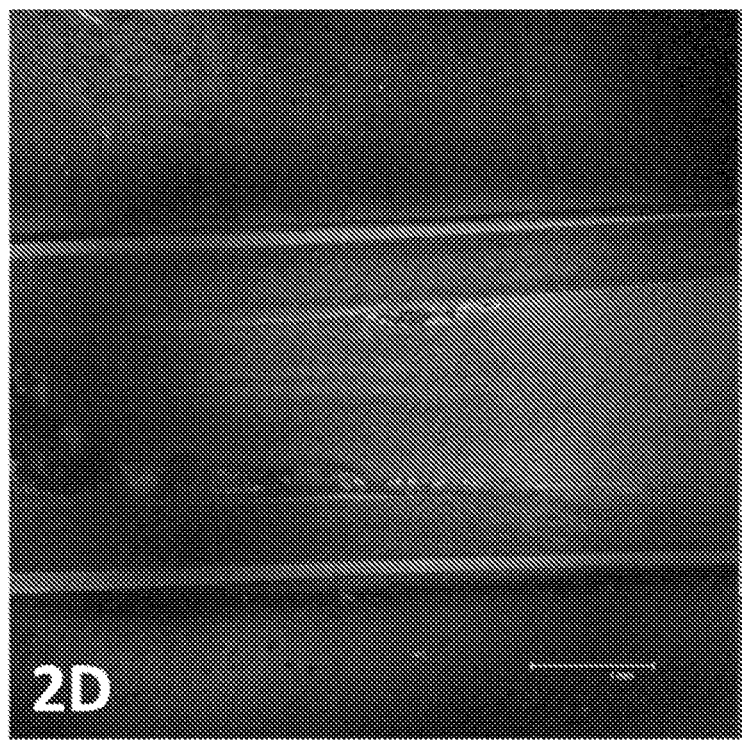
FIG. 2D shows fluorescent photomicrographs of tibial sections for untreated tibia in a guinea pig. Scale bar is 1 mm.
Figure 2E:
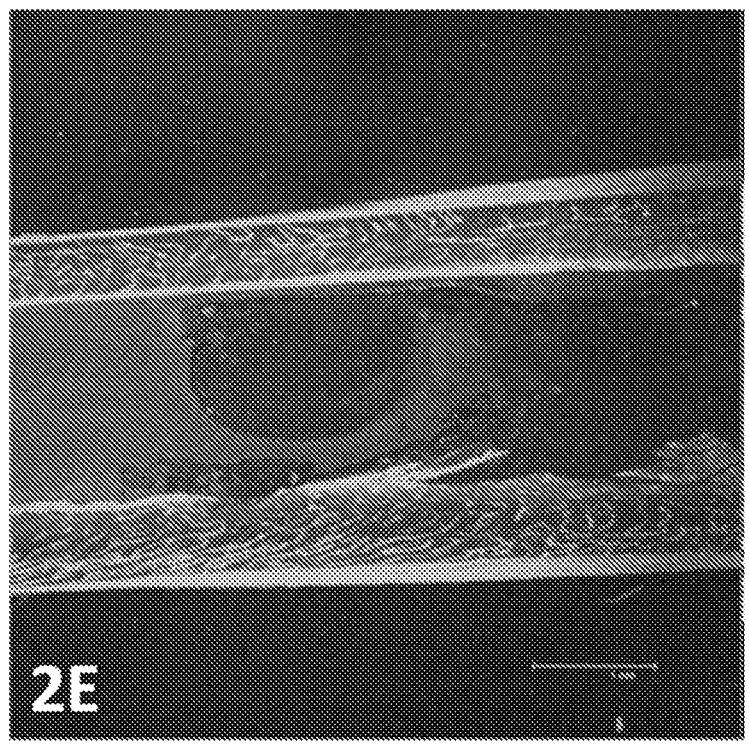
FIG. 2E shows fluorescent photomicrographs of tibial sections for treatment with 1× the human dose (by molar mass) in a guinea pig. Scale bar is 1 mm.
Figure 2F:
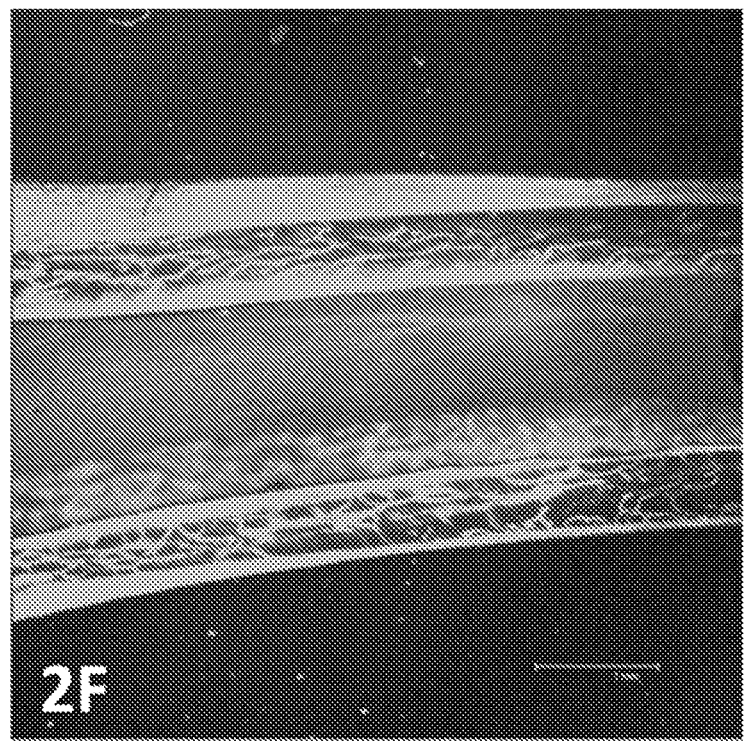
FIG. 2F shows fluorescent photomicrographs of tibial sections for treatment with 3× the human dose (by molar mass) in a guinea pig. Scale bar is 1 mm.
Figure 3A:
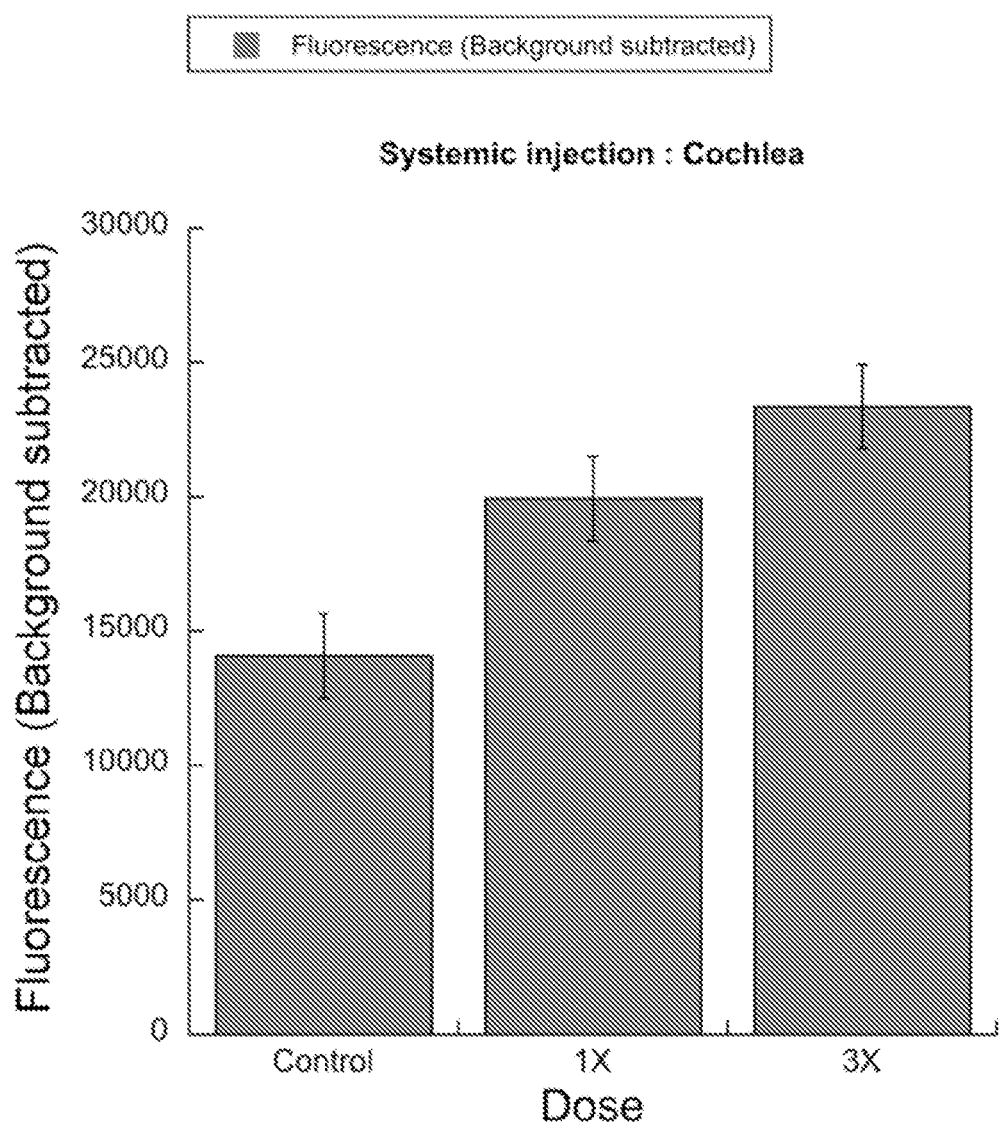
FIG. 3A shows quantification of fluorescence for cochleae following systemic 6-FAM-ZOL treatment in a guinea pig. Measurements were taken at each of six cochlear half-turns from base to apex and averaged.
Figure 3B:
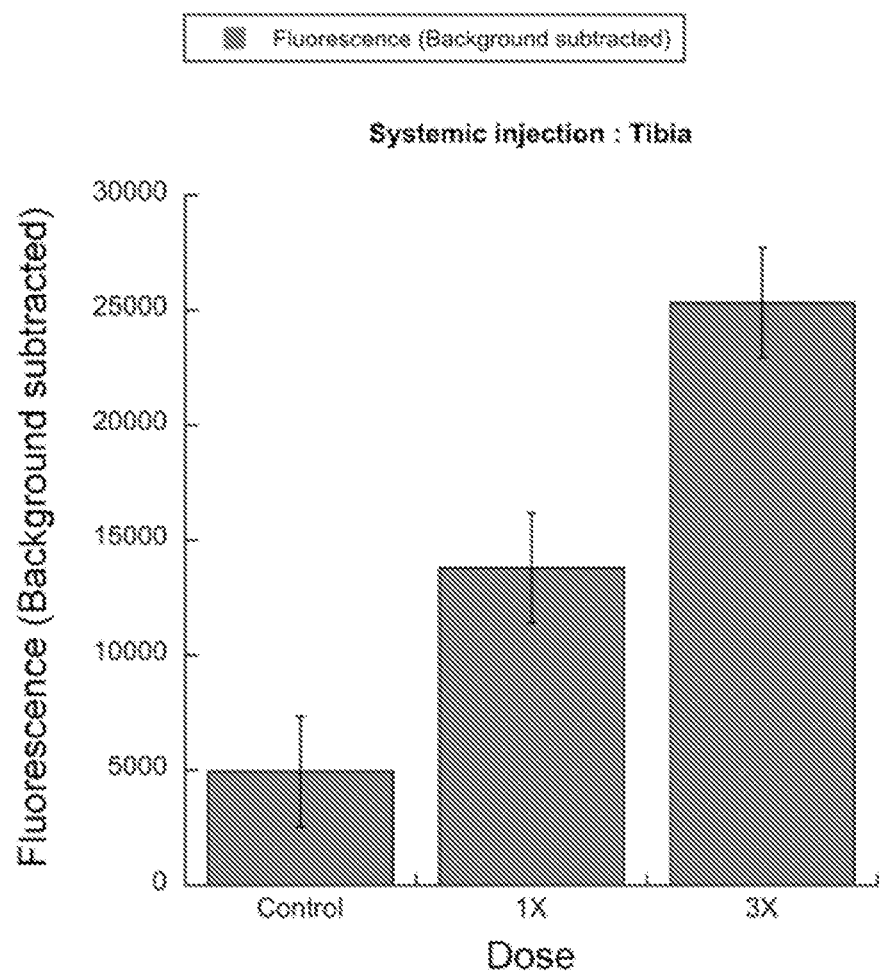
FIG. 3B shows quantification of fluorescence for tibiae following systemic 6-FAM-ZOL treatment in a guinea pig.
Figure 4A:
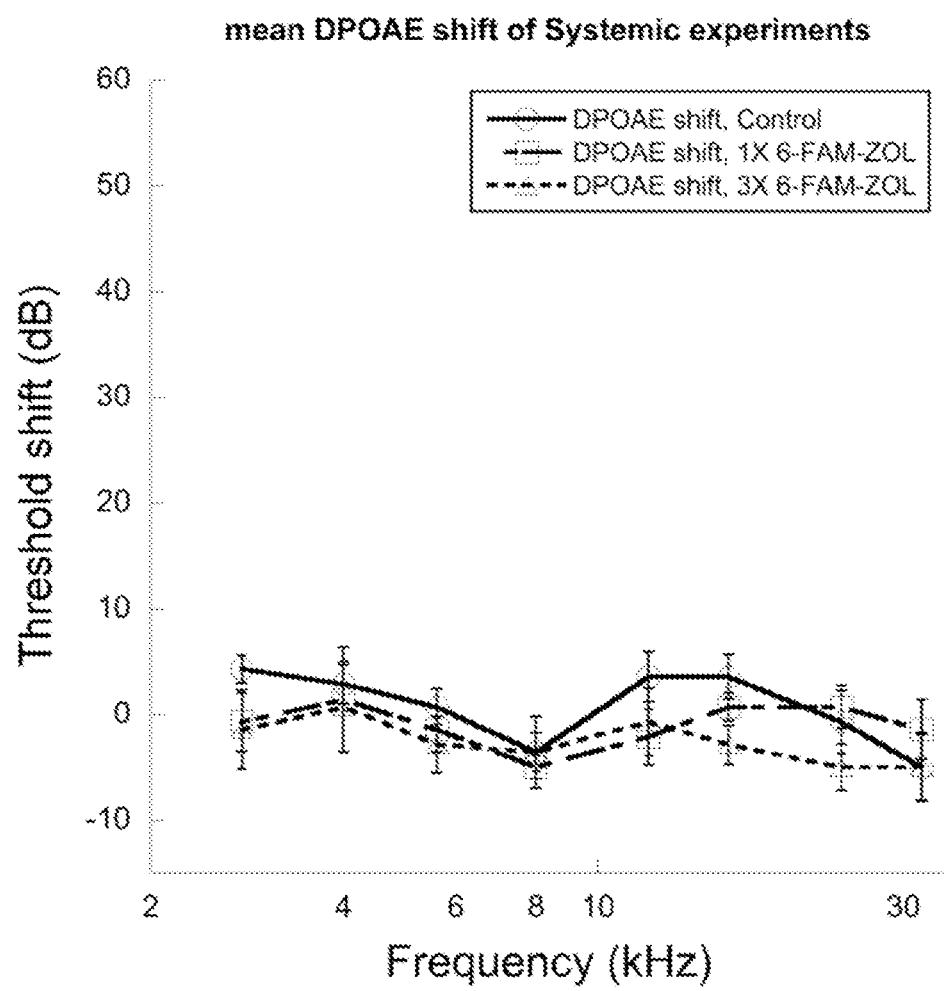
FIG. 4A shows the mean distortion product otoacoustic emission (DPOAE) shift of systemic experiments in a guinea pig.
Figure 4B:
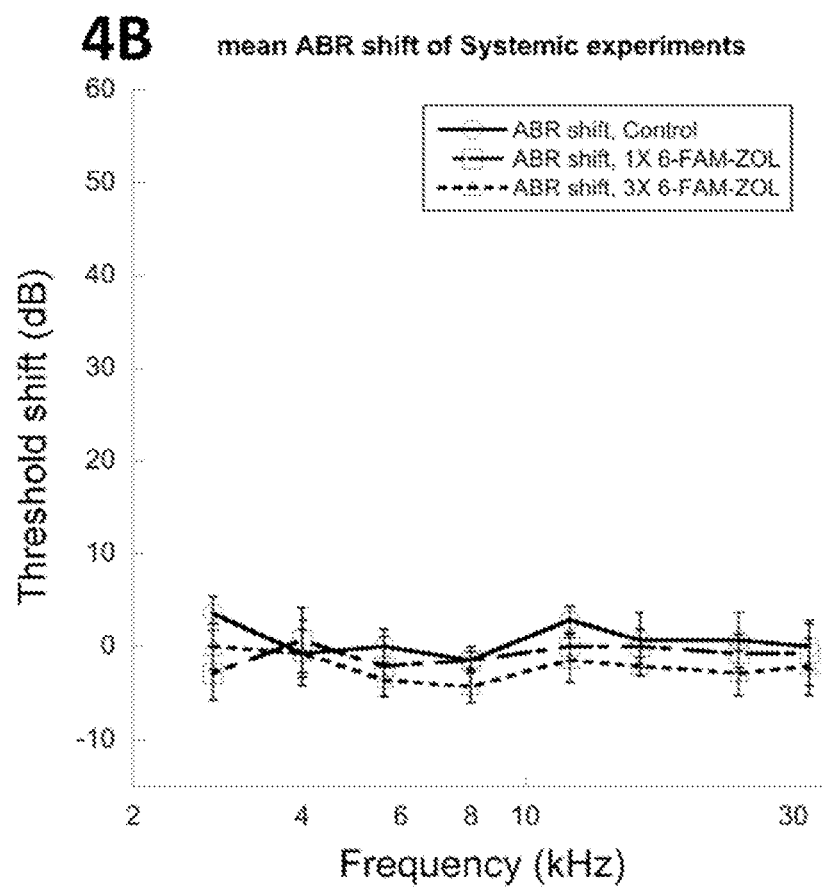
FIG. 4B shows the mean auditory brainstem response (ABR) shift of systemic experiments in a guinea pig.

Systemic zoledronate (6-FAM-ZOL) enters the bone of the cochlea. Because of the presence of the blood-cochlear barrier, it was first assessed whether or not systemically administered zoledronate efficiently enters the bone of the inner ear. To assess this, the deposition of systemically administered 6-FAM-ZOL in the otic capsule was compared with the deposition of 6-FAM-ZOL in the tibia. Fluorescent signal was observed above native cochlear autofluorescence in the lateral wall of cochleae derived from both 1× and 3×6-FAM-ZOL-treated animals as shown in FIGS. 2A-C. This fluorescence increased with dose and the differences were statistically significant, as shown in FIG. 3A. As a comparison with appendicular cortical bone, we also evaluated tibiae harvested from both control and 6-FAM-ZOL-treated animals. We readily detected bright fluorescent green signal within the tibiae of 6-FAM-ZOL-treated animals, as shown in FIGS. 2D-F. Again, differences between control, 1×, and 3×6-FAM-ZOL treatments were dose-dependent and statistically significant, as shown in FIG. 3B. Average fluorescence measurements were 50% stronger in tibiae compared to cochleae (approximately 5,800 fluorescence units above control vs 8,800 fluorescence units above control for the 1× systemic dose as shown in FIGS. 2 and 3. No significant physiological changes were observed by ABR and DPOAE, as shown in FIGS. 4A-B. It was concluded from these findings that systemic 6-FAM-ZOL treatment resulted in a non-ototoxic, dose-dependent increase in fluorescent signal within otic capsule bone and appendicular cortical bone, with more deposition in cortical bone than in otic capsule bone.

Example 7. Local Drug Delivery: Placement of 6-FAM-ZOL onto the RWM in a Guinea Pig Model A 2% (w/v) solution of sodium alginate was prepared in PBS and 10% (0.1×) and 30% (0.3×) of the human systemic dose by molar weight were tested. For 0.1×6-FAM-ZOL, 1.3 µL of 4 µg/µL 6-FAM-ZOL was mixed with 1.3 µL of 2% sodium alginate solution. For 0.3×6-FAM-ZOL, 1 µL of 15 µg/µL 6-FAM-ZOL was mixed with 1.3 µL of 2% sodium alginate solution. A few drops of 0.2 M $CaCl_2$ were placed over this mixture, which then formed a hydrogel with a diameter of 1-2 mm. Each hydrogel was prepared immediately before use. Five independent experiments were performed, each with one PBS control, one 0.1× treated animal, and one 0.3× treated animal (15 animals total).

The round window was visualized via a bullectomy approach and the beads were placed within the round window membrane (RWM) niche under direct microscopic visualization. Animals were sacrificed 3 weeks later, after middle ear inflammation from surgery had subsided. DPOAEs and ABRs were first measured while animals were under anesthesia prior to bullectomy and again prior to analysis.

Figure 5A:
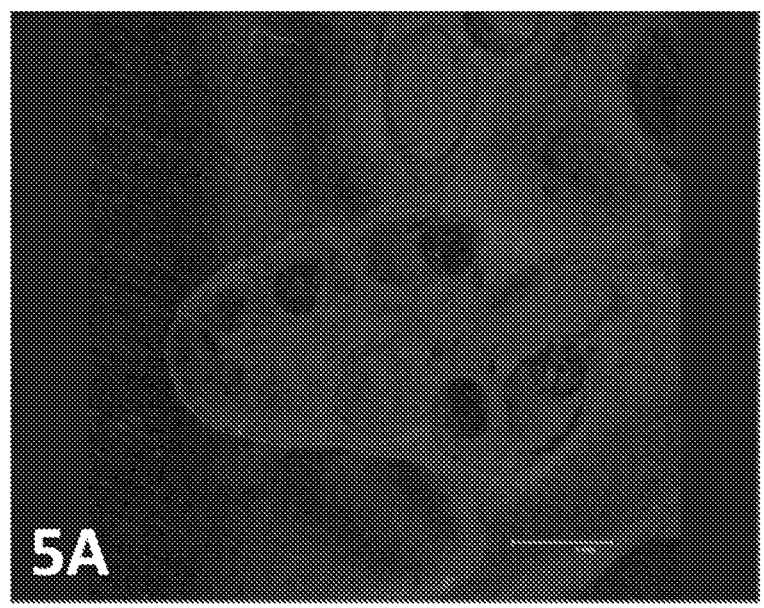
FIG. 5A shows fluorescent photomicrographs taken at mid-modiolar sections of the cochlea are shown for untreated cochlea in a guinea pig.
Figure 5B:
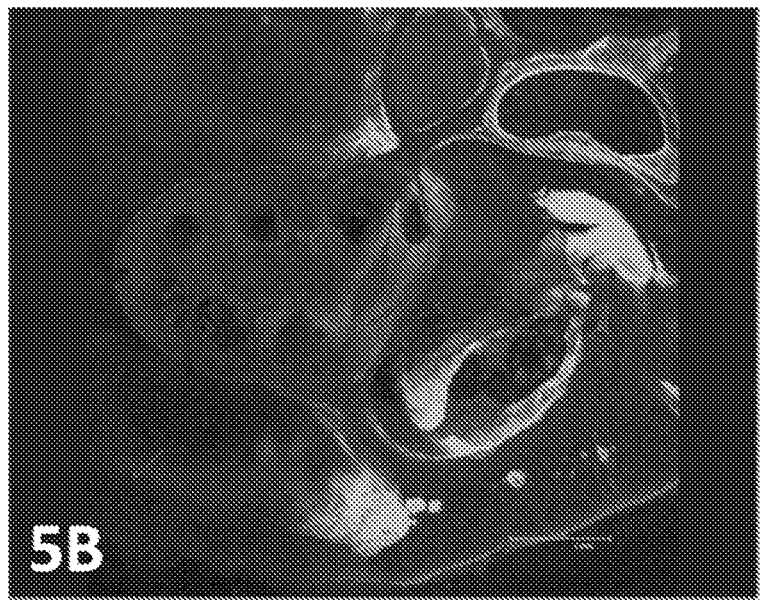
FIG. 5B shows fluorescent photomicrographs of cochlea taken at mid-modiolar sections after treatment with 10% of the 1× systemic dose of 6-FAM-ZOL in a guinea pig.
Figure 5C:
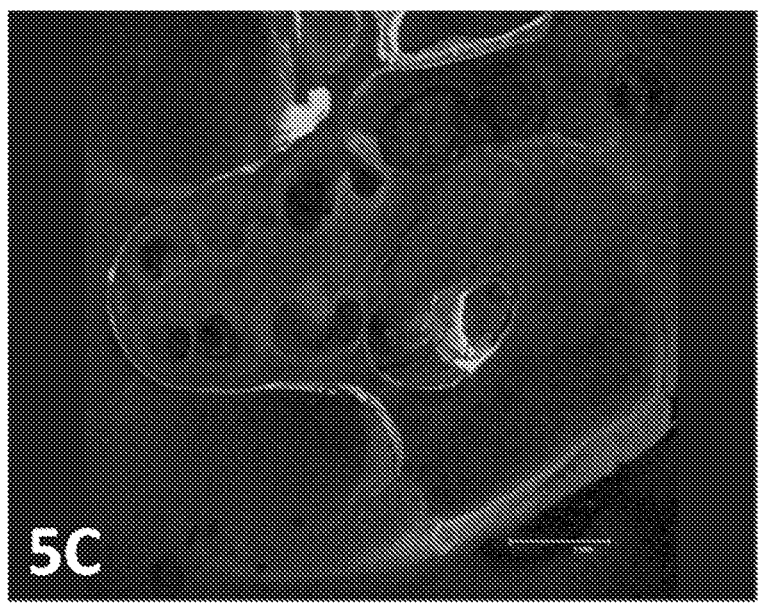
FIG. 5C shows fluorescent photomicrographs of cochlea taken at mid-modiolar sections after treatment with 30% of the 1× systemic dose in a guinea pig.
Figure 6A:
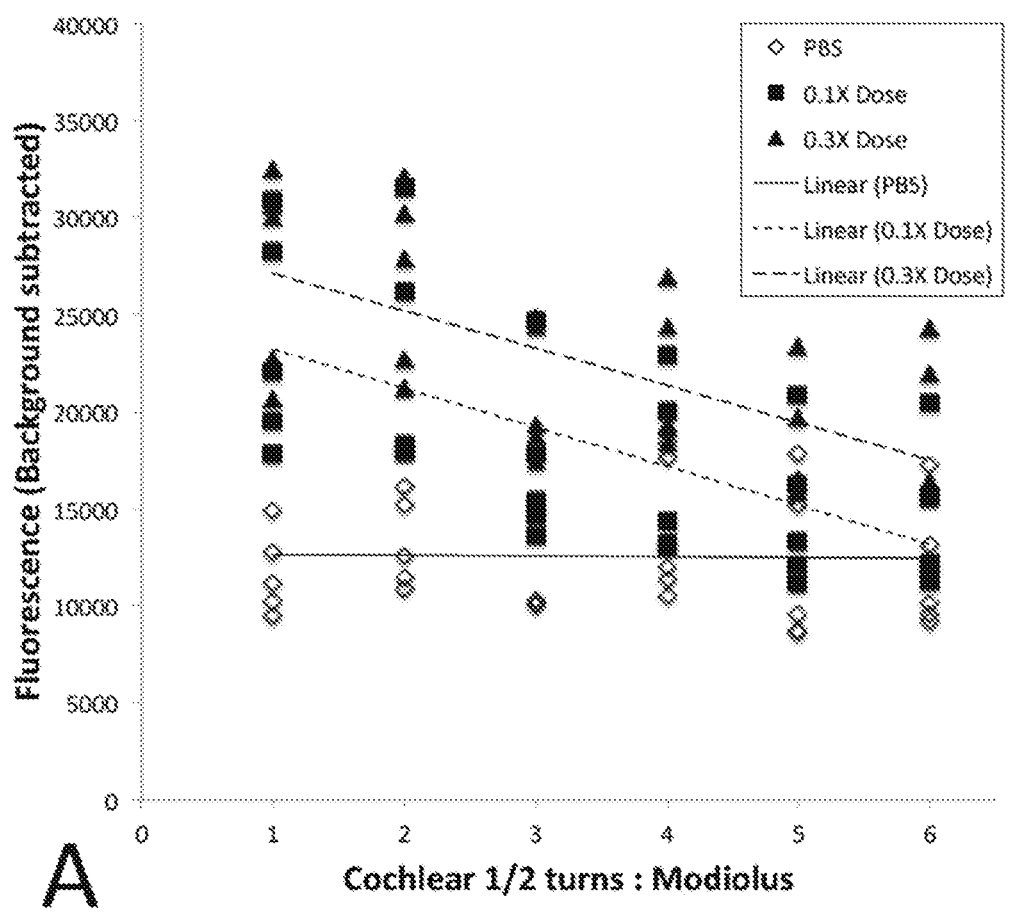
FIG. 6A shows quantification of fluorescence of cochlea following round window membrane (RWM) 6-FAM-ZOL treatment in a guinea pig. Measurements were taken at each of six cochlear half-turns from base to apex, along the modiolus. The p values for total average fluorescence between control and 1×, control and 3×, and 1× and 3× were 0.0040, 0.0001, and 0.0194, respectively. Slopes of the 0.1× and 0.3× regression lines were significantly different from the slope of the control along the modiolus ($p<0.0001$).
Figure 6B:
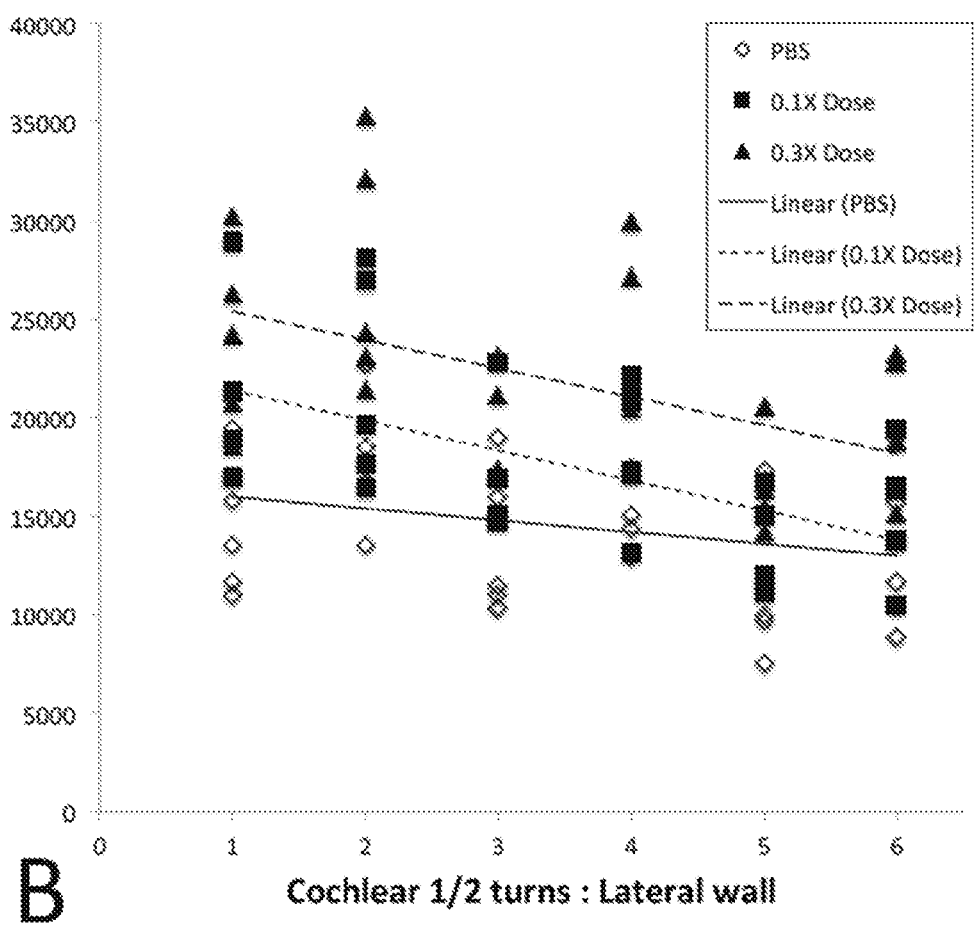
FIG. 6B shows quantification of fluorescence along the lateral wall following RWM 6-FAM-ZOL treatment in a guinea pig. The p values for total average fluorescence between control and 0.1×, control and 0.3×, and 0.1× and 0.3× were 0.018, 0.0001, and 0.0038, respectively. The slopes were not significantly different ($p=0.09$).
Figure 7A:
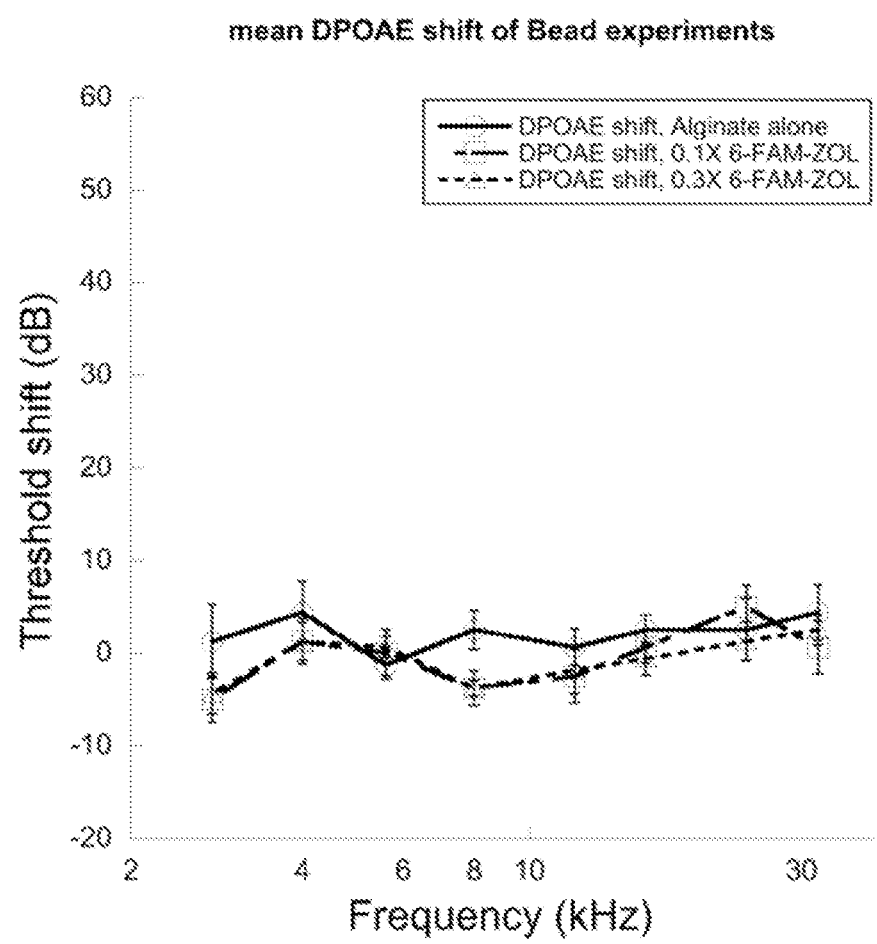
FIG. 7A shows the mean DPOAE shift of Bead experiments in a guinea pig model.
Figure 7B:
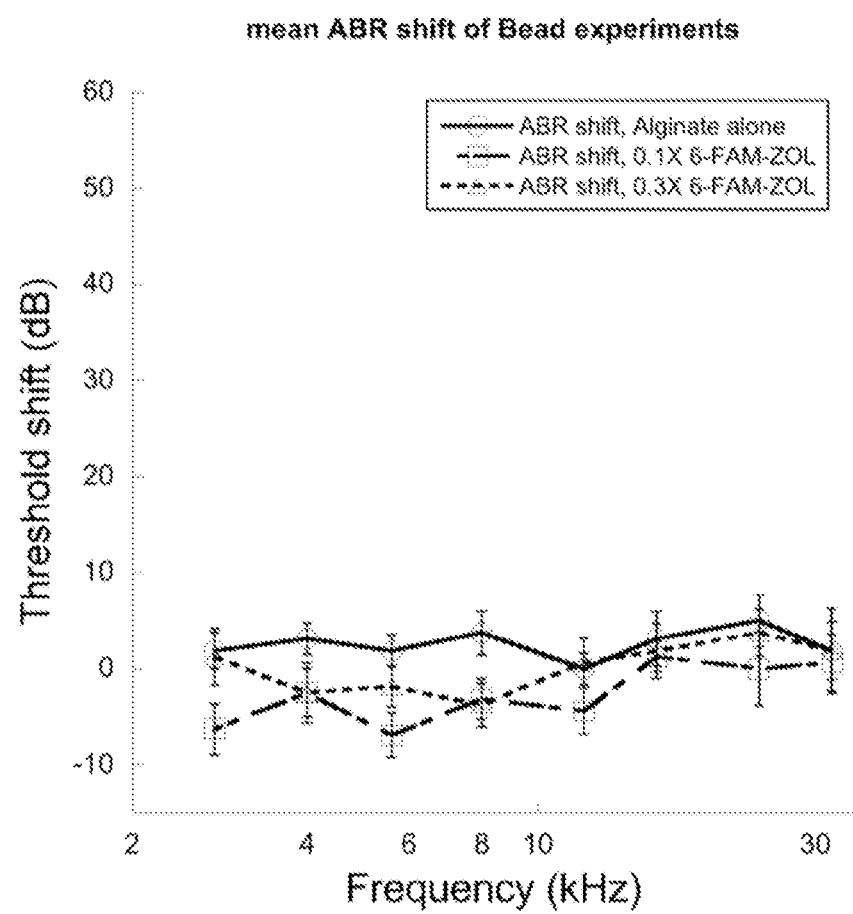
FIG. 7B shows the mean ABR shift of Bead experiments in a guinea pig model.

Placement on the round window membrane of an alginate bead containing 0.3×6-FAM-ZOL resulted in delivery of 6-FAM-ZOL throughout the lateral wall of the cochlea at levels comparable to the 1× systemic dose, while administration of 0.1×6-FAM-ZOL to the round window membrane resulted in lower, but still detectable, fluorescence, as shown in FIGS. 5A-C. When plotted as a function of distance along the cochlea, 6-FAM-ZOL-treated bone along the osseous spiral lamina of the modiolus exhibited a steeper gradient of fluorescence from base to apex (difference between regression line slopes $p<0.0001$), while no significant gradient was seen for measurements taken along the lateral wall of the same cochleae (difference between regression line slopes $p=0.09$). However, both the modiolus and the lateral wall had levels of fluorescence that were significantly higher than the control, as shown in FIGS. 6A-B. Notably, no shifts in ABR or DPOAE were observed three weeks after placement of 6-FAM-ZOL on the RWM, as shown in FIGS. 7A-B. It was concluded that placement of 30% of the 1× systemic 6-FAM-ZOL dose onto the RWM results in equivalent deposition of 6-FAM-ZOL in the lateral cochlear wall relative to the 1× systemic dose, and that local delivery of 6-FAM-ZOL in this manner was not ototoxic.

Example 8. Local Drug Delivery: 6-FAM-ZOL Infusion into the Scala Tympani Via a Cochleostomy in a Guinea Pig Model A Harvard Apparatus PHD 2000 Infusion Syringe Pump was used to introduce 6-FAM-ZOL into the cochlea. A 500 µL glass syringe, filled with 6-FAM-ZOL dissolved into AP at a concentration of 0.25 µg/µL, was connected via polyetherether ketone (PEEK; Upchurch Scientific) tubing to an 11 mm length of PTFE (teflon) tubing (201 µm outer diameter, 101 µm inner diameter). A small bleb approximately 600 µm in diameter was fabricated at a point 3 mm from the distal end using methyltriacetoxysilane (Elmer's Stix All).

A cochleostomy was performed approximately 0.5 mm distal to the round window via a bullectomy approach and the PTFE tubing was inserted into the scala tympani. Dental cement was used to seal the cochleostomy around the tubing. Infusion was performed at 1 µL over one minute, five times, spaced nine minutes apart. Control animals were treated with AP alone; 0.02× dosage animals were infused with 6-FAM-ZOL at 0.25 µg/µL; and 0.04× dosage animals were infused with 6-FAM-ZOL at 0.125 µg/µL+0.193 µg/µL zoledronate (total 4% of the 1× human zoledronate dose by molar weight). DPOAEs and CAPs were measured at time 0 (i.e., after cannula insertion and prior to infusion) and at 3 hrs. In independent experiments, three control animals were treated with AP alone, four animals were treated with AP containing 0.02×6-FAM-ZOL, and three animals were treated with AP containing 0.04×6-FAM-ZOL+zoledronate. Untreated animals were used for control tissue fluorescence analyses.

Figure 8A:
FIG. 8A shows fluorescent photomicrographs taken at mid-modiolar sections of untreated cochlea in a guinea pig.
Figure 8B:
FIG. 8B shows fluorescent photomicrographs taken at mid-modiolar sections of cochlea treated with direct cochlear infusion of 6-FAM-ZOL at 2% of the 1× systemic dose in a guinea pig.
Figure 9A:
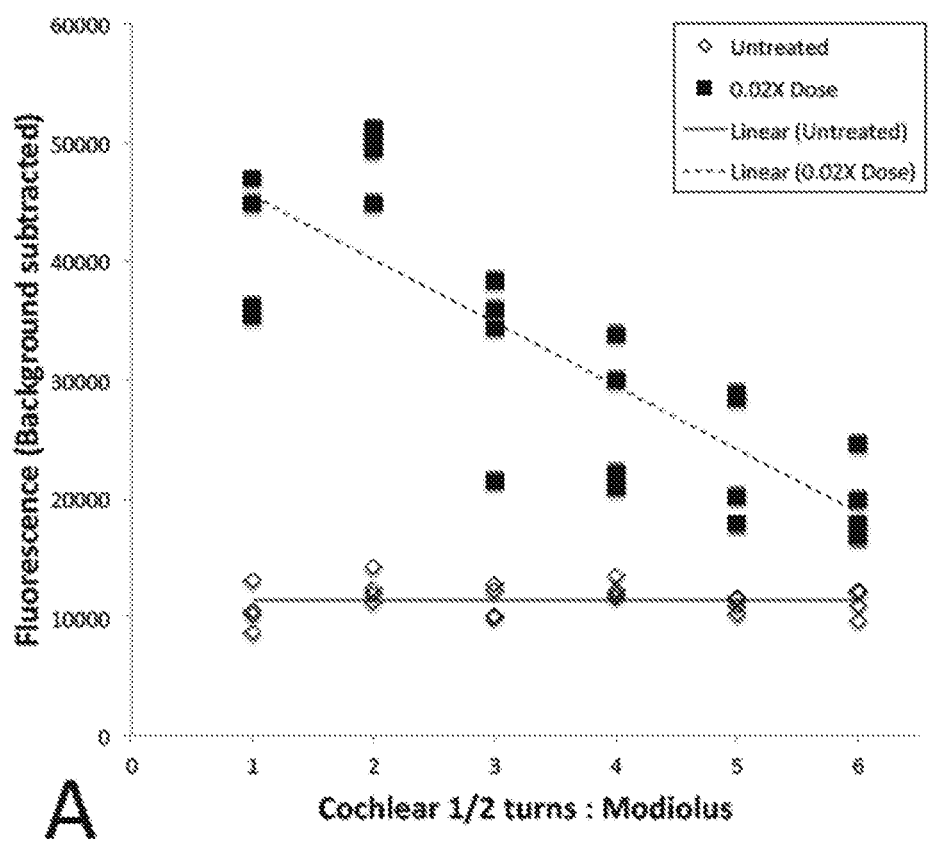
FIG. 9A shows quantification of fluorescence of the modiolus following cochlear infusion of 6-FAM-ZOL in a guinea pig. Measurements were taken at each of six cochlear half-turns from base to apex, along the modiolus. Total average fluorescence was significantly greater in 0.2× treatment ($p=0.0031$) and the slope of the 0.2× regression plot was significantly different from the control ($p=0.0003$).
Figure 9B:
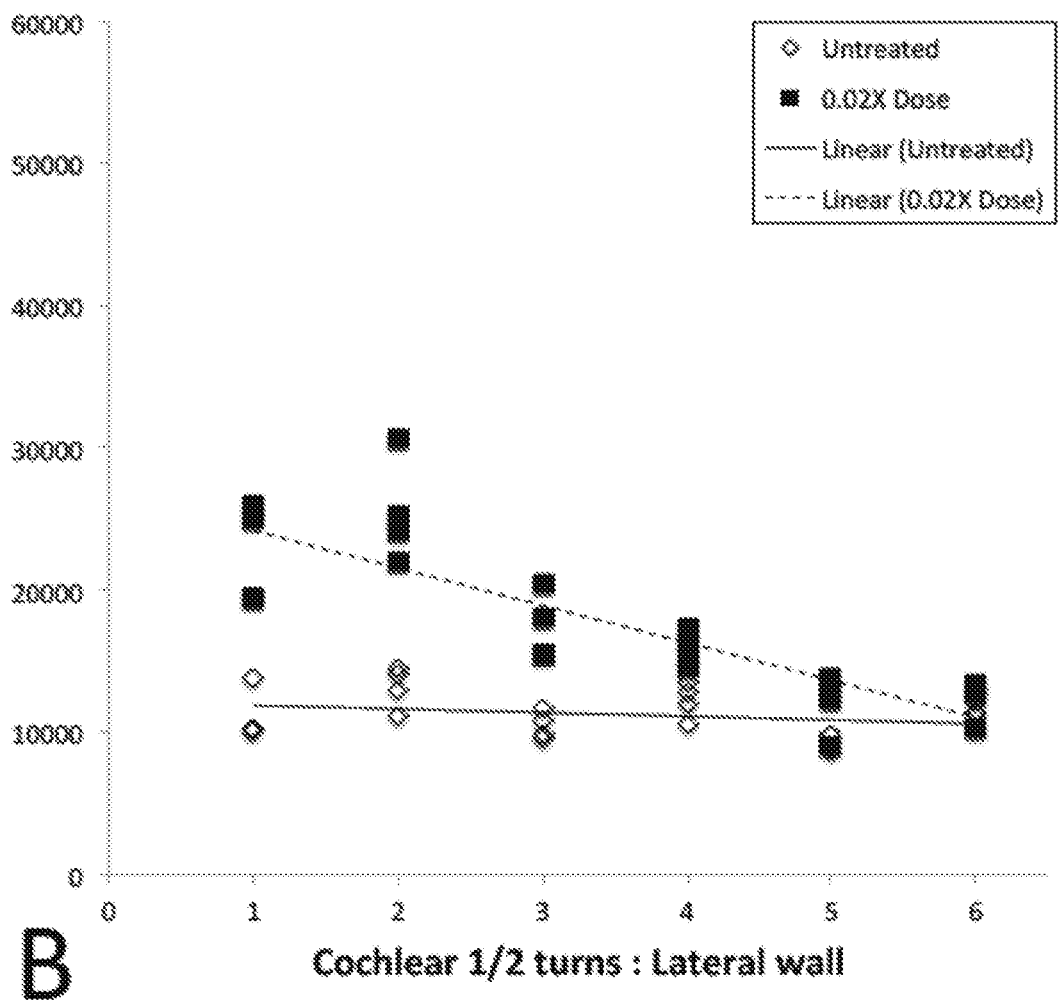
FIG. 9B shows quantification of fluorescence of the lateral wall following cochlear infusion of 6-FAM-ZOL in a guinea pig. Measurements were taken at each of six cochlear half-turns from base to apex, along the lateral wall. Total average fluorescence was significantly greater in 0.2× dose ($p=0.0124$) and the slope of the 0.2× regression plot was significantly different from the control ($p=0.0007$).

Following delivery of 2% (0.02×) of the 1× systemic 6-FAM-ZOL dose, bright fluorescent signal was identified along both the osseous spiral lamina of the modiolus and the lateral wall of the cochlea, as shown in FIGS. 8A-B. In addition, both the modiolus and the lateral wall exhibited significantly steeper gradients of signal from base to apex compared to the controls, as shown in FIGS. 9A-B (difference between regression line slopes $p<0.0001$).

Figure 10A:
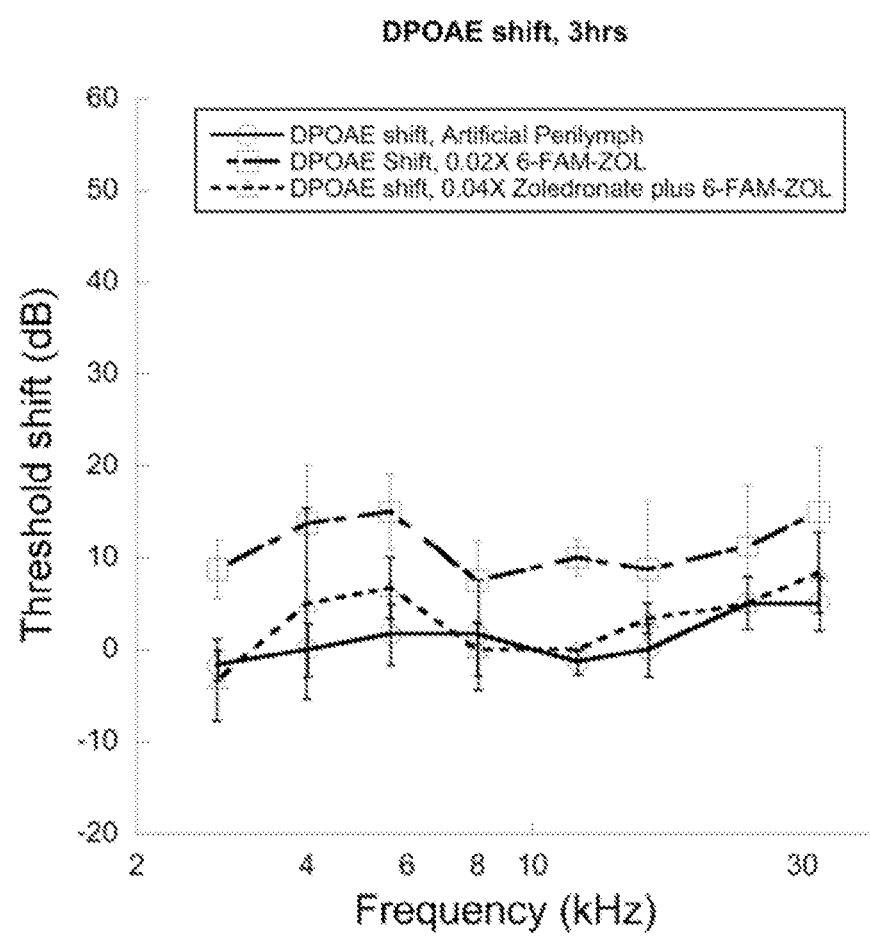
FIG. 10A shows the DPOAE shift at three hours for the artificial perilymph; 0.02×6-FAM-ZOL; and 0.04× Zoledronate+6-FAM-ZOL in a guinea pig.
Figure 10B:
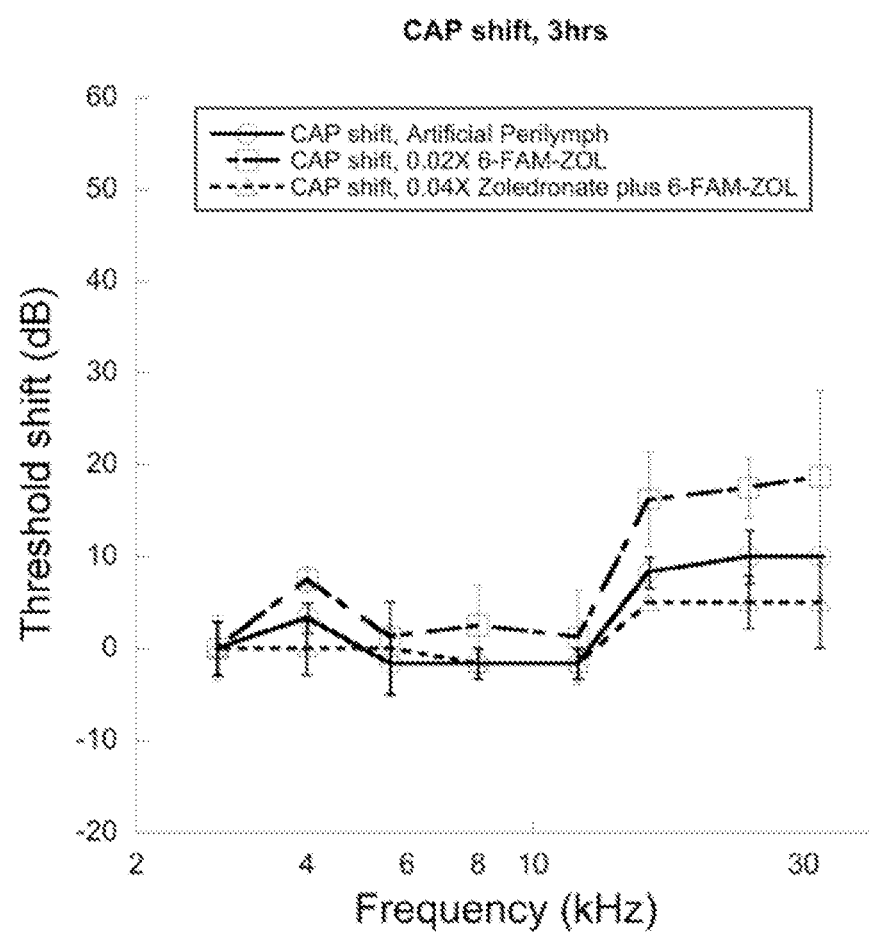
FIG. 10B shows the CAP shift at three hours for the artificial perilymph; 0.02×6-FAM-ZOL; and 0.04× Zoledronate+6-FAM-ZOL in a guinea pig.

In control animals, a small CAP shift was observed above 12 kHz, associated with the cochleostomy and injection procedure, while no significant DPOAE shift was seen in FIGS. 10A-B. In the 6-FAM-ZOL 0.02×-treated animals, a small additional shift was observed in both CAP and DPOAE, in the range of 10-15 dB. Additional cochleostomy delivery experiments were performed by infusing native zoledronate mixed with 6-FAM-ZOL to double the delivered bisphosphonate concentration to 0.04×. These animals showed no shift relative to control animals, as shown in FIGS. 10A-B. Direct infusion of 6-FAM-ZOL into the cochlea therefore results in very high levels of delivery relative to systemic or RWM delivery, and such delivery can be achieved without significant immediate ototoxicity.

Example 9. Human Temporal Bone Model

6-FAM-ZOL

6-FAM-ZOL was synthesized as described in Example 4 and was dissolved in artificial perilymph (AP) at a concentration of 10 µg/µL. The content of AP (pH 7.4) was 130 mM NaCl, 3.5 mM KCl, 1.5 mM CaCl2, 5.5 mM glucose, and 20 mM HEPES.

Delivery of 6-FAM-ZOL Through the Oval Window

Six freshly harvested cadaveric human temporal bones, which were obtained within 24 hours after death by the human temporal bone histopathology lab at Massachusetts Eye and Ear Infirmary, were used. The Pathology Quality Assurance Committee at Massachusetts General Hospital approved procurement of the specimens. The squamous and mastoid portions were drilled away, leaving the labyrinth. In three temporal bones, 1 µL of 10 µg/µL 6-FAM-ZOL was injected through the OW using a micropipette after lifting the stapes footplate. The footplate was then carefully laid back down. The other three temporal bones were treated with AP alone as controls. All specimens were placed in a sealed, humidified plastic container and left in the dark at room temperature for 4 days.

Tissue Processing

All subsequent steps were performed in covered vials to limit light exposure and prevent 6-FAM-ZOL bleaching. Specimens were fixed in an excess volume of neutral buffered formalin (10%, Fisher Scientific, Pittsburgh Pa.) at room temperature for one week, with one change of fixative at mid-week. The specimen were then dehydrated in an ascending series of ethanol (Fisher Scientific, 2 days at 70%, 1 hr at 70%, 1 hr at 85%, 40 min at 95%, 80 min at 100%) followed by a wash in xylene (Fisher Scientific) and a 30 minute immersion in xylene. The specimen were cleared of xylene by a 1 hour infiltration in methyl methacrylate (MMA, Acrylosin soft, Dorn and Hart, Villa Park, Ill.) under vacuum. The MMA solution was changed and the specimen were infiltrated for 24 hours under vacuum. The infiltration solution was changed and the process was repeated for another 2 days. The specimen were embedded in a solution of MMA containing 0.25% w/v (2.5 g/L) of perkadox-16 (Dorn and Hart) for several hours under vacuum. After several hours, the specimen were sealed in 50 mL polypropylene tubes and maintained at room temperature in a heat sink until fully cured (approximately 5 days). The hardened block was ground to a mid-modiolar section of the cochlea using a 12" table mounted rotary wheel.

Image Collection and Analysis

Figure 11:
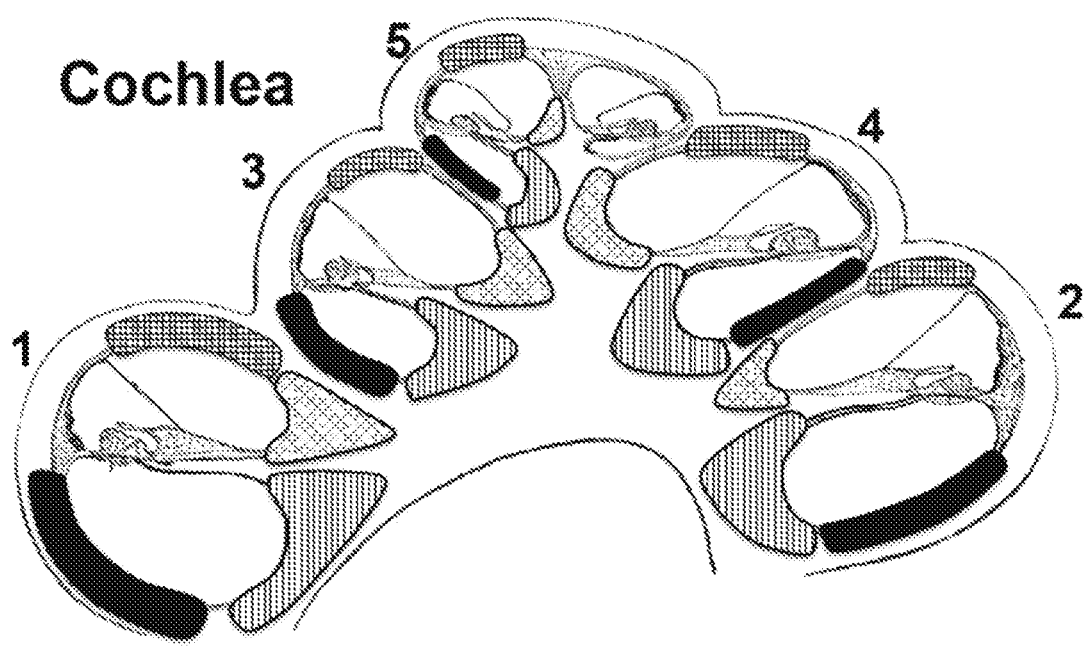
FIG. 11 shows a schematic of the human cochlea taken at a mid-modiolar section. Areas with reticular lines (lateral wall contacting the scala vestibuli), black solid areas (lateral wall contacting the scala tympani), dotted areas (modiolus contacting the scala vestibuli), and areas with vertical lines (modiolus contacting the scala tympani) at each half-turn were measured for fluorescence signals using the ImageJ program.

Images (1024 by 1024; 8 bit) were collected using a Leica TCS-SP2 confocal microscope to generate maximum fluorescence images. To identify the surface of each specimen, the point of maximum fluorescence in the z-axis was first identified. A stack of images was then collected to a depth of 500 μm from the point of maximum fluorescence. Images were obtained from control and experimental specimens in parallel at the same sitting under identical microscope settings. ImageJ was used to quantify the amount of fluorescence associated with the labeled bisphosphonate within the lateral cochlear wall and the modiolus of the scala vestibuli and scala tympani at each half-turn, as shown in FIG. 11.

Mixed model analysis of variance was performed using the SAS software package to analyze the effect of dose on fluorescent response in the cochlea. Null hypothesis were rejected at p>0.05.

After application of 6-FAM-ZOL through the oval window, a strong fluorescent signal was observed in the bony walls of the vestibular capsule, as shown in FIG. 12B and the cochlea, as shown in FIG. 12D. In the cochlea, signal intensity was highest in the basal turn and decreased toward the apex. There was very low background in specimens treated with artificial perilymph alone, as shown in FIGS. 12A and 12C. The fluorescent signal associated with 6-FAM-ZOL was quantified within the lateral and modiolar walls of the scala vestibuli and the scala tympani in both treated and control specimens. The bony walls of both the scala vestibuli and the scala tympani in specimens treated with 6-FAM-ZOL exhibited significant gradients of signal from base to apex of the cochlea, while those in the control specimens showed minimal fluorescence signal with no gradient, as shown in FIG. 13A-D. For both the lateral wall and the modiolus, a significant effect of dose (6-FAM-ZOL vs artificial perilymph) was observed both in the scala vestibuli and the scala tympani, as shown in FIG. 13A-D; all p<0.05. There was no significant effect of scalae location (scala vestibuli vs scala tympani) when evaluating signal either in the lateral wall or in the modiolus.

Example 10. Synthesis of DHF-BP

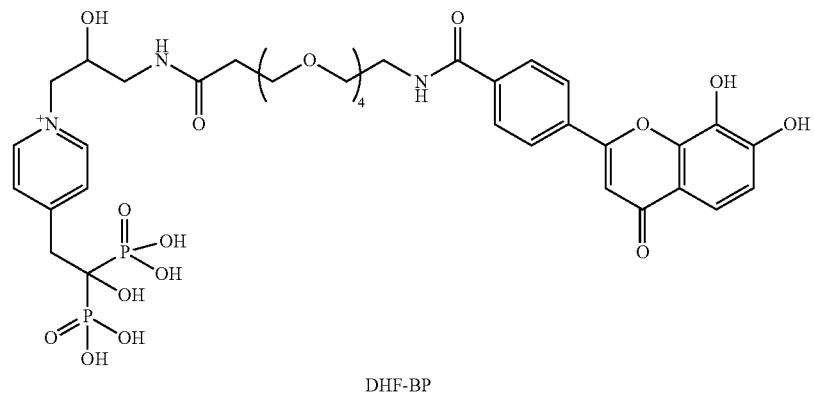

DHF-BP

The title conjugate was prepared according to the procedure described in Scheme 3.

Example 11. Synthesis of 1Aa-BP

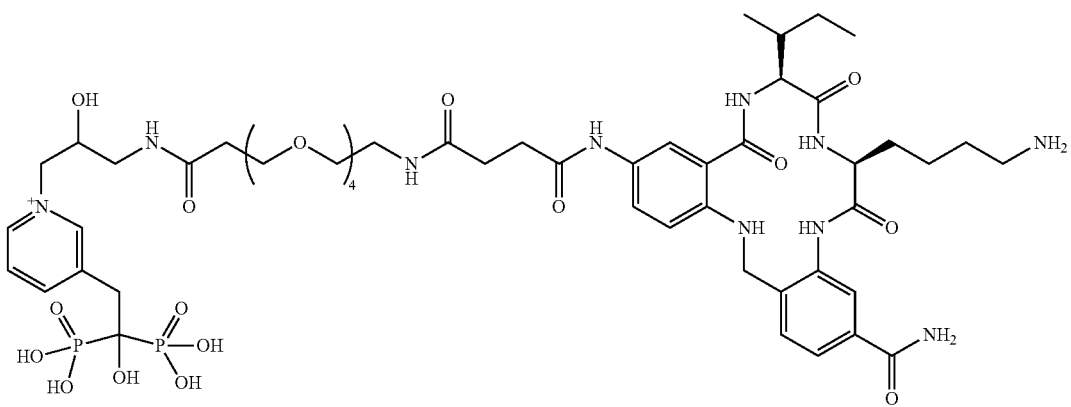

1Aa-BP

The title conjugate was prepared according to the procedure described in Scheme 4a.

Example 12. Synthesis of DHF-RIS-PC

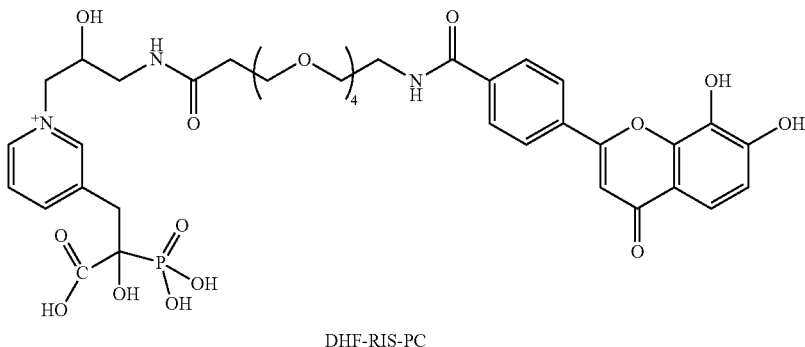

DHF-RIS-PC

The title conjugate was prepared according to the procedure described in Scheme 2. LC-MS (negative ion, M−): $t_{retention}$=7.83 min, calcd 848.26 m/z, found [M]−=848.15 m/z.

Example 13. In Vitro Neurite Outgrowth and Ribbon Synapse Regeneration

Figure 14A:
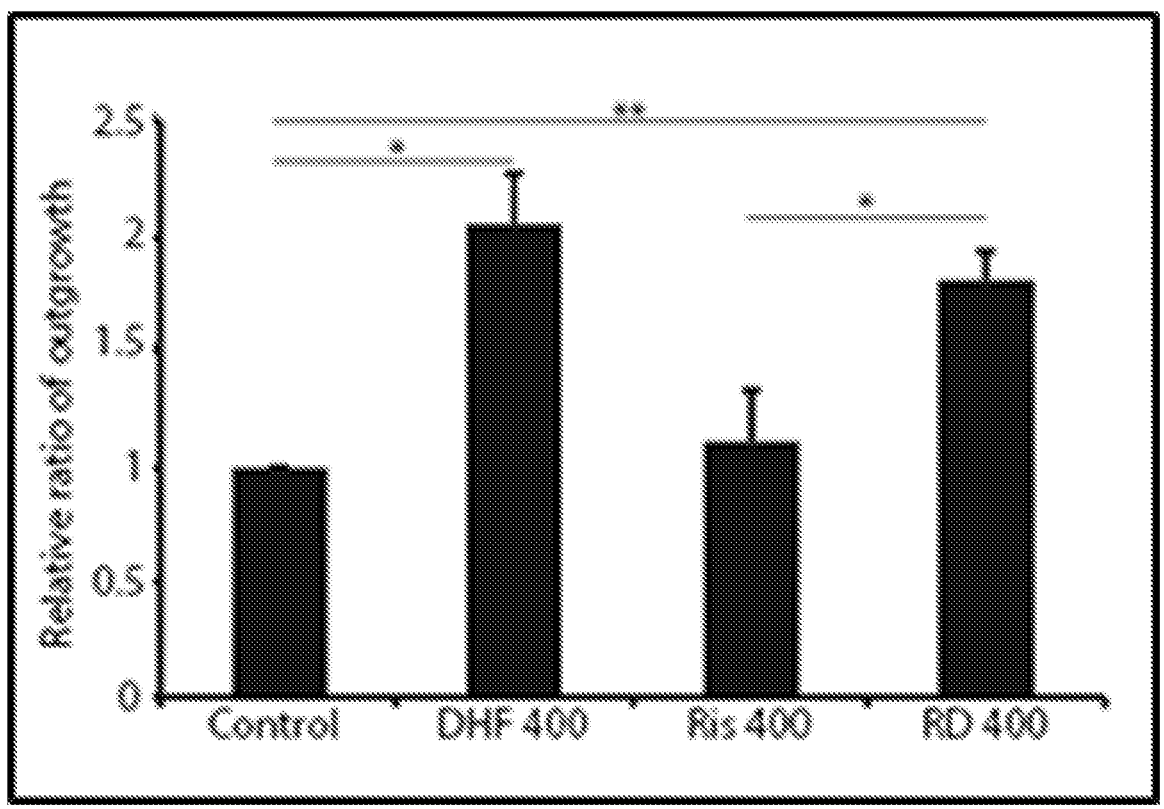
FIG. 14A shows a comparison of SG neurite outgrowth in vitro. Neurite length is expressed in ratios relative to the untreated control sample. Asterisks denote statistically significant differences (p<0.05).

Cochleae were harvested from P3-4 CBA/CaJ pups, after which the spiral ganglion neurons were sharply dissected free in a clump of cells, divided into three roughly equal sections, and plated with fibronectin on Dulbecco's Modified Eagle's medium (DMEM). Individual sections were then treated with media alone, 400 nM DHF, 400 nM RIS, or 400 nM DHF-RIS (Example 1) for 48 hours. After fixing and immunostaining with TUJ1, the neurites were visualized under confocal microscopy and the neurite length quantified using ImageJ. As shown in FIG. 14A, DHF-RIS-treated neurites demonstrated significant outgrowth.

To characterize the ability of DHF-RIS to regenerate ribbon synapses, a previously described organ of Corti explant system was used, wherein kainic acid was used to mimic excitotoxic damage to the ribbon synapse (see e.g., Wang et al, *The Journal of Neuroscience: the official journal of the Society for Neuroscience*, 2011, 31:7938-7949). Explants were treated with kainic acid for two hours to destroy synapses and then treated with 400 nM DHF, 400 nM RIS, or 400 nm DHF-RIS (Example 1). Comparison was made with control samples not treated with kainic acid (KA−) and samples treated with kainic acid but no other drug (KA+). Synapses were detected by co-localization of CtBP2 and PSD95 as previously described and counted using the Amira program by an observer blinded to sample identity. DHF-RIS demonstrated significant regeneration compared to non-rescued explants, although less than native DHF, as shown in FIG. 14B. RIS also showed some ability to regenerate synapses in this model. Without being bound by theory, this effect is believed to reflect an anti-apoptotic effect upon SGNs that has been previously demonstrated for bisphosphonate treatment in vitro (see e.g., Kao et al, *Neurobiology of Disease*, 2013, 56:25-33).

Figure 14C:
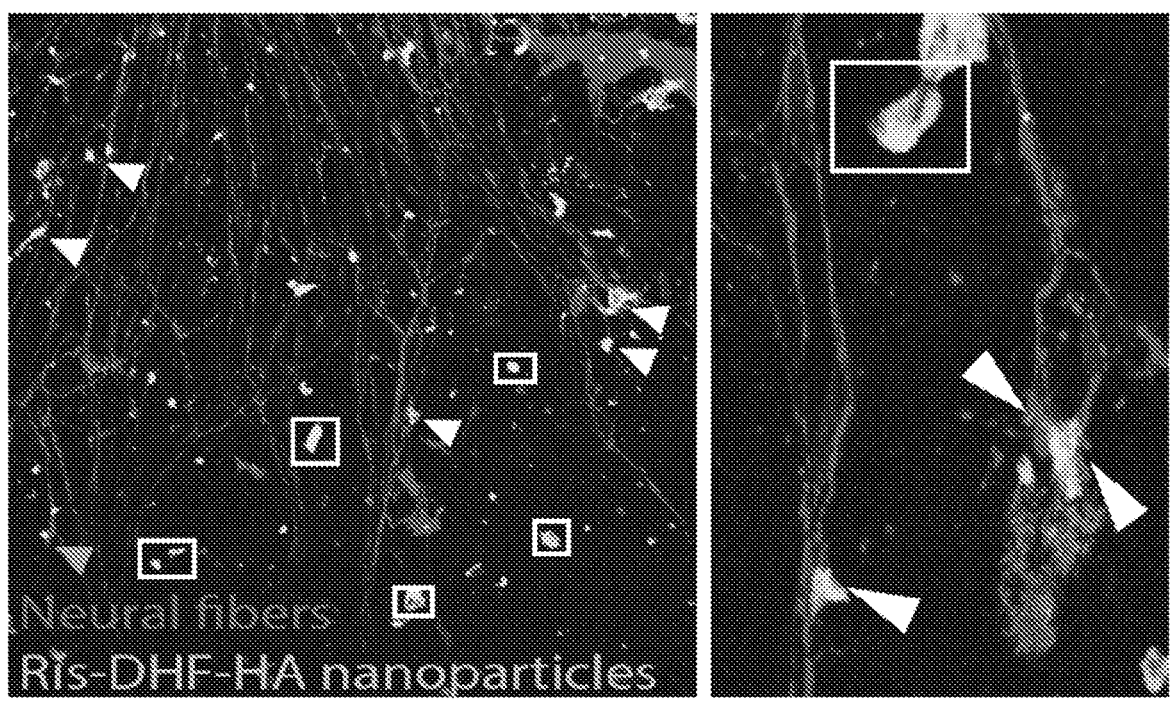
FIG. 14C shows that DHF-RIS (Example 1) is available to attract SG neurites (TuJ) after pre-binding to hydroxyapatite in vitro. A small amount of 6-FAM-ZOL was included with DHF-RIS to allow for visualization of the hydroxyapatite. Arrowheads denote areas of overlap between neurites and hydroxyapatite.

Example 14. In Vitro Attraction of SG Neurites after Pre-Binding with Hydroxyapatite This assay was performed to confirm that the DHF moiety within DHF-RIS (Example 1) remained available to attract neurites from a distance after binding to hydroxyapatite, a mineral substitute for bone. In a modification of the data shown in FIG. 14A, a separate set of experiments was performed in which RIS-DHF was pre-bound to hydroxyapatite pellets. The pellets were washed with media, and plated along with SGN explants. To visualize the hydroxyapatite pellets, a small amount of 6-FAM-ZOL (Example 4) was added to all samples. It was observed that neurites traveled up to 400 µM before ending on and overlapping with hydroxyapatite pellets, as shown in FIG. 14C. These results suggest that the DHF moiety remains available to attract neurites following DHF-RIS binding to bone through the RIS element.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A conjugate of Formula III:

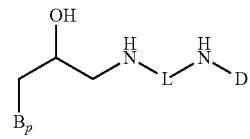

or a pharmaceutically acceptable salt thereof, wherein:
B$_p$ is selected from the group consisting of:

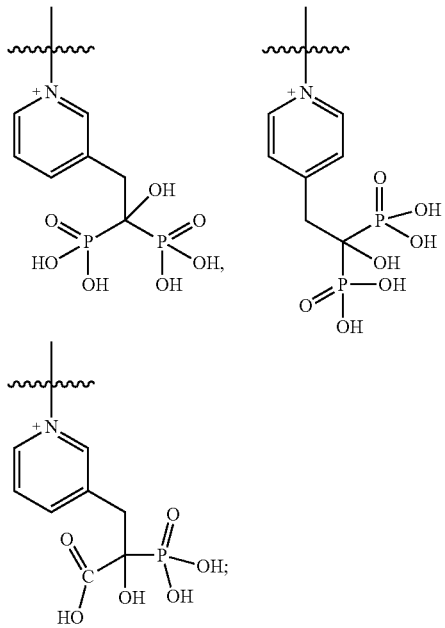

L is —C(O)—(C$_{1-4}$ alkylene)-(OCH$_2$CH$_2$)$_p$— and p is an integer from 1 to 10; and D is a neurotrophic therapeutic agent selected from the group consisting of 7,8-dihydroxy flavone and (7S,10S)-14-amino-7-(4-aminobutyl)-10-((S)-sec-butyl)-6,9,12-trioxo-5,6,7,8,9,10,11,12,17,18-decahydrodibenzo[h,l][1,4,7,11]tetraazacyclotetradecine-3-carboxamide, or a carbonyl-substituted analog thereof.

2. The conjugate of claim 1, or a pharmaceutically acceptable salt thereof, wherein L is —C(O)—(CH$_2$CH$_2$)—(OCH$_2$CH$_2$)$_p$— and p is an integer from 1 to 5.

3. The conjugate of claim 1, wherein the conjugate of Formula III is a conjugate of Formula V:

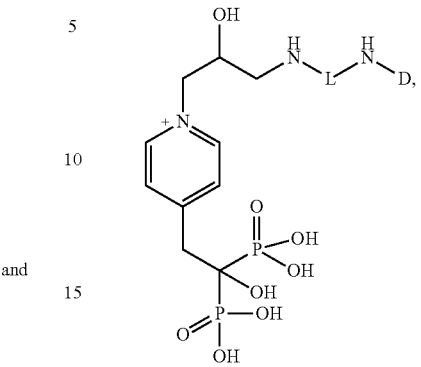

or a pharmaceutically acceptable salt thereof.

4. The conjugate of claim 1, wherein the conjugate of Formula III is a conjugate of Formula VIII:

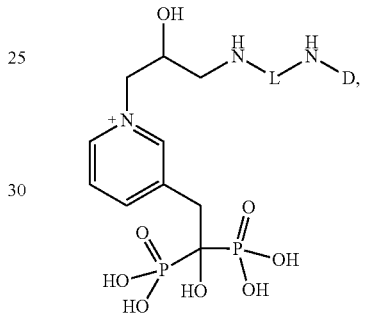

or a pharmaceutically acceptable salt thereof.

5. A conjugate, which is selected from the group consisting of:

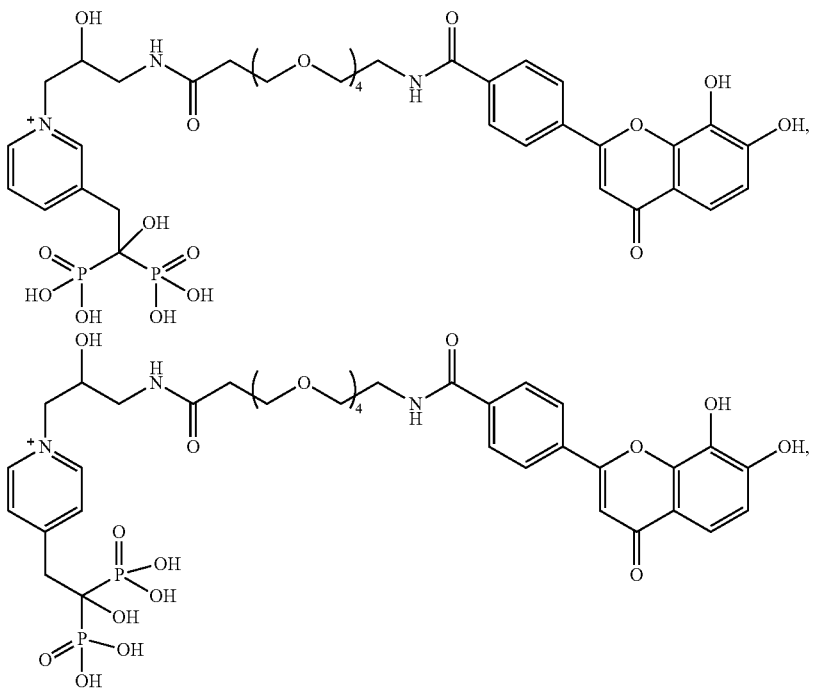

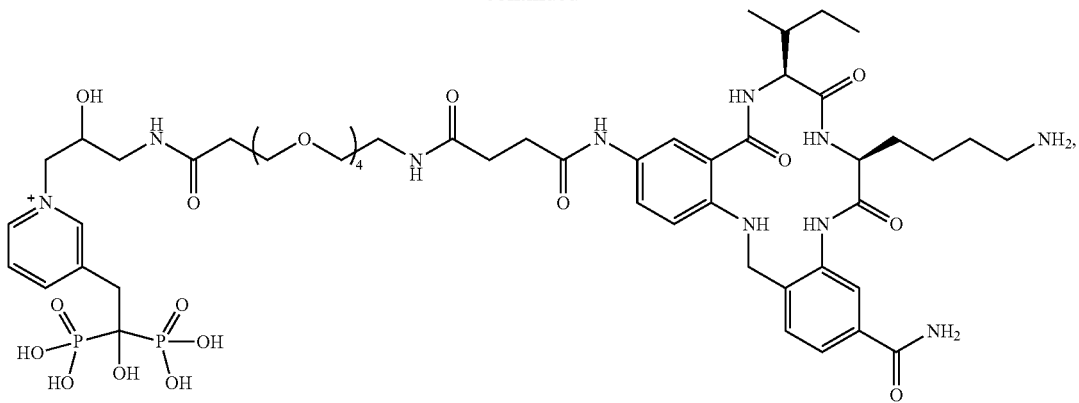
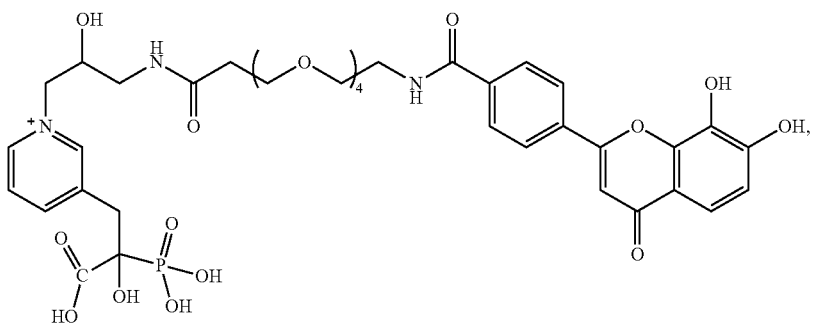
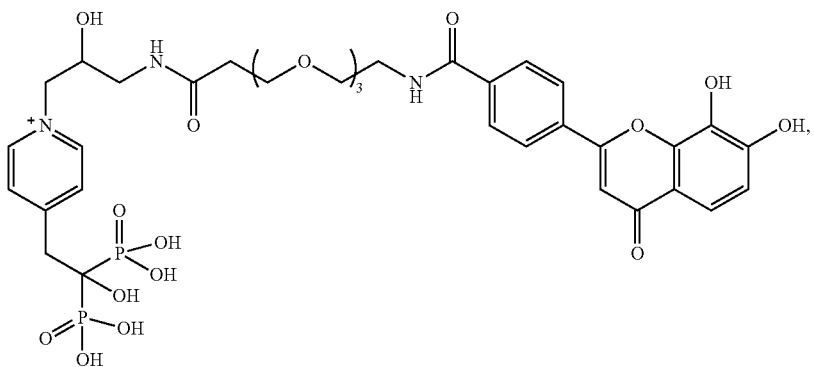
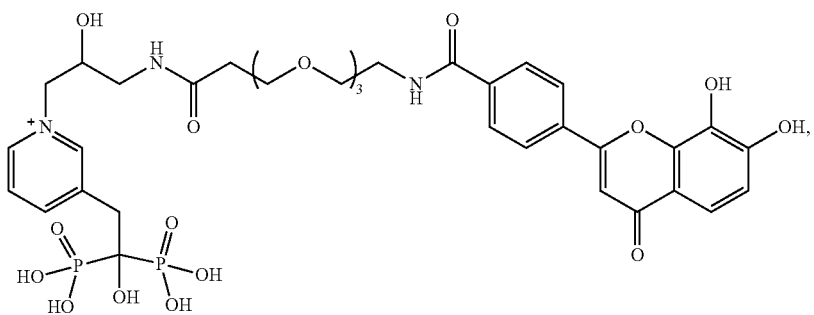

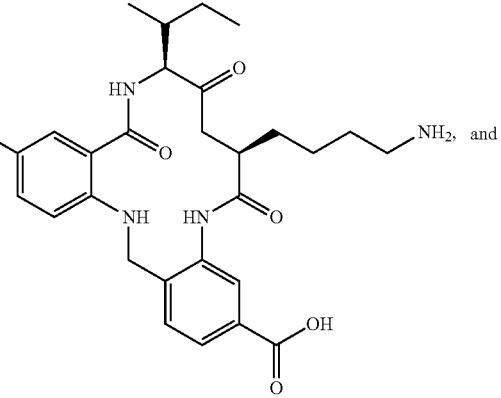
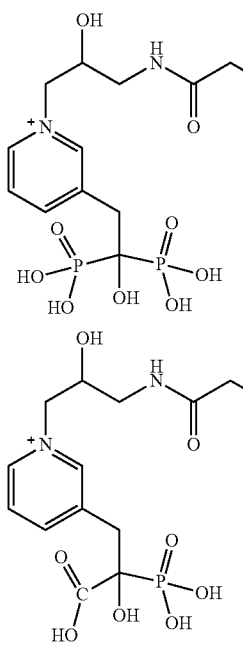

or a pharmaceutically acceptable salt thereof.

6. A pharmaceutical composition comprising the conjugate of claim 1, or a pharmaceutically acceptable salt thereof, and a pharmaceutically acceptable carrier.

7. The conjugate of claim 1, or a pharmaceutically acceptable salt thereof, wherein $B_p$ is

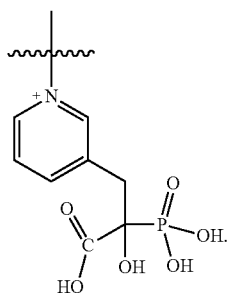

8. The conjugate of claim 1, or a pharmaceutically acceptable salt thereof, wherein L is —C(O)—(CH$_2$CH$_2$)—(OCH$_2$CH$_2$)$_p$— and p is an integer from 3 to 4.

9. A conjugate, which is:

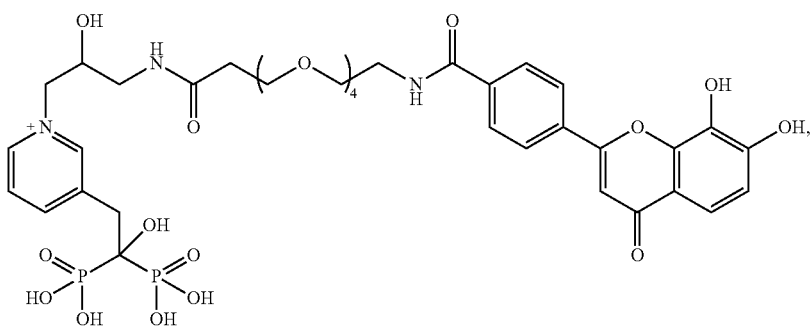

or a pharmaceutically acceptable salt thereof.

10. A pharmaceutical composition comprising the conjugate of claim 9, and a pharmaceutically acceptable carrier.

\* \* \* \* \*

UNITED STATES PATENT AND TRADEMARK OFFICE
CERTIFICATE OF CORRECTION

PATENT NO. : 11,331,391 B2  
APPLICATION NO. : 16/072456  
DATED : May 17, 2022  
INVENTOR(S) : Charles E. McKenna et al.

Page 1 of 1

It is certified that error appears in the above-identified patent and that said Letters Patent is hereby corrected as shown below:

In the Specification

In Column 1, Lines 14-15, delete "Numbers DC015824, DC000038, and W81XWH-15-1-0472" and insert -- Number DC009837 --

In Columns 83-84, Lines 1-15 (Approx.), delete

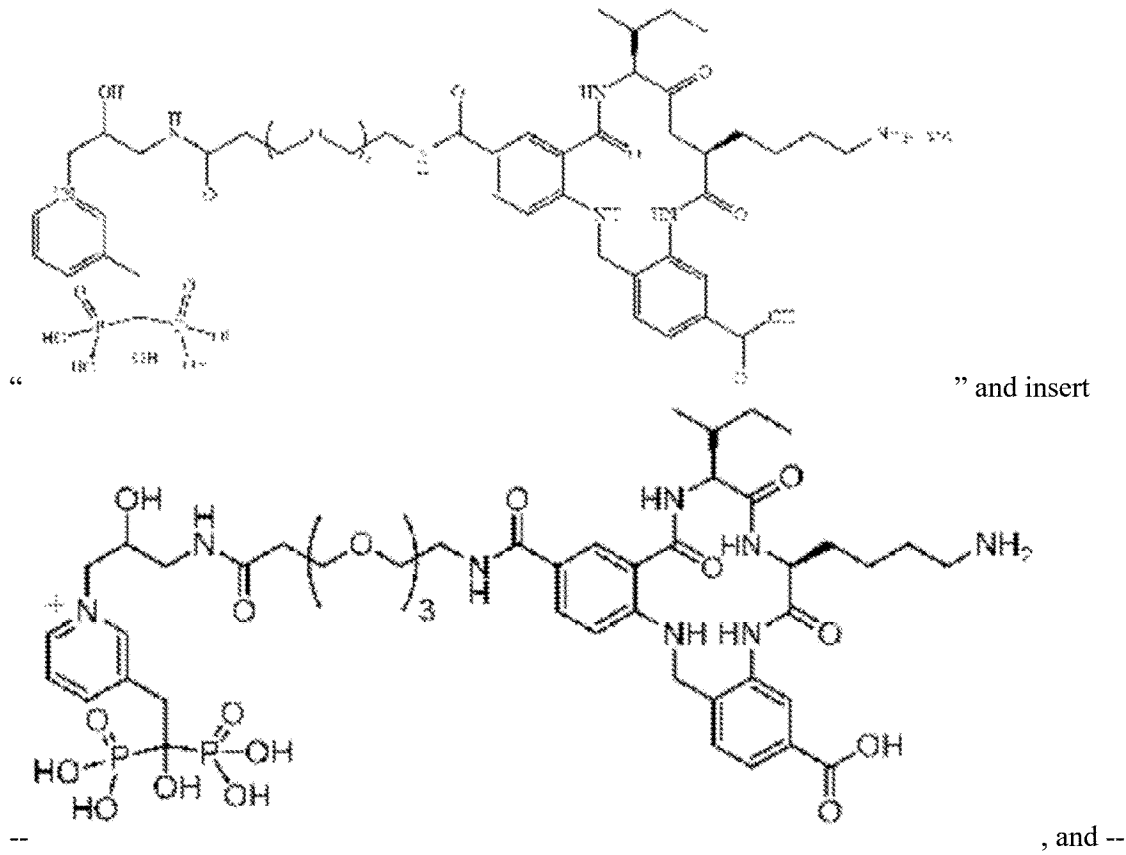

" and insert

" , and --

Signed and Sealed this  
Ninth Day of August, 2022

*Katherine Kelly Vidal*

Katherine Kelly Vidal  
*Director of the United States Patent and Trademark Office*